(12) United States Patent
Schmidt

(10) Patent No.: US 11,104,929 B2
(45) Date of Patent: Aug. 31, 2021

(54) METHODS FOR PRODUCING RIBOSOMALLY SYNTHESIZED AND POSTTRANSLATIONALLY MODIFIED PEPTIDES

(71) Applicant: UNIVERSITY OF UTAH RESEARCH FOUNDATION, Salt Lake City, UT (US)

(72) Inventor: Eric Schmidt, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 16/915,927

(22) Filed: Jun. 29, 2020

(65) Prior Publication Data

US 2021/0040529 A1   Feb. 11, 2021

Related U.S. Application Data

(62) Division of application No. 15/770,176, filed as application No. PCT/US2016/057105 on Oct. 14, 2016, now Pat. No. 10,731,196.

(60) Provisional application No. 62/241,583, filed on Oct. 14, 2015.

(51) Int. Cl.

| C12N 1/20 | (2006.01) |
|---|---|
| C12P 21/02 | (2006.01) |
| C07K 14/195 | (2006.01) |
| C12N 9/48 | (2006.01) |
| C12N 15/52 | (2006.01) |
| C12N 15/74 | (2006.01) |
| C12R 1/19 | (2006.01) |

(52) U.S. Cl.
CPC ............ *C12P 21/02* (2013.01); *C07K 14/195* (2013.01); *C12N 1/20* (2013.01); *C12N 1/205* (2021.05); *C12N 9/48* (2013.01); *C12N 15/52* (2013.01); *C12N 15/74* (2013.01); *C12R 2001/19* (2021.05); *C12Y 501/01* (2013.01)

(58) Field of Classification Search
CPC .......... C12N 1/20; C12N 15/52; C12N 15/74
See application file for complete search history.

(56) References Cited

U.S. PATENT DOCUMENTS

| 9,249,411 B2 | 2/2016 | Christiansen | |
| 10,731,196 B2 * | 8/2020 | Schmidt | ................... C12N 1/20 |
| 2019/0194712 A1 | 6/2019 | Schmidt | |

OTHER PUBLICATIONS

Donia et al., (2008), "A global assembly line for cyanobactins," Nature Chemical Biology 4(6):341-343.
Donia et al., (2011), "Accessing the hidden majority of marine natural products through metagenomics," Chembiochem: a European journal of chemical biology 12(8):1230-1236.
Gibson, (2011), "Enzymatic assembly of overlapping DNA fragments," Methods in enzymology 498:349-361.
Hanson et al., (2004), "Investigating mitochondrial redox potential with redox-sensitive green fluorescent protein indicators;" The Journal of biological chemistry 279(13):13044-13053.
International Search Report and Written Opinion for Application No. PCT/US2016/057105 dated Dec. 1, 2017 (14 pages).
Martin et al., (2003), Engineering a mevalonate pathway in *Escherichia coli* for production of terpenoids, Nature biotechnology 21(7):796-802.
Mcintosh et al., "Insights into heterocyclization from two highly similar enzymes," Journal of the American Chemical Society, 2010, 132:4089-91.
Ohtsu et al, "The L-cysteine/L-cystine shuttle system provides reducing equivalents to the periplasm in *Escherichia coli*," J Biol Chem, Jun. 4, 2010, vol. 285, vol. 23, pp. 17497-17487.
Pfeifer et al., (2002), "Process and metabolic strategies for improved production of *Escherichia coli*-derived 6-deoxyerythronolide B," Applied and environmental microbiology 68(7):3287-3292.
Raghuraman et al., (2014), "Defining modulatory inputs into CNS neuronal subclasses by functional pharmacological profiling," Proceedings of the National Academy of Sciences of the United States of America 111 (17):6449-6454.
Ruffner et al., "Assessing the combinatorial potential of the RiPP cyanobactin tru pathway," ACS Synth Biol, Apr. 17, 2015, vol. 4, No. 4, pp. 482-492.
Sardar et al., "Modularity of RiPP Enzymes Enables Designed Synthesis of Decorated Peptides," Chem Biol, Jun. 23, 2015, vol. 22, No. 7, pp. 907-916.
Teichert et al, (2012), "Characterization of two neuronal subclasses through constellation pharmacology," Proceedings of the National Academy of Sciences of the United States of America 109(31):12758-12763.
Tianero et al., "Metabolic model for diversity-generating biosynthesis," Proc Nat Acad Sci Epub, Feb. 1, 2016, vol. 113, No. 7, pp. 1772-1777.
Tianero et al., (2012), "Ribosomal route to small-molecule diversity," Journal of the American Chemical Society 134 (1):418-425.
Wycuff et al., (2000), "Generation of an AraC-araBAD promoter-regulated T7 expression system," Anal Biochem 277(1):67-73.

\* cited by examiner

*Primary Examiner* — Tekchand Saidha
(74) *Attorney, Agent, or Firm* — Michael Best & Friedrich LLP

(57) ABSTRACT

The disclosure provides recombinant cells and methods for producing a ribosomally synthesized and posttranslationally modified peptide (RiPP), as well as RiPP libraries and methods for producing RiPP libraries.

13 Claims, 40 Drawing Sheets

Specification includes a Sequence Listing.

patellin 2  patellin 3  trunkamide patellamide A  patellamide C isoprene: 0, 1, or 2

# METHODS FOR PRODUCING RIBOSOMALLY SYNTHESIZED AND POSTTRANSLATIONALLY MODIFIED PEPTIDES

CROSS-REFERENCE TO RELATED APPLICATION(S)

This application is a divisional of U.S. patent application Ser. No. 15/770,176, filed on Apr. 20, 2018, which is a U.S. national stage entry of International Patent Application No. PCT/US2016/057105, filed on Oct. 14, 2016, which claims priority to U.S. Provisional Patent Application No. 62/241,583, filed on Oct. 14, 2015, the entire contents of each of which are fully incorporated herein by reference.

STATEMENT REGARDING FEDERALLY SPONSORED RESEARCH OR DEVELOPMENT

This invention was made with government support under Grant Number GM102602 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 4,227 bytes ASCII (Text) file named "U-6013-026389-9175-US03-SEQ-LIST-06-29-20.txt," created on Jun. 29, 2020.

TECHNICAL FIELD

The present disclosure provides cells and methods for producing a ribosomally synthesized and posttranslationally modified peptide (RiPP), as well as RiPP libraries and methods for producing RiPP libraries.

BACKGROUND

Ribosomally synthesized and posttranslationally modified peptides (RiPPs) are peptide molecules characterized by extensive posttranslational modifications. RiPPs are initially synthesized on precursor peptides that include a core peptide that is converted into the RiPP product. Enzymatic modifications to the core peptide, and usually proteolytic cleavage of the core from the precursor peptide, yield smaller, chemically modified RiPP molecules.

For example, the cyanobacterial tru and pat pathways allow production of cyanobactin RiPPs. While such RiPPs have been experimentally produced, a limitation was low and variable yield. Methods that are commonly used with narrower-substrate pathways, such as optimizing transcription, translation, and folding, afforded only modest yield improvements. A need exists for cells and methods for allowing RiPP production with consistent and high yields.

SUMMARY

The present disclosure provides methods and recombinant cells useful for producing RiPPs with high yield. The recombinant cells may comprise a nucleic acid encoding a tru protein or a pat protein. The recombinant cells may further comprise a nucleic acid encoding a mev protein. The disclosed methods may comprise culturing a recombinant cell in the presence of an exogenous sulfide source. In addition, the disclosed methods may comprise culturing a recombinant cell in the presence of exogenous mevalonate.

BRIEF DESCRIPTION OF THE DRAWINGS

FIG. 1 shows generation of chemical diversity by cyanobactin pathways.

FIG. 3 shows sulfide liberated from cysteine increases compound production.

FIG. 4 shows that hydrogen sulfide modulates substrate preference of early cyanobactin pathway enzymes. The purified enzymes ThcD and PatA were combined with the substrate TruE-3-2 in vitro, and reactions were run for 6 h in triplicate. When NaHS (500 µM) was added to the reaction medium, more of the correct products were obtained after 6 h than absent sulfide. By contrast, all enzymes proceeded at similar rates with or without sulfide (see FIG. 18 for a full set of conditions and reactions).

FIG. 5 shows that mevalonate increases cyanobactin RiPP synthesis independently of prenylation.

FIG. 9 shows standard curves of 1,4-dinitrobenzene and patellins 2 used for quantification of production.

FIG. 11 shows cysteine does not function through redox effects.

1 pTara, pUC19, pET28
2 pTara, pUC19, pET28+cys
3 pTara, pTruA, pET28
4 pTara, pTruA, pET28+cys
5 his-pagF
6 pTara, ptru, pET28
7 pTara, ptru, pET28+cys
8 pTara, pUC19, pTruE2
9 pTara, pUC19, pTruE2+cys
10 his-pagF
11 pTara, pTruA, pTruE2
12 pTara, pTruA, pTruE2+cys
13 pTara, ptru, pTruE2
14 pTara, ptru, pTruE2+cys

1 un-tagged tru (pTru-patellin 2-patellin 2)
2 un-tagged tru
3 un-tagged tru+cys
4 un-tagged tru+cys
5 un-tagged tru+cys
6 his-tagged tru (pTru-his-int)
7 his-tagged tru
8 his-tagged tru
9 his-tagged tru+cys
10 his-tagged tru+cys
11 his-tagged tru+cys
12 his-tagged PagF/TruE2 std
FIG. 17 shows metabolomic analyses showing minimal metabolic changes in E. coli in the presence of cysteine.

FIG. 18 shows the effect of sulfide on N-terminal proteolysis. PatA reactions were performed on TruE-3-2 substrate in assays with Tris pH 7.5 (50 mM), $MgCl_2$ (5 mM), $CaCl_2$ (10 mM), ATP (1 mM), PatA (2 µM) and substrate TruE-3-2 (50 µM) with or without the addition of $Na_2S$ (500 µM) at varying time-points as indicated. In some reactions as described below ThcD (2 µM) was added. Three sets of reaction were carried out, where the first set comprised TruE-3-2 reaction with PatA, the second set was of HPLC-purified pure heterocyclized TruE-3-2 with PatA, in which case the concentration of the heterocyclized substrate was lower than 50 µM and was not definitively determined, and the third set was of TruE-3-2 reaction with PatA in presence of ThcD. Reactions were analyzed by HPLC-MS and/or SDS-PAGE at varying time-points as detailed below.

6)+TVPTLC*SYDD (SEQ ID NO: 7) PatA intermediates (where C*=thiazoline). These were used in a reaction with TruG (17 µM) in presence of Tris pH 7.5 (50 mM) and MgCl$_2$ (5 mM), in the presence or absence of Na$_2$S (500 µM) at varying time-points as given. FIG. 18G is the mass spectra of TruG products, which correspond to non-prenylated patellin 3 and patellin 2. FIG. 18H shows a time-course of TruG reaction with and without sulfide. Each data-point at every time-point is an average of duplicates and error bars represent standard deviation.

FIG. 20 shows timing of cyclic peptide production and loss of cysteine in cultures.

FIG. 21 shows the effect of mevalonate on tru pathway expression. Vectors comprising sequences encoding tru pathway proteins (pTru-SD, denoted as "pTru"), comprising sequences encoding tru pathway proteins fused with GFP (Topo-E1-S316-GFP-F4, denoted as "pTru_gfp"), comprising sequences encoding a redox-sensitive version of GFP (pRSFlac-roGFP2), and comprising sequences encoding mev pathway proteins (pMBI) were introduced into E. coli cells in different combinations. In particular, cells were transformed with pTru, pTru_gfp, or pRSFlac-roGFP2 with and without pMBI. Cells were grown in 2xYT broth with 10 mM cysteine containing different concentrations of mevalonate. Fluorescence intensity was measured and normalized by OD600. Each data point is an average of triplicates and error bars present standard deviation.

FIG. 22 shows the role of cysteine on the mevalonate effect of tru pathway transcription. Vectors comprising sequences encoding tru pathway proteins (pTru-SD, denoted as "pTru"), comprising sequences encoding tru pathway proteins fused with GFP (Topo-E1-S316-GFP-F4, denoted as "pTru_gfp"), comprising sequences encoding a redox-sensitive version of GFP (pRSFlac-roGFP2), and comprising sequences encoding mev pathway proteins (pMBI) were introduced into E. coli cells in different combinations. Mevalonate (20 mM) was added to 2xYT broth with and without cysteine (10 mM). Fluorescence intensity was normalized by OD600. Each data point is an average of triplicates and error bar represents standard deviation.

DETAILED DESCRIPTION

Figure 1A:
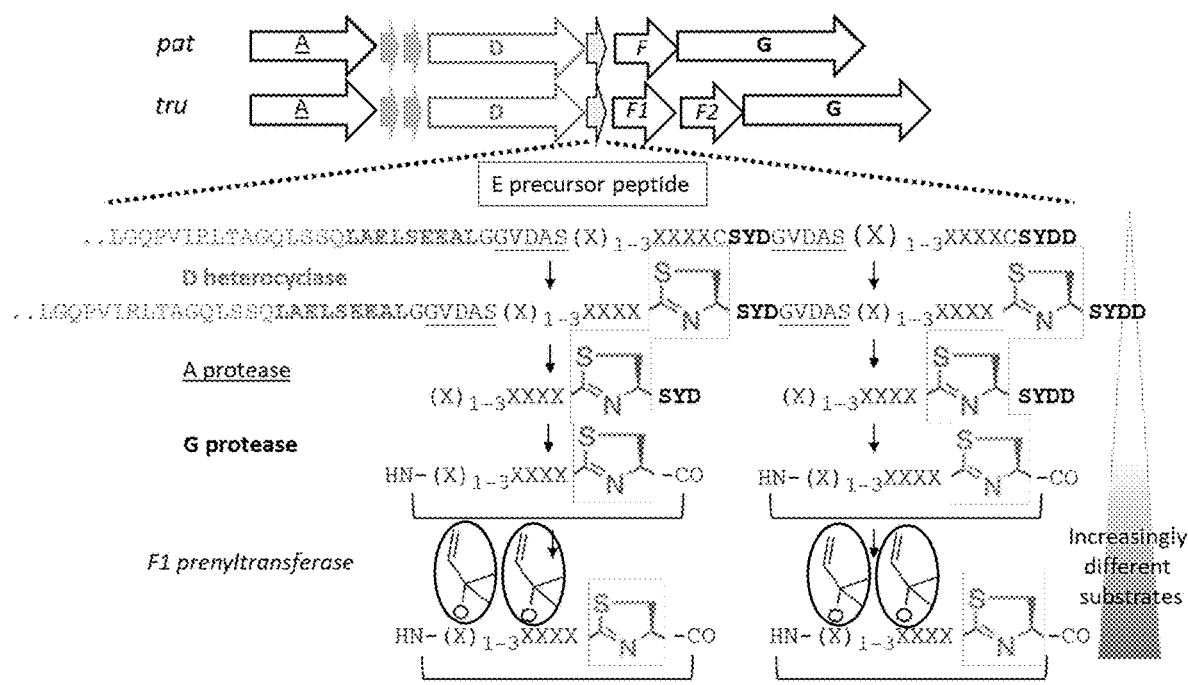
FIG. 1A shows the biosynthesis of cyanobactins by the pat and tru pathways. The relationships between the precursor peptide recognition sequences and the relevant enzymes are indicated. For example, a PatA/TruA protease recognition sequence (GVDAS, SEQ ID NO: 1) is gray and underlined. A PatD/TruD heterocyclase recognition motif is shown with gray bolding. Example PatG/TruG protease recognition sequences are shown black and bolded (SYD, SEQ ID NO: 2; or SYDD, SEQ ID NO: 3). Example prenylation sites for TruF1 prenyltransferase are indicated by prenyl groups (circled). "X" indicates regions that can be highly variable. Because these elements are progressively cleaved during biosynthesis, the substrate for each ensuing enzyme in the pathway is progressively different in structure.

The disclosure provides recombinant cells and methods for producing RiPPs. The disclosed methods and recombinant cells may enable production of RiPPs with high yield. The disclosure also provides for the production of diverse RiPP libraries. The disclosed methods may include culturing a recombinant cell expressing a tru protein or a pat protein in the presence of an exogenous sulfide source.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents, and other references mentioned herein are hereby incorporated by reference in their entireties. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. METHODS FOR PRODUCING A RiPP

Provided herein are methods for producing a RiPP. The disclosed methods permit production of RiPPs with high yield, and may achieve RiPP yields of 27 mg/L or more. The method may generate about 250 mg/L RiPP precursor peptide, or about 25% of the cellular dry weight. Yield may be calculated by dividing the mass of RiPP peptide produced by the volume of recombinant cell culture used.

The methods may include introducing into a cell a nucleic acid that encodes at least one cyanobactin pathway protein. The cyanobactin pathway protein may comprise at least one tru protein, at least one pat protein, or a combination of at least one tru protein and at least one pat protein. The methods may further include introducing into a cell a nucleic acid that encodes at least one mev protein. The methods may further include culturing a cell in the presence of an exogenous sulfide source. The methods may also include culturing a cell in the presence of exogenous mevalonate.

a. Nucleic Acid

The methods may include introducing into a cell a nucleic acid that encodes at least one cyanobactin pathway protein. The nucleic acid may be DNA. The cell is described below in more detail. The nucleic acid may contain one or more genes encoding one or more cyanobactin pathway proteins. A pathway is a reaction module, often encoded by a gene cluster or operon, that is aimed to synthesize a product and that may be part of a larger metabolic network.

The tru and related pat cyanobactin pathways catalyze production of ribosomally synthesized and posttranslationally modified peptide (RiPP) products and were first identified in cyanobacterial symbionts of coral reef animals. Both tru and pat accept a wide variety of hypervariable substrates, yet the enzymes are essentially sequence identical. The tru and pat pathways are each capable of synthesizing potentially millions of compounds with highly diverse structures.

Figure 1B:
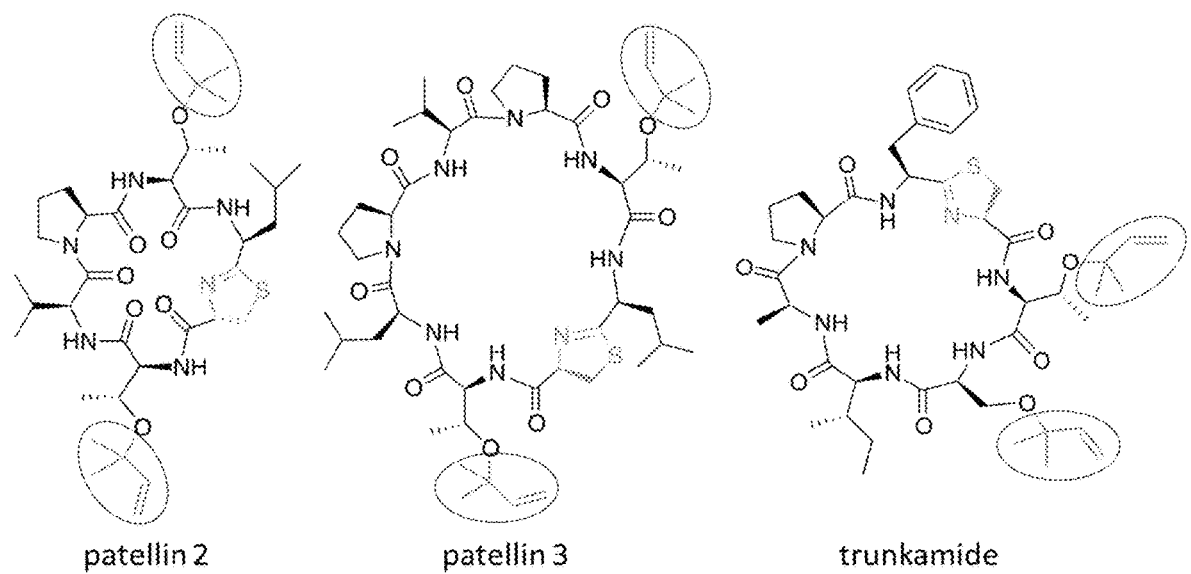
FIG. 1B are cyanobactin RiPPs produced in this study: patellin 2, patellin 3, trunkamide, patellamide A, patellamide C. Prenyl groups (circled) indicate example sites of action of the TruF1 prenyltransferase, which installs 0-2 isoprene units on serine or threonine.
Figure 1B:
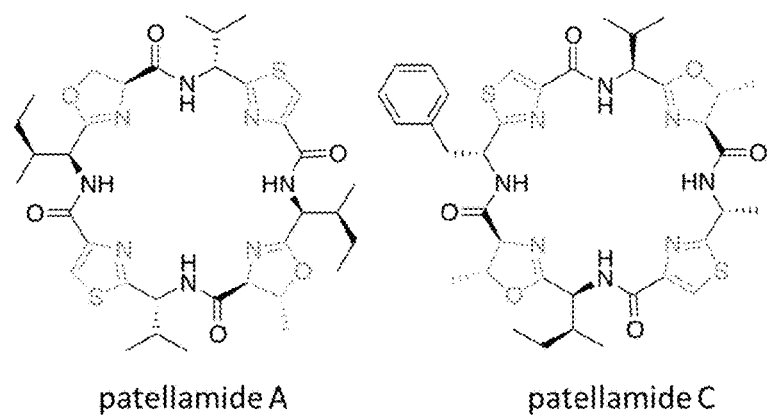
Figure 8A:
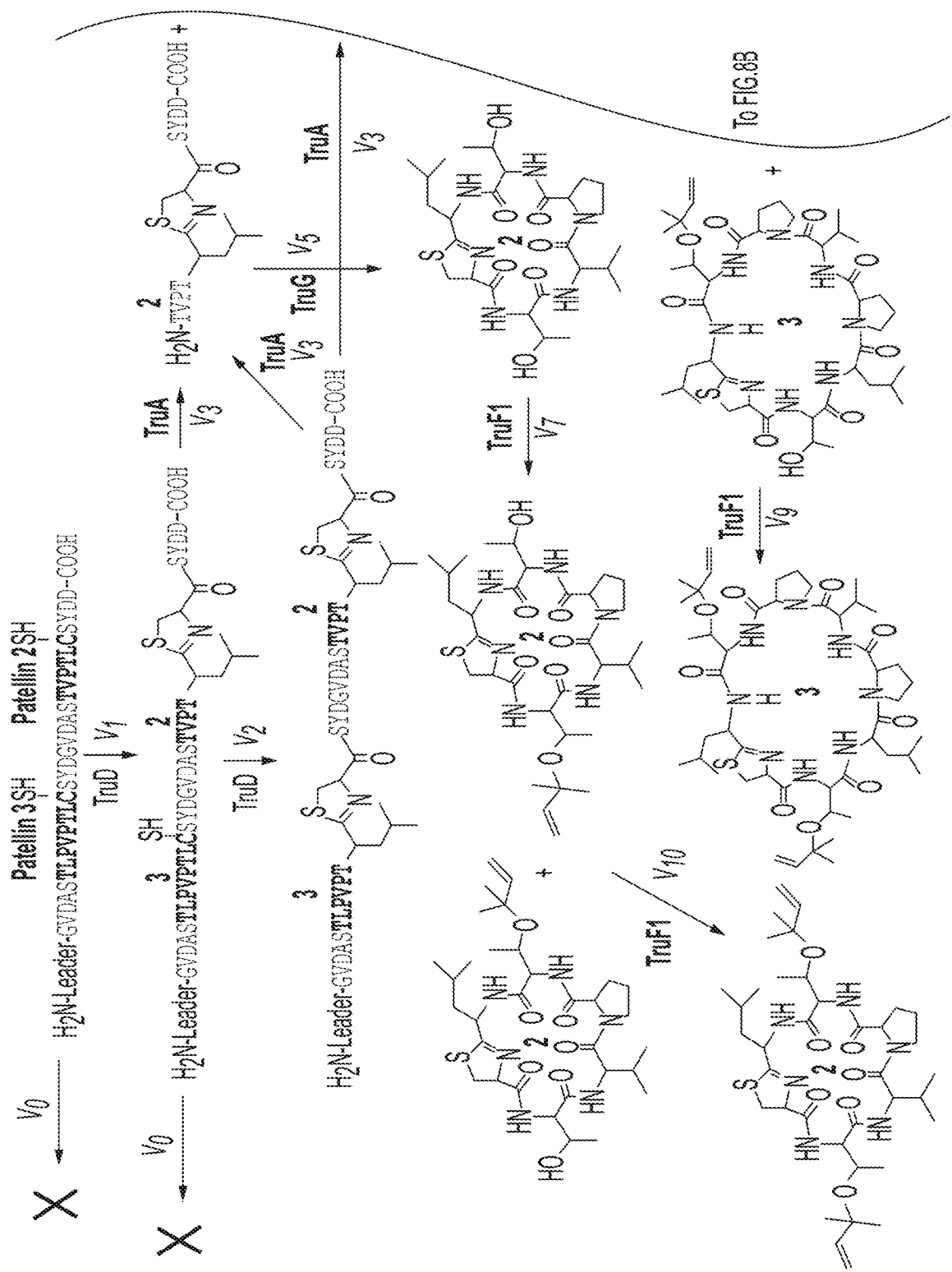
FIG. 8A and FIG. 8B show a simplified metabolic model for cyanobactin RiPP production in *E. coli*. X indicates degradation via unknown pathways.
Figure 8B:
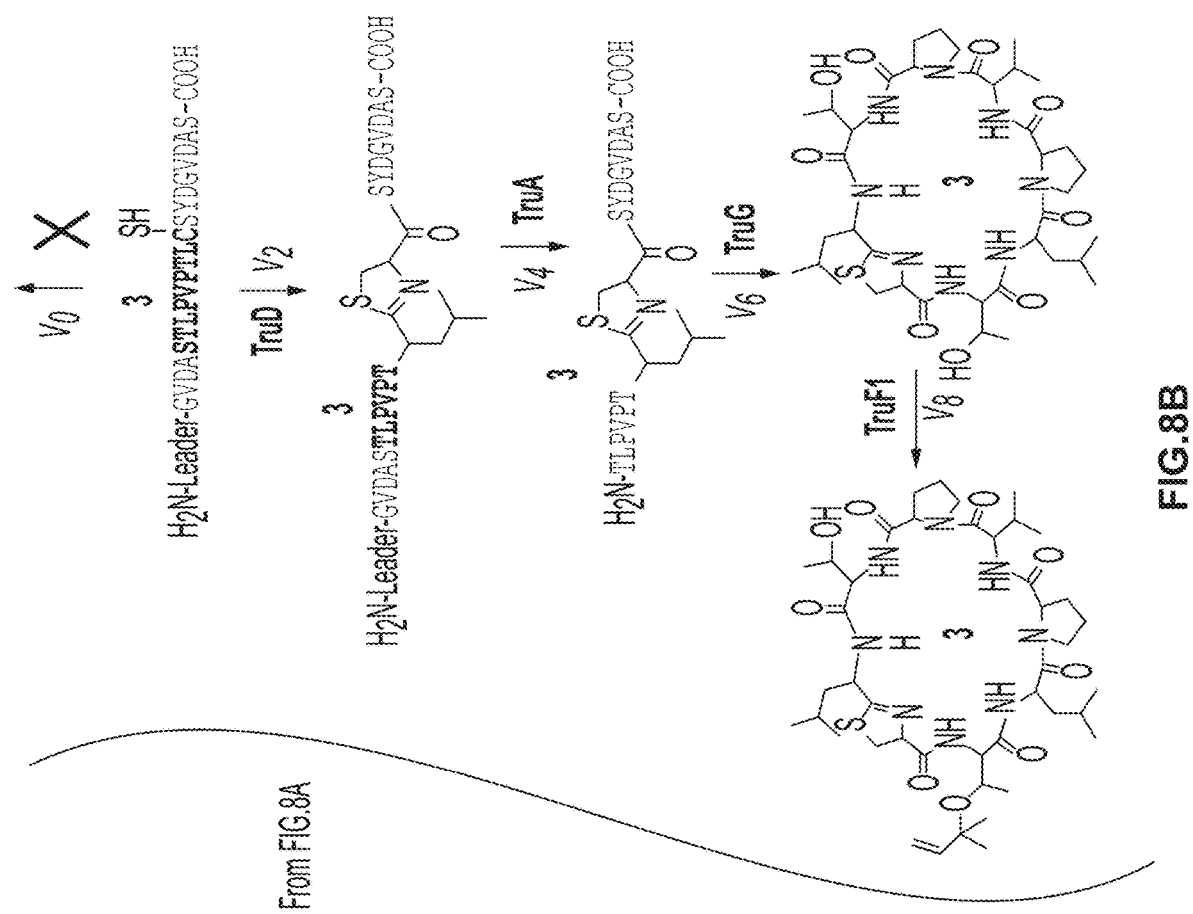

The tru cyanobactin pathway proteins (tru proteins) include TruA, TruB, TruC, TruD, TruE, TruF1, TruF2, and TruG. In tru, the first step is the ribosomal synthesis of the precursor peptide, TruE, which allows the production of one or more different RiPP products (see FIG. 1 and FIG. 8). Different TruE variants can be used, encoding different RiPP products ("X" in FIG. 1). TruE is the substrate for heterocyclase TruD, which inserts heterocycles, and TruA, a leader protease that removes the leader sequence. The product of TruA activity is the substrate of macrocyclase protease TruG, which macrocyclizes the N-C termini. Finally, prenyl transferase TruF1 installs one or more isoprene units on the mature macrocycle.

The pat cyanobactin pathway proteins (pat proteins) include PatA, PatB, PatC, PatD, PatE, PatF, and PatG. In pat, the first step is the ribosomal synthesis of the precursor peptide, PatE, which encodes the production of one or more different RiPP products (see FIG. 1 and FIG. 8). Different PatE variants can be used, encoding different products ("X" in FIG. 1). PatE is the substrate for heterocyclase PatD, which inserts heterocycles, and PatA, a leader protease that removes the leader sequence. The product of PatA activity is the substrate of macrocyclase protease PatG, which macrocyclizes the N-C termini.

The nucleic acid introduced into the cell may encode at least one tru protein, at least one pat protein, or a combination of at least one tru protein and at least one pat protein. For example, the nucleic acid may encode TruA, TruB, TruC, TruD, TruE, TruF1, TruF2, and TruG. In another example, the nucleic acid may encode TruA, TruD, TruE, TruF1, and TruG. In another example, the nucleic acid may encode PatA, PatB, PatC, PatD, PatE, PatF, and PatG. In still another example, the nucleic acid may encode TruA, TruB, TruC, TruD, TruE, TruF1, and PatG. Any combination of tru and pat genes or subset of tru and pat genes may be used, and the genes used may permit RiPP biosynthesis. In addition, the tru and/or pat genes introduced into the cell may be provided on a single nucleic acid or on one or more separate nucleic acids.

The tru and pat enzymes have relaxed substrate specificity. The pat pathway is similar to tru; most enzymes are nearly sequence identical between the pathways. The major biochemical difference is that pat does not use isoprene. In both cases, at each ensuing biochemical step the substrates are increasingly different. This is because early substrates contain large conserved elements known as "recognition sequences", which are progressively pared away in the course of biosynthesis and are not found in the products of the pathway. Thus, late-stage enzymes encounter structurally divergent substrates, while the substrates of early-stage enzymes are more similar to each other. A RiPP leader protease may be TruA or PatA; a RiPP heterocyclase may be TruD or PatD; a RiPP macrocyclase may be TruG or PatG; a RiPP prenyl transferase may be TruF1; a RiPP heterocyclase substrate may be TruE, PatE, a TruE variant, or a PatE variant.

In addition, the disclosed methods may include introducing into a cell a nucleic acid that encodes at least one mev protein. The mev proteins convert mevalonic acid to dimethylallyl diphosphate (DMAPP), which in turn is a substrate for prenyl transferase TruF1. The mev proteins include ERG12, ERG8, and MVD1. Additional mev proteins may include isopentenyl diphosphate isomerase (encoded by idi) and may also include farnesyl diphosphate synthase (encoded by ispA). Isopentenyl pyrophosphate (IPP) may be produced as an intermediate in the conversion of mevalonic acid to DMAPP. The mev genes introduced into the cell may be provided on a single nucleic acid or on one or more separate nucleic acids.

Nucleic acids encoding proteins such as tru, pat, or mev proteins may be introduced into a cell in any manner known to those of ordinary skill in the art. For example, such a nucleic acid may be introduced as part of a vector such as a plasmid, phage, transposon, cosmid, chromosome, artificial chromosome, virus, or virion. The nucleic acid may be capable of replication, and the nucleic acid may contain one or more regulatory elements capable of regulating transcription or translation of a gene in the cell. For example, the nucleic acid may include a constitutive promoter or an inducible promoter. The nucleic acid may include one or more selection markers. The one or more selection markers may be a positive selection marker, a negative selection marker, or a combination thereof. The nucleic acid may be introduced into the cell by any mechanism known to those of ordinary skill in the art, such as, for example, transfection, electroporation, microinjection, and the like. Once introduced into the cell, the nucleic acid may be extrachromosomal or may be integrated into an endogenous chromosome in the cell.

In some embodiments, the nucleic acid may be codon optimized for expression in the cell, according to methods familiar to those of ordinary skill in the art.

b. Cell

As described above, a nucleic acid is introduced into the cell. The cell may be a bacterial cell, a yeast cell, an insect cell, or a mammalian cell. The cell may be *Escherichia coli*. In some embodiments, the cell may be *E. coli* of strain K, for example, DH1, DH5-α, or DH10B, among others. Introduction of one or more nucleic acids into a cell may yield a recombinant cell.

In some embodiments, the recombinant cell may comprise a nucleic acid encoding at least one tru protein, a nucleic acid encoding at least one pat protein, or a nucleic acid encoding a combination of at least one tru protein and at least one pat protein. In some embodiments, the recombinant cell may comprise a nucleic acid encoding at least one tru protein and a nucleic acid encoding at least one mev protein, a nucleic acid encoding at least one pat protein and a nucleic acid encoding at least one mev protein, or a nucleic acid encoding a combination of at least one tru protein and at least one pat protein and a nucleic acid encoding at least one mev protein.

c. Cell Cultures

The disclosed methods may include culturing a recombinant cell. The cell may be cultured under conditions sufficient to promote cell growth and replication, using media and conditions familiar to those of ordinary skill in the art. In some embodiments, the recombinant cell may be cultured in the presence of an exogenous sulfide source. The exogenous sulfide source may be, for example, provided by culturing the cell in a medium comprising an exogenous sulfide source, bubbling an exogenous sulfide source into a medium, or providing the exogenous sulfide source via an external slow-release solution. The exogenous sulfide source may comprise cysteine, cystine, hydrogen sulfide, sodium hydrosulfide, sodium sulfide, a polysulfide, an inorganic sulfide, a metal-sulfur complex, or an organic sulfide. In embodiments in which the exogenous sulfide source comprises cysteine provided in the medium, the cysteine may be provided at a concentration of 0.1-100 mM, 0.5-40 mM, 1-50 mM, 2-20 mM, or 5-10 mM. The cysteine concentration in the medium may be, for example, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 20 mM, about 30 mM, about 40 mM, or about 50 mM.

In some embodiments, the recombinant cell may be cultured in the presence of exogenous mevalonate. The exogenous mevalonate may be, for example, provided by culturing the cell in a medium comprising exogenous mevalonate. The mevalonate may comprise mevalonic acid, or any mevalonate salt, such as, for example, a mevalonate lithium salt. In embodiments in which the exogenous mevalonate is provided in the medium, the mevalonate may be provided at a concentration of 0.1-100 mM, 1-50 mM, 5-40 mM, or 10-30 mM. The mevalonate concentration in the medium may be, for example, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 35 mM, about 40 mM, about 50 mM, about 75 mM, or about 100 mM.

In some embodiments, the recombinant cell may be cultured in the presence of an exogenous sulfide source and exogenous mevalonate.

d. RiPP Expression by a Recombinant Cell

In some embodiments, culturing a recombinant cell as described above may result in production of one or more RiPP products with high yield. In some embodiments, the disclosed methods and recombinant cells may yield a RiPP product in an amount of at least about 100 µg/L, at least about 200 µg/L, at least about 300 µg/L, at least about 400 µg/L at least about 500 µg/L, at least about 600 µg/L, at least about 700 µg/L, at least about 800 µg/L, at least about 900 µg/L, at least about 1 mg/L, at least about 5 mg/L, at least about 10 mg/L, at least about 15 mg/L, at least about 20 mg/L, at least about 25 mg/L, at least about 27 mg/L, at least about 30 mg/L, at least about 35 mg/L, or least about 40 mg/L.

3. METHODS FOR CELL-FREE RiPP PRODUCTION

Also provided herein are cell-free methods for producing a RiPP in vitro. In some embodiments, at least one tru protein, at least one pat protein, or a combination of at least one tru protein and at least one pat protein is combined with a RiPP heterocyclase substrate to produce a mixture. The mixture may be incubated under conditions sufficient to yield a RiPP product. In some embodiments, the RiPP heterocyclase substrate may be TruE, PatE, a TruE variant, or a PatE variant. In some embodiments, the mixture may further comprise at least one mev protein. In some embodiments, the mixture may comprise ERG12, ERG8, and MVD1.

In some embodiments, the mixture may comprise an exogenous sulfide source. In some embodiments, the mixture may comprise exogenous mevalonate.

4. RiPP LIBRARIES

The disclosed methods and recombinant cells may also be used to generate RiPP libraries. A library of nucleic acids encoding variant RiPP heterocyclase substrates may be produced by methods familiar to those known in the art. For example a nucleic acid may be prepared for directional cloning by treatment with two different endonucleases, and a library of synthetic dsDNA may be produced, each encoding a different RiPP heterocyclase precursor peptide sequence. The library of synthetic dsDNAs may be cloned into the nucleic acid and then introduced into the cell, yielding a library of recombinant cells comprising nucleic acids encoding millions of different variant RiPP heterocyclase substrates capable of yielding millions of different RiPP products.

5. EXAMPLES

The present invention has multiple aspects, illustrated by the following non-limiting examples.

Example 1

Materials and Methods for Subsequent Examples

Plasmids. Plasmids pTru-SD and the pTru-c1-c2 series contained the tru operon in a pUC19-based backbone. Genes were codon-optimized for expression in *E. coli*, while intergenic sequences are cyanobacterial. pTru-SD contained the precursor peptide gene TruE2, which encodes for patellin 3 and patellin 2 in the core peptides and is herein referred to as TruE-3-2 based upon the order of patellins in the precursor peptide. pTru-c1-c2 series plasmids contained unique restriction sites flanking the core peptide-coding sequences. Variations in the core peptides were made by ligating short pieces of DNA, made from overlapping primers, into these sites. These plasmids and the encoded core peptides are denoted in the text by the encoded products, e.g. "pTru-patellin2-trunkamide" ("pTru-2-T") refers to the version of the plasmid encoding amino acids TVPTLP in the first cassette and TSIAPFC in the second cassette. pTru-patellin2-patellin2 (pTru-2-2) was further modified to make pTru-his by insertion of a 6-histidine tag at the N-terminus of truE or in the truE leader sequence. TruE genes with his-tags were obtained as gBlocks from IDT (Coralville, Iowa).

pPat and pTru-b contain cyanobactin pathways in the plasmid backbone from the previously described tru expression vector Topo-E1-S316 f. pPat (pat) contains the patellamide pathway with genes codon-optimized for *E. coli* and intergenic sequences from the native cyanobacterium. The pathway was assembled from gBlocks.

For truF knockout experiments, pTru-b was made from Topo-E1-S31. Donia M S, Ravel J, & Schmidt E W (2008), A global assembly line for cyanobactins. Nature Chemical Biology 4(6):341-343. truE, truF1 and truF2 were replaced by sequences that were codon-optimized for expression in *E. coli*. This plasmid was assembled by recombination in *Saccharomyces cerevisiae* BJ4741. To remove truF1, the entire pathway, except for truF1, was amplified by PCR in two pieces with overlapping ends, such that truF1 and 18 base pairs in front of the gene were cleanly removed. The first piece consisted of half of the plasmid backbone and the first part of the tru pathway (truA-E, most of the truE-truF1 intergenic sequence). The second piece contained the end of the tru pathway (truF1-truF2 intergenic sequence, truF2 and truG) and the other half of the plasmid backbone. Gibson assembly was used to ligate the two PCR products. Gibson D G (2011), Enzymatic assembly of overlapping DNA fragments, *Methods in Enzymology* 498:349-361. truF2 and double knockout plasmids were made by the same strategy. In the truF2 knockout plasmid, the entire truF1-truF2 intergenic sequence was removed. The double knockout plasmid is missing eighteen base pairs before truF1, both genes, and the intergenic region between them.

Plasmid Topo-E1-S316-GFP-F4 was described previously. Donia M S, Ruffner D E, Cao S, & Schmidt E W (2011), Accessing the hidden majority of marine natural products through metagenomics, *ChemBioChem,* 12(8): 1230-1236. This plasmid contains the tru pathway with gfp fused directly to the end of truG. All pathways were under the control of lac promoter and expressed constitutively in DH10B cells.

pMEVB, pMBI, and pMBIS, containing the second half of the mevalonate pathway were obtained from Addgene (plasmids 17819, 17816, and 17817, respectively). pMEVB contains ERG12, ERG8, MVD1; pMBI has the pMEVB genes but with idi appended after MVD1; pMBIS is pMBI with additional ispa. Martin V J, Pitera D J, Withers S T, Newman J D, & Keasling J D (2003), Engineering a mevalonate pathway in *Escherichia coli* for production of terpenoids, *Nature Biotechnology* 21(7):796-802. Empty plasmid pBBR with a modified multiple cloning site was constructed from pMBI. pMBI was digested with KpnI and SacI. The vector backbone piece was ligated with a small piece of DNA constructed from overlapping primers to create an expanded multiple cloning site (forward: 5' AGTGTACAGGGCCCCCCCTCGAGGGTATCGA-TAAGCTTGATATCGAATTCCTGCA GTAGGAGGAAT-TAACCCATATGTC (SEQ ID NO: 8), reverse: GAT-GAGCTCCACCGCGGTGGCGGCCGCTCTAGAAC-TAGTGGATCCCCCGGGTAC CATGGACATATGGGT-TAATTCCTC (SEQ ID NO: 9)).

roGFP2 was prepared as described. Hanson G T, et al. (2004), Investigating mitochondrial redox potential with redox-sensitive green fluorescent protein indicators, *J. Biol. Chem.,* 279(13):13044-13053. roGFP2 was cloned into NdeI and KpnI sites of the previously described pRSF-DlacI-Iacp vector. Donia M S, Ruffner D E, Cao S, & Schmidt E W (2011), Accessing the hidden majority of marine natural products through metagenomics, *ChemBioChem,* 12(8): 1230-1236. The result was to make pRSFlac-roGFP2, placing roGFP2 under control of the lac promoter.

pTARA was a gift from Kathleen Matthews (Addgene plasmid #31491). Wycuff D R & Matthews K S (2000), Generation of an AraC-araBAD promoter-regulated T7 expression system, *Analytical Biochemistry,* 277(1):67-73. pET-TruE2 contained truE2, encoding patellins 2 and 3, in pET28, under control of a T7 promoter. To make pTruA, pTru-b was digested with XhoI and re-ligated to remove the portion of the tru from the end of truB to truG, including the last 52 base pairs of truB.

All vectors were partially sequenced after construction, to confirm that the pieces had been ligated correctly.

TABLE I

Plasmids

| Plasmid | Source | Details |
|---|---|---|
| pTru-SD | Symbion Discovery | Tru pathway expression plasmid with codon-optimized genes, encodes patellins 2 and 3, under control of the lac promoter |
| pTru-c1-c2 | Cloned for this study | Tru pathway expression plasmids with codon-optimized genes, this set of plasmids encodes various combinations of patellin 2, patellin 3 and trunkamide, under control of the lac promoter |
| pTru-his-int | Cloned from pTru-patellin 2-patellin 2 and gBlock | Tru pathway expression plasmid encoding his-tagged TruE with sequence MNKKNILPQLGQPVIRLTGGSHHHHHHSGAGQLSSQL AELSEEALGGVDASTVPTLCSYDGVDASTVPTLCSYDD (SEQ ID NO: 10), under control of the lac promoter |
| pTru-his-N-term | Cloned from pTru-patellin 2-patellin 2 and gBlock | Tru pathway expression plasmid encoding his-tagged TruE with sequence MGSSHHHHHHSGGMNKKNILPQLGQPVIRLTAGQLSS QLAELSEEALGGVDASTVPTLCSYDGVDASTVPTLCSYD D (SEQ ID NO: 11), under control of the lac promoter |
| pPat | Assembled from gBlocks | Pat pathway expression plasmid with codon-optimized genes, encodes patellamides A and C, under control of the lac promoter |
| pTru-b | Made from Topo-E1-S316 (1) and gBlocks | Tru pathway expression plasmid with codon-optimized truE, truF1, and truF2, under control of the lac promoter |
| pTru-DF1 | Made from pTru-b | Tru pathway expression plasmid missing truF1 and eighteen base pairs upstream of the truF1 gene |
| pTru-DF2 | Made from pTru-b | Tru pathway expression plasmid missing truF2 and the F1-F2 intergenic sequence |

TABLE I-continued

Plasmids

| Plasmid | Source | Details |
|---|---|---|
| pTru-DF1F2 | Made from pTru-b | Tru pathway expression with a deletion from eighteen base pairs before truF1 to the end of truF2 |
| Topo-E1-S316-GFP-F4 | Donia, et al., ChemBioChem, 12(8):1230-36 (2011) | Tru pathway expression plasmid with gfp fused to the end of truG |
| pMEVB | Addgene plasmid 17819 | Expression plasmid for the second half of the mevalonate pathway, under control of lac |
| pMBI | Addgene plasmid 17816 | Expression plasmid for the second half of the mevalonate pathway with idi |
| pMBIS | Addgene plasmid 17817 | Expression plasmid for the second half of the mevalonate pathway with idi and ispa |
| pBBR1-MCS3 | Made from pMBI | Backbone for plasmids pMEVB, pMBI, pMBIS; made by removing mevalonate pathway genes from pMBI |
| pRSFlac-roGFP2 | Made from pRSF-DlacI-lacp and roGFP2 | Expression plasmid with redox-sensitive GFP under control of the lac promoter |
| pTARA | Addgene plasmid 31491 Wycuff and Matthews, Analytical Biochemistry, 277:67-73 (2000) | T7 RNA polymerase gene under control of the AraC-araBAD promoter |
| pET-TruE2 | McIntosh, et al., Journal of the American Chemical Society, 132:4089-91 (2010) | truE2 under control of a T7 promoter |
| pTruA | Made from Topo-E1-S316 | Expression vector for TruA and part of TruB, under control of the lac promoter |
| pET28(b) | Novagen | Backbone used for pET-truE2 |

Chemicals and other materials. L-cysteine hydrochloride was obtained from Amresco (Solon, Ohio). Ampicillin, kanamycin, tetracycline and diamide were obtained from Sigma-Aldrich (St. Louis, Mo.). Dithiothreitol was obtained from Goldbio (St. Louis, Mo.). 2xYT medium was obtained in solid form from growcells.com. All solvents used for silica open column chromatography, HPLC, and HPLC/MS analyses were obtained from Fisher Scientific (Pittsburg, Pa.). *Lissoclinum patella* samples that were used for isolation of authentic standards of patellins 2 and 3 were collected in Papua New Guinea with proper collection permits.

General experimental design for expression studies in *E. coli*. Many experiments described herein employ *E. coli* cells that produce cyanobactin RiPPs. All such experiments described in this manuscript were performed a minimum of 4 times with at least n=2 technical replicates per run. In these experiments, cells were initially grown in at least duplicate, with simultaneous runs controlling for conditions (for example, 2 flasks containing *E. coli* expressing cyanobactins with cysteine; 2 flasks with the same conditions but lacking cysteine). Cyanobactin production was measured in one set of HPLC-MS experiments with wash and control steps before and after experimental runs. Subsequently, conditions were further examined in at least one further replicate, but in several cases, many more. For example, the initial observation that cysteine increased yield has been repeated in >100 biological replicates. Finally, the figures shown in this study were made using optimized protocols derived from these early studies and use n=3 or n=4 with simultaneously performed controls that also used n=3 or n=4.

Early optimization of fermentation protocol. The extensive use of many different promoters and plasmid constructs to optimize the pat and tru pathways has been described. Donia M S, Ruffner D E, Cao S, & Schmidt E W (2011), Accessing the hidden majority of marine natural products through metagenomics, *ChemBioChem*, 12(8):1230-1236. In addition, media was optimized, with best results obtained using 2xYT (either purchased as the mixture from growcells.com or made using individually purchased ingredients from Difco (Becton, Dickinson and Company, Franklin Lakes, N.J.). Based upon these results, the inventors chose to leave tru and pat in their native operon structures with the native intergenic elements for the following exemplary experiments described, since under no condition improved production of cyanobactins observed when altering promoter structure. However, the lac promoter was placed at the start of the operon, and the genes themselves were codon optimized for *E. coli* translation. The resulting vectors, pTru-SD and pPat, exhibited optimal production of cyanobactins and were used in this study. In all cases, production of compounds was directly measured using the HPLC-MS technique described in detail below.

Using pTru-SD, fermentation vessels and conditions were explored by using vessels of different sizes, including test tubes and 25, 50, 100, 250, 1000, and 2500 mL (Fernbach) flasks. The use of fermenters at 1.5 and 14 L scales were attempted under various media and conditions. Production on agar plates was also measured using various media. The inventors found that production of compounds did not scale with vessel size, and that the optimum production per volume of media was obtained in test tubes. Therefore, the inventors moved to deep-well (10 mL), 24-well plates for production. These plates contained 2xYT media (6 mL) and were sealed on top with foil. Above each well, a small hole was pierced using a toothpick.

Timing of production was measured daily from 1-7 days. The best reproducible production of compounds was achieved after 5 days, although in some individual experiments 3 days was sufficient. After 5 days, compound degradation was observed. With this optimal condition in hand, the effect of shaking rate and temperature was once again established, leading to the condition described under "Growth conditions and compound expressions" below. Using these conditions, yield of cyanobactins was improved to 10 µg/L.

Cysteine as a novel agent affecting cyanobactin production. To further improve the yield, an empirical approach was adopted. Using 24-well plates, 2 types of media were investigated: rich medium 2xYT and the defined medium F1. Pfeifer B, Hu Z, Licari P, & Khosla C (2002), Process and metabolic strategies for improved production of *Escherichia coli*-derived 6-deoxyerythronolide B, *Applied and Environmental Microbiology*, 68(7):3287-3292. Twelve conditions were defined for each medium, in which the following were added to 2xYT and F1: 1) no additives; 2) 0.1% fucose/0.3% arabinose; 3) 0.05% glucose; 4) 0.3% lactose; 5) 0.5% glycerol; 6) 17 amino acids (-Met/Cys/Tyr) 10 mM each; 7) Fe(II) 1 mM; 8) Cu(II) 1 mM; 9) Zn(II) 1 mM; 10) Mn(II) 1 mM; 11) Met/Cys 30 mM each; 12) FMN 100 µM. In addition, to provide a carbon source for F1 media, 0.2% maltose was added to condition 1 and 0.5% glycerol was added to conditions 3 and 7-12. Apparent increases were observed in F1 with conditions 6, 11, and 12, while with 2xYT increase was only observed with condition 11. In the next round of experiments, F1 media was used at 100 mL scale using 4 different combinations containing additives 6, 11, and 12, and 2.5 L Fernbach scale with condition 6; with 2xYT, 2.5 L Fernbachs were used with condition 11. Only condition 11 with 2xYT provided reproducible, robust yield, while the other conditions were not confirmed to provide improved yield. Finally, individual 2xYT experiments were carried out containing only 30 mM cysteine or 30 mM methionine; these showed that cysteine and not methionine was responsible for the observed yield increase. A series of conditions of added cysteine was used, from 1-50 mM. In all conditions up to 30 mM, improved cyanobactin production was observed. Above 30 mM, no cyanobactins were observed. The optimum condition in 24-well plates employed 5 mM cysteine, while in some experiments 10 mM cysteine was optimal.

Growth conditions and compound expressions. Plasmids containing the tru or pat pathway were transformed alone or co-transformed with pRSFlac-roGFP2, pBBR, pMEVB (mevb), pMBI (mbi), or pMBIS (mbis). Martin V J, Pitera D J, Withers S T, Newman J D, & Keasling J D (2003), Engineering a mevalonate pathway in *Escherichia coli* for production of terpenoids, *Nature Biotechnology* 21(7):796-802. Single colonies were inoculated into liquid 2xYT broth (6 mL) in 24-well deep-well plates with the addition of appropriate amounts of antibiotics (ampicillin: 50 µg/mL, kanamycin: 50 µg/mL, tetracycline: 5 µg/mL), and grown overnight. Growing seed cultures (0.2% v/v) were combined and inoculated into fresh medium containing antibiotics described above. In some experiments, growing seed cultures were supplemented with 20% (v/v) glycerol and stored at −80° C. These glycerol stocks were used to inoculate expression cultures in order to provide consistent starting conditions for several sets of experiments. Cysteine (5 mM unless otherwise indicated) was added upon inoculation of expression cultures. Mevalonolactone (Sigma-Aldrich, St. Louis, Mo.) was hydrolyzed to mevalonate according published methods, Martin V J, Pitera D J, Withers S T, Newman J D, & Keasling J D (2003), Engineering a mevalonate pathway in *Escherichia coli* for production of terpenoids, *Nature Biotechnology*, 21(7):796-802, and was also added to the expression cultures in some experiments at inoculation (5, 10, 20, 40 mM final concentrations). The cultures were allowed to shake at 150 rpm, 30° C. for 5 days after which the cells were harvested by centrifugation at 4000 rpm, washed with saline solution (0.1 M NaCl) or phosphate-buffered saline (PBS) solution (137 mM NaCl, 2.7 mM KCl, 10 mM $Na_2HPO_4$, 2 mM $KH_2PO_4$), and extracted with acetone (2 or 4 mL). The acetone extracts were then dried to yield the organic extracts for each 6 mL culture. In labeling experiments, $^{13}C$ mevalonate (1 mM) (Sigma-Aldrich, St. Louis, Mo.) was added at the beginning of the expressions as described above.

To measure growth during some experiments, samples were withdrawn from cultures at time points indicated in figures, and OD600 was measured in 96-well plates on a microplate reader (Molecular Devices, Sunnyvale Calif.) or in 1 cm cuvettes on a Cary UV-visible spectrophotometer (Agilent Technologies, Santa Clara, Calif.). Culture samples were diluted as necessary in 2xYT medium for accurate readings.

Chloramphenicol addition experiments. Cultures were grown using the standard procedures described above in 24-well plates. Chloramphenicol (50 µg/L) was added to selected wells at 24, 48, 72, and 96 hours post-inoculation. At 120 hours post-inoculation, all cultures, including positive controls (0 µg/L chloramphenicol) were harvested and analyzed for cyanobactin RiPP production. Growth under each condition was measured by taking aliquots at the 24 hour time points and measured as described above.

Measurement of cellular redox state with roGFP2. DH10-beta *E. coli* was transformed with pTru-SD and pRSFlac-roGFP2, and was grown as described above. Cultures were grown with and without supplementation with 10 mM cysteine. At each time point, OD600 was measured and for each sample the culture volume needed to give OD600=6 when re-suspended to 200 µL was harvested by centrifugation. Each cell pellet was suspended in PBS (200 µL) with 10% (v/v) glycerol, divided to two wells of a 96-well plate and stored at −80 degrees C. All samples (over several days) were collected in one plate, which was carefully kept frozen during the addition of new samples. Fluorescence was read with excitation wavelengths of 400 and 490 nm (520 nm emission). Dithiothreitol (DTT; 5 mM) was added to one well from each sample, and diamide (5 mM) was added to the other well. After 30 min incubation at room temperature, the plate was read again. DTT and diamide addition and incubation were repeated and the plate was read again to make sure roGFP2 was fully oxidized and reduced. The fraction of roGFP2 that was reduced in each sample was calculated as the $Em_{490}$ fluorescence difference between the freshly thawed sample and the sample once fully reduced, divided by the difference between fully oxidized and fully reduced sample. The expression of roGFP2 as the main fluorophore in these samples was confirmed by measuring absorption and emission spectra of fully reduced and fully oxidized samples. Additionally, cells from some roGFP2 expression cultures were lysed, and cell-free extracts were subjected to native polyacrylamide gel electrophoresis. Fluorescence in this gel was analyzed using an Odyssey Fc Imager (Li-COR, Lincoln, Nebr.).

Total GFP measurement (not redox). To measure GFP expression with and without added cysteine, cultures with Topo-E1-S316-GFP-F4 were grown as described in the Growth conditions and compound expressions section. Half of the cultures were supplemented with cysteine (10 mM). At each time point, OD600 was measured from four cultures with and four cultures without cysteine. Culture volumes equivalent to 2 mL of OD600 =1 were centrifuged at 16,100×g, and each cell pellet was suspended in 200 μL PBS with 10% (v/v) glycerol and divided into two wells of a 96-well plate (33 μL in one well, 167 μL in the other well). The 96-well plate was kept frozen during addition of each new set of samples. At the end of the experiment, the plate was thawed and fluorescence with excitation at 400 nm and emission at 510 nm was measured.

Cyanobactin RiPP expression under sulfide. To test the effect of sulfide on tru expression, cultures with pTru-SD were grown in glass culture tubes inside closed 50 mL conical tubes. The conical tubes were prepared with a sodium sulfide solution in phosphate buffer outside of the culture tube, so that $H_2S$ from the buffer solution equilibrated through the headspace with the culture in the glass tube. The amount of sulfide in the headspace of each culture (and therefore the concentration in each culture) should depend on the $Na_2S$ concentration and pH of the phosphate buffer, depending on eq. 1 and eq. 2 below.

$$H^+ + HS^- \leftrightarrow H_2S, pK_a = 7 \qquad \text{eq. 1}$$

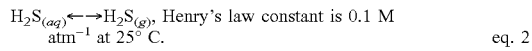
$$H_2S_{(aq)} \leftrightarrow H_2S_{(g)}, \text{Henry's law constant is } 0.1 \text{ M atm}^{-1} \text{ at } 25^\circ \text{ C}. \qquad \text{eq. 2}$$

Seed cultures of DH10B transformed with pTru-pat3-pat2 prepared as described above were used to inoculate a fresh culture in 2xYT medium. This was distributed to 10×75 mm glass culture tubes, 2 mL per tube. Each culture tube was placed in a sterile 50 mL conical tube that also contained 10 mL of potassium phosphate buffer (0.2 M) at pH 6.8, pH 7.8 or pH 8.8. $Na_2S$ was added to each falcon tube from a 1 M sterile solution immediately before closing the tube. The $Na_2S$ solution was added to the falcon tube in such a way that it mixed with the phosphate buffer only after the falcon tube was closed. Cultures were grown at 30° C. and 150 rpm for three days.

Anaerobic cyanobactin RiPP expression. Anaerobic cultures with pTru-SD were similar to sulfide cultures described above. 50 mL conical tubes were prepared with buffer and glass culture tubes. The buffer in each conical tube was 0.2 M KPi, pH 8.0. In this set of experiments, the conical tubes were sealed with large red rubber sleeve stoppers. Cultures for anaerobic growth were then purged with argon gas for 45 minutes before cultures were added using a needle and syringe.

All cultures were supplemented with $NaMoO_4$ (10 μM). One set of cultures was grown on $O_2$ (not purged with argon). Anaerobic cultures were supplemented with DMSO (100 mM) or $NaNO_3$ (100 mM). For each growth substrate ($O_2$, DMSO or $NO_3^-$), cultures were grown with cysteine (5 mM added to the culture), $Na_2S$ (20 mM added to the buffer in the conical tube) or no addition of cysteine or sulfide. Cultures were grown at 30° C. and 150 rpm for five days.

Tru expression for western blotting, cysteine determination and cyanobactin determination. Two different his-tagged TruE constructs were used for western blotting experiments. In one set of experiments, pET-TruE was co-transformed with pTARA and pTruA, pTru-pat3-pat2, or pUC19. For negative controls, pET28(b) was used in place of pET-TruE. Six colonies from each transformation were grown overnight in 2xYT medium with kanamycin (50 μg/mL), chloramphenicol (25 μg/mL) and ampicillin (50 μg/mL). The seed cultures from each transformation were combined, supplemented with glycerol (15% (v/v)), aliquoted to microcentrifuge tubes, and stored at –80° C. For expression, a glycerol stock from each transformation was used to inoculate 150 mL 2xYT medium with the same antibiotics. These cultures were grown between room temperature and 30° C. to OD600=0.3 (cultures that grew faster were removed from the incubator to grow more slowly at room temperature, so that all cultures reached OD600=0.3 at around the same time). Arabinose (0.05%) was added to induce T7 RNA polymerase expression and cultures were distributed to 24-well plates, 6 mL per well to grow at 30° C., 150 rpm. Some wells were supplemented with cysteine (10 mM). Samples were taken during growth. An aliquot (10 μL) from each sample was diluted to 100 μL with PBS for OD600 determination in a 96-well plate. An aliquot (1 mL) from each sample was centrifuged for 3 minutes at 16,100× g. The spent medium from each sample was moved to a clean tube and stored at –20° C. for later cysteine assays. The cell pellet from each sample was suspended in PBS (100 μL) and stored at –20° C. for western blotting.

In the second set of experiments, cultures with pTru-his vectors were grown as described in the Growth conditions and compound expressions section. For negative controls, pTru-patellin 2-patellin 2 was used in place of pTru-his. At various times, OD600 was measured, and samples were saved for western blotting and cysteine determination as described above. Cell pellets from the remainder of each culture were saved for acetone extraction and LC/MS analysis for cyanobactins as described in the Growth conditions and compound expressions section.

Cysteine concentration. Cysteine concentrations were determined by reaction with ninhydrin[47]. Spent media samples were thawed and mixed by vortexing. Samples (45 μL) were mixed with a freshly-prepared dithiothreitol solution (5 μL, 1 M), glacial acetic acid (50 μL), and ninhydrin solution (50 μL; ninhydrin (250 mg) in concentrated HCl (4 mL) and glacial acetic acid (6 mL)), placed in a heat block at 100° C. for 10 minutes, cooled on ice, and then mixed with ethanol (500 μL). Absorbance at 560 nm was measured in 96-well plates on a microplate reader. Standards were prepared by adding cysteine from a 0.1 M stock to fresh 2xYT medium to concentrations between 0 and 3 mM, and were assayed with each batch of spent media samples. Spent media samples were diluted two-fold in fresh 2xYT as needed to bring their cysteine concentrations within the range of the standard curve.

Western blotting. Each 100 μL cell sample was supplemented with 20 μL of 6× SDS-PAGE loading dye (tris-HCl, pH 6.8 (50 mM), SDS (2% w/v), glycerol (10% v/v), dithiothreitol (50 mM) bromophenol blue (0.02% w/v)), vortexed, incubated at 55° C. for 30 minutes, vortexed again, and centrifuged at 16,100×g for 10 minutes. Supernatants from this procedure were separated by SDS-PAGE on 18% acrylamide gels. Loading volumes were normalized to load protein from approximately 80 μL of culture at OD600=1. After SDS-PAGE, proteins were blotted to 0.2 μm nitrocellulose membranes (Bio-Rad, Hercules, Calif.) at 30 V for 20 hours in a wet transfer apparatus in buffer containing tris base (25 mM), glycine (150 mM) and methanol (20% v/v).

After transfer, blots were washed for 5 minutes with TBS (50 mM tris-Cl, 150 mM NaCl, pH 7.5), blocked with 5% nonfat dry milk in TTBS (50 mM tris-Cl, 500 mM NaCl, pH 7.5, with 1% (v/v) Triton X-100 and 0.25% (v/v) tween 20), washed 4×5 minutes in TTBS, probed with mouse anti-his antibody (GE Healthcare Life Sciences, Pittsburgh, Pa., diluted 10 μL per 50 mL TTBS with 5% nonfat dry milk), washed 4×5 minutes in TTBS, probed with Goat anti-Mouse IgG (H+L) Cross Adsorbed Secondary Antibody, HRP conjugate (Thermo Fisher Scientific, Waltham, Mass., diluted 1 μL per 50 mL TTBS with 5% nonfat dry milk), washed 6×5 minutes in TTBS and rinsed with TBS. Blots were visualized with Amersham ECL Prime Western Blotting Detection Reagent (GE Healthcare Life Sciences) on a Bio-Rad ChemiDoc imaging system.

Isolation of patellin 2 from E. coli expressions. Overnight seed cultures of E. coli harboring tru/mbi were grown under appropriate antibiotic selection and inoculated into 1 L 2xYT broth with antibiotics, cysteine (5 mM), and mevalonate (10 mM). The broth was distributed into 24 well plates containing 6 mL per well and grown for five days at 30° C. while shaking at 150 rpm. The cultures were harvested as described above, and the cells were extracted repeatedly with acetone. The combined acetone fractions were dried and fractionated by silica open column chromatography using previously described gradient and methods. Tianero M D, Donia M S, Young T S, Schultz P G, & Schmidt E W (2012), Ribosomal route to small-molecule diversity, *Journal of the American Chemical Society* 134(1): 418-425. Fractions were analyzed by HPLC-MS for the presence of cyanobactins, and the compound containing fractions were subjected to reverse phase HPLC fractionation on an Eclipse XDB, 9.4×250 mm, 5 C18 column (Agilent Technologies, Santa Clara, Calif.) using the following solvent gradient: 5% B to 100% B (0-30 minutes), 100% B (30 to 40 minutes), and 100% to 5% B (40 to 45 minutes); Solvent B consisted of acetonitrile and solvent A consisted of water. A flow rate of 2.5 mL min$^{-1}$ was used. Patellin 2 was purified on a Luna, 4.6×250 mm, 5 μm C18 Column (Phenomenex, Torrance, Calif.) using the solvent gradient: 80% B to 94% B (0-15 minutes), 94% B (15-17 minutes), and 94% to 80% B (17-20 minutes), at a flow rate of 1 mL min$^{-1}$; Solvent B consisted of acetonitrile and solvent A consisted of water.

Figure 9A:
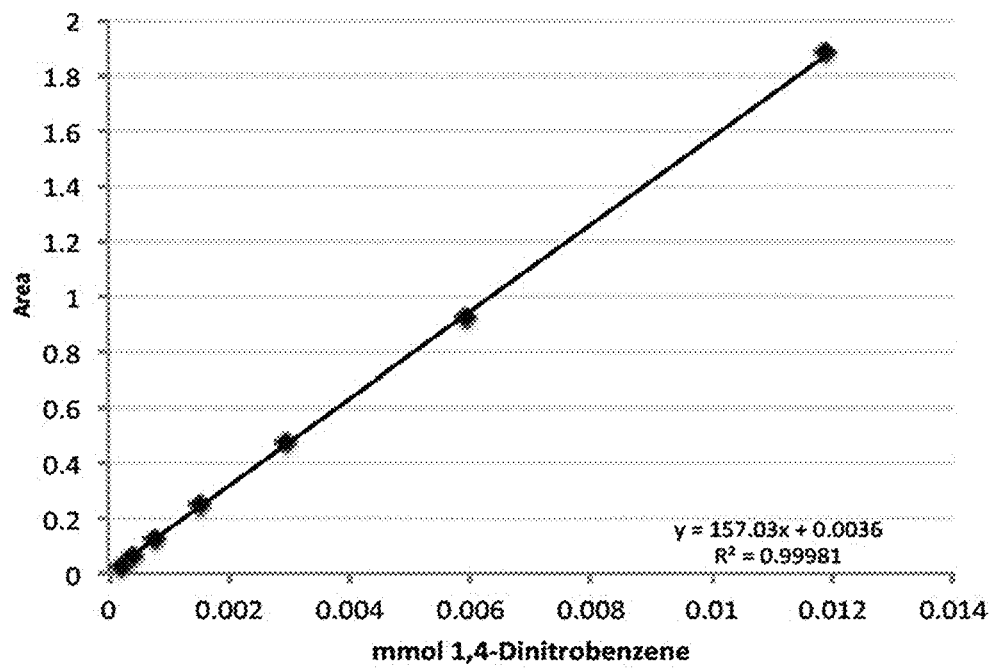
FIG. 9A shows peak areas of 1,4-dinitrobenzene measured by 1H NMR as described in the Methods. This curve was used to quantify the purified patellin 2 standards which were used for downstream LC/MS quantification.

Quantification by proton NMR. $^1$H NMR was used to quantify purified patellin 2. This information was used as the basis for the HPLC/MS calibration curve as well as for bioactivity assays. An external standard curve was made using the different amounts of 1,4-dinitrobenzene (Sigma-Aldrich, St. Louis, Mo.) using described methods. Briefly, two-fold dilutions (1.2 μM to 79.3 μM) of 1,4-DNB in DMSO-d6 (Cambridge Isotope Laboratories Inc., Tewksbury, Mass.) were prepared in uniform 3 mm Kontes precision NMR tubes (Sigma-Aldrich, St. Louis, Mo.). $^1$H NMR for each DNB sample was acquired on a Varian Inova 500 instrument (Agilent Technologies, Santa Clara, Calif.) with 32 scans using an 18 s relaxation delay (d1) as calculated from T1 using signal inversion (FIG. 9A). The integrals of the four DNB protons were obtained and used as the Y-values for the calibration curve. Patellin 2 was prepared using the same DMSO-d6. The $^1$H spectrum of patellin 2 was obtained using 32 scans and 4 s d1, which as determined as described above. Signals from a methyl protons of the valine residue were integrated and the values were compared with the external standards.

Figure 9B:
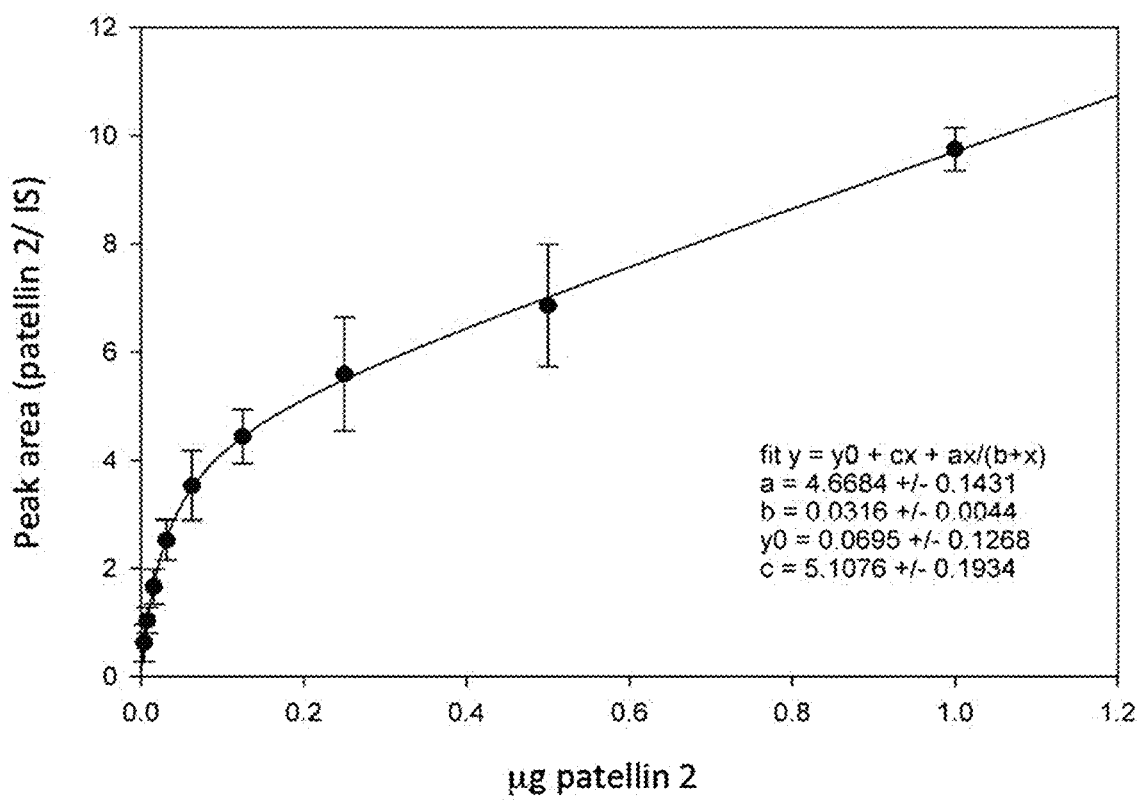
FIG. 9B shows a calibration curve of patellin 2 in the LC/MS. Different concentrations of patellin 2 were prepared in methanol and equal amount of the internal standard (IS), (0.5 µg/mL) was added to each solution. The ion chromatograms of both patellin 2 and the IS were integrated and the patellin 2 peak area was divided by the IS area in each sample concentration. Each point is the average of three separate measurements and the error bars show the standard deviation.
Figure 9C:
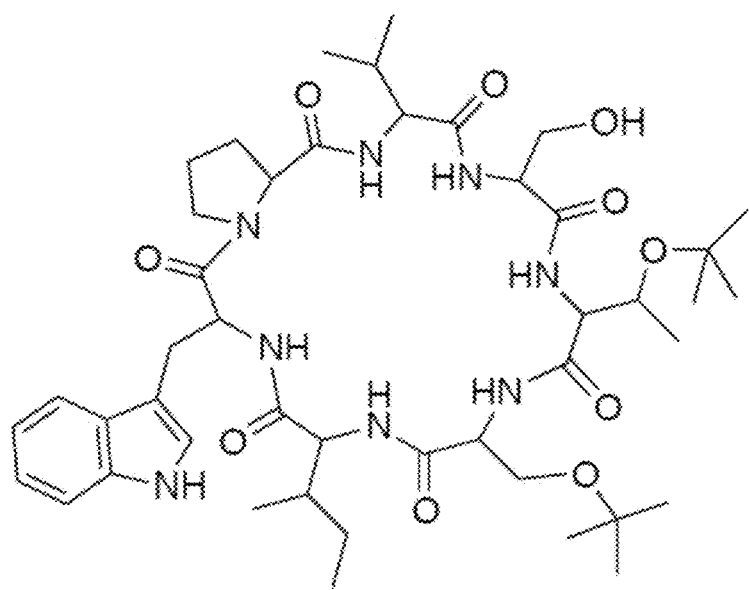
FIG. 9C is the structure of the internal standard e8.
Figure 10:
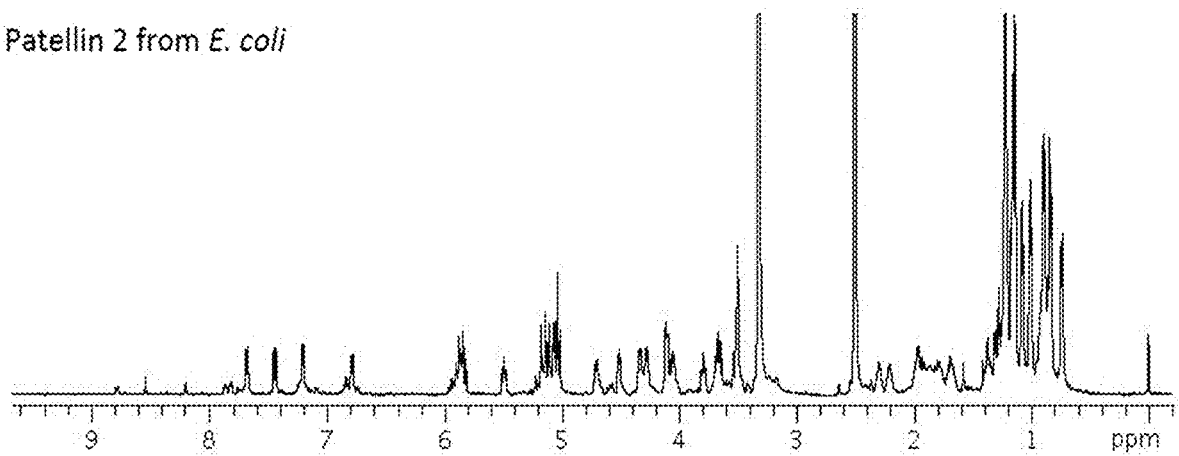
FIG. 10 shows 1H NMR of patellin 2 isolated from *L. patella* and *E. coli*.
Figure 10:
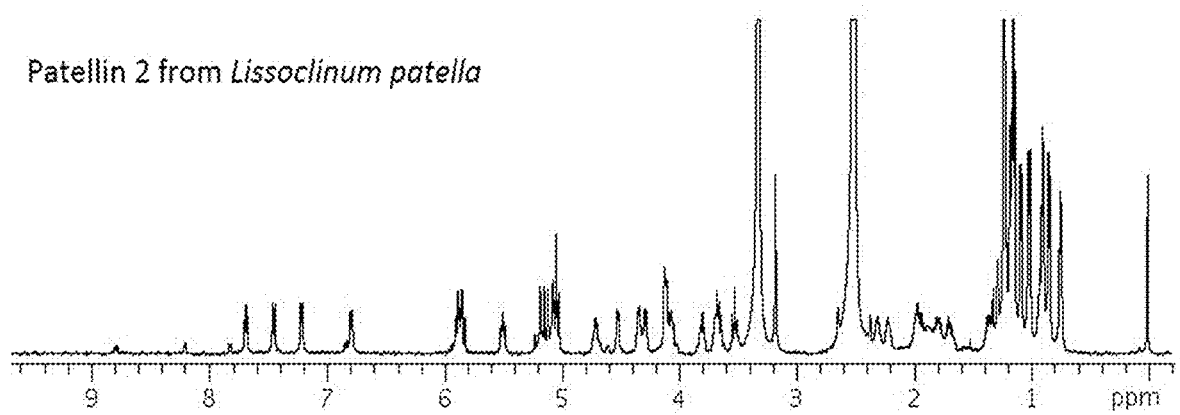

Quantification of cyanobactin RiPPs from different expressions using HPLC/MS. Extracts were dissolved in methanol (500 μL) and analyzed by HPLC-ESI-MS using a Waters Micromass ZQ mass spectrometer. Samples were injected at uniform volumes (40 μL). A synthetic heptapeptide (cyclo-VS(t-bu-Thr)(t-bu-Ser)IWP) was used as an internal standard in all HPLC/MS analyses. The extracts were analyzed on a Zorbax Eclipse Plus 4.6×150 mm, 5 μm, C18 column (Agilent Technologies, Inc., Santa Clara, Calif.) using the following solvent gradient: 10% B (0-2 minutes), 10% B to 100% B (2-20 minutes), 100% B (21 to 30 minutes), and 100% to 10% B (30 to 35 minutes). Solvent B consisted of acetonitrile with 0.05% (v/v) formic acid; solvent A consisted of water with 0.05% (v/v) formic acid. The peaks of interest were selected from the chromatograms and the resulting peak areas for each compound in the extract were obtained. The ratio of the peak area of the compound of interest to the peak area of the internal standard was then taken in each sample and the amount of each compound was calculated using the calibration curve that was generated using different concentrations of purified patellin 2 (FIG. 9). All expressions were done in triplicate. Around 70 independent expression experiments (average of 8 different conditions in each set) were done over the course of optimization, confirming the reproducibility of the results.

Metabolomics. Cultures for metabolomics analysis were grown according to standard methods as outlined in the Growth conditions and compound expressions section. Aliquots were taken from log phase cultures and 120 h post-inoculation. Cells were pelleted and frozen at −80° C. until analysis. Frozen cells were homogenized by the addition of ice-cold 500 μL 2-propanol (10 mM ammonium formate, pH 3.2) containing the internal standard GSH-ethyl ester (0.01 mg/mL) to each sample. Samples were vortexed and sonicated then transferred to bead tubes (1.4 mm) and homogenized for 30 sec and returned to ice. To each cell homogenate, 200 μL of ice-cold acetonitrile was added and the samples were kept on ice for 10 min. The samples were then centrifuged for 10 min at 14K G at 4 C. Supernatants were transferred to microcentrifuge tubes and 25 μL was removed then transferred to an LC/MS vial for immediate analysis. The remaining supernatant was dried via speedvac.

Samples were resuspended in water (50 μL, 10 mM ammonium formate, pH 3.2)/ACN (1:1). Of this volume, an aliquot (5 μL) of each sample was injected on a ZIC-pHILIC column equipped with a guard column (SeQuant, 100×2.1 mm, 5 μm particle size). Column compartment cooler was operated at 10° C. HPLC mobile phases used were: A—100% acetonitrile, B—10 mM ammonium formate in H2O, 0.1% formic acid, pH~3.2. Samples were eluted on the following gradient: (t=0min): 95% A, 5% B; (t=0.5min) 95% A, 0% B; (t=22.5 min) 40% A, 60% B; (t=23 min) 40%

A, 60% B; (t=25 min) 95% A, 5% B; (t=35 min) 95% A, 5% B. HPLC flow rate was 0.2 ml/min.

Metabolite Extraction. Frozen cells (300-400 µL of supernatant and pellet) were homogenized by the addition of ice-cold 2-propanol (500 µL, 10 mM ammonium formate, pH 3.2) containing the internal standard GSH-ethyl ester (0.01 mg/mL) to each sample. Samples were vortexed and sonicated then transferred to bead tubes (1.4 mm) and homogenized for 30 sec and returned to ice. To each cell homogenate, ice-cold acetonitrile (200 µL) was added and the samples were kept on ice for 10 min. The samples were then centrifuged for 10 min at 14K G at 4° C. A portion (25 µL) of each supernatant was transferred to an LC/MS vial for immediate analysis. The remaining supernatant was dried via speedvac and stored.

LC-MS analysis-redox metabolites. Samples were analyzed using a Phenomenex (Torrance, Calif.) 3.0 mm×150 mm Gemini-NX C18 (5 µm) column with a Phenomenex Security Guard column filled with the same packing material. The chromatographic system consisted of an integrated Shimadzu HPLC system consisting of two LC-10AD pumps, column oven and a CBM-20A 82 controller. A PE200 autosampler with a cooling unit set to 4° C. was used for sample handling. A PE Sciex API 365 mass spectrometer modified with an Ionics EP 10+ source was used for analyte detection. A mobile phase consisting of solvent A (water with 15 mM ammonium formate/6.5 mM N-dibutylamine) and solvent B (methanol/6.5 mM N-dibutylamine) was used for elution of samples. The initial condition was 5% B with an initial hold time of 3 minutes followed by a ramp to 73% B over 21 min. A second ramp to 90% B was employed over the next minute with a 1 minute hold. The column was brought back to 5% B over two minutes and re-equilibrated for 9 minutes. The flow rate was 0.3 mL/min at 24° C. Mass spectrometer transition optimization was performed using a syringe pump. For each metabolite optimized it was dissolved in buffer A as a 1 mg/mL solution. Infusion was performed at 20 µL/min while 10% B/90%A buffer was co-infused using the HPLC at 0.3 mL/min. Samples were prepared as follows: to prevent the exogenous oxidation of GSH it was derivatized using 2-vinyl pyridine. To each sample was added 10 mM $K_2PO_4$ pH 7 (48 µL) and 2-VP (2 µL). A brief sonication using a water bath was performed to fully elute each sample. After 30 minutes of incubation at room temperature 50 µL of buffer A was added followed by 10 min of centrifugation at 20000×g. 90 µL of this was transferred to an autosampler vial and immediately transferred to the autosampler which was held at 4° C. until analysis. After analysis each metabolites peak height was recorded in Analyst (Sciex) and transferred to Excel for further analysis.

LC-MS metabolomics. Metabolomics analysis was performed using an Agilent 6550 QTOF fitted with an Agilent 1290 UHPLC. Samples were chromatographically separated by a ZIC-pHILIC column equipped with a guard column (Merck Millipore), 100×2.1 mm, particle size 5 µm. The column was maintained at 10° C. LC mobile phases used are: A—100% acetonitrile, B—10 mM ammonium formate in H2O, 0.1% formic acid, pH ~3.2. LC gradient employed as follows: (t=0 min): 95% A, 5% B; (t=0.5 min) 95% A, 0% B; (t=22.5 min) 40% A, 60% B; (t=23 min) 40% A, 60% B; (t=25 min) 95% A, 5% B; (t=35 min) 95% A, 5% B. HPLC flow rate was 0.2 ml/min. Metabolites were detected in the positive with nebulizer gas temperature held at 290° C., a drying gas flow of 11 l/min; the nebulizer pressure set to 35 psig, sheath gas temperature set to 300° C.; sheath gas flow held at 7 l/min, capillary voltage of 4000 V, nozzle voltage=0 V, fragmentor=380 V, and the skimmer held at 65 V. Peak lists from the acquired data was generated using Profinder (Agilent) followed by significance testing analysis by Mass Profiler Professional.

Processing and peak alignment. The mzXML data sets generated from the logarithmic and 5-days cultures were analyzed separately. Data sets were individually pre-processed through XCMS (version 1.32.0) for peak picking and alignment in R (version 2.15.0). Technical data replicates from E. coli cultures containing vector pTru-SD1 and supplemental conditions (B: +cysteine, F: +cysteine+mBI, and H: +cysteine+mBI+mevalonate) were considered as two separate groups in XCMS. Peak picking was performed with a 10-fold signal to noise threshold, and nonlinear local regression fitting was used to align sample peaks with a grouping bandwidth of 20. This yielded 4902 and 4580 features, including isotopes and adducts, for the day 5 and logarithmic growth conditions, respectively. Peak processed data were then normalized by total ion count per chromatographic run in Microsoft Excel.

Statistical analysis. Multivariate statistical analyses were performed using Umetrics extended statistics software EZinfo version 2.0.0.0 (Waters, Milford, Mass.). Normalized values were transferred into the EZinfo input spreadsheet, and m/z and retention time were set as the primary and secondary variables respectively. The Pareto PCA template was used generate the output PCA scores plot. For self-organizing map analyses, features from technical replicates were averaged, and date were formatted in the GEDI software (version 2.1) input format. A grid of 49×50 nodes was selected, with 80 and 120 first and second phase training iterations. The parameters for phase one were: 4.0 for neighborhood radius, 0.5 learning factor, 4.0 neighborhood block size, and 3.0 conscience. Phase two parameters were: 2.0 neighborhood radius, 0.05 learning factor, 2.0 neighborhood block size, and 3.0 conscience. A random seed of 1 was used to initialize organization. Pearson's correlation was selected for the distance metrics and a random seed initialization method was used. Difference maps were generated using the GEDI software by subtracting control node intensities from each of the treatment conditions as well as subtracting treatment conditions from the control. Features contained in hot spots on the maps were extracted to generate feature heat maps.

Effect of sulfide on cyanobactin pathway proteins. The TruE-3-2 precursor was cloned as a N-terminal His-tagged construct into pET-28b between NdeI and XhoI site by around the horn cloning of an existing plasmid that carried only the patellin 3 cassette along with the native TruE leader sequence. Primers were made with 5'-phosphorylated ends carrying the additional patellin 2 cassette. The PCR product was DpnI digested, gel purified and ligated using T4 ligase and plated on LB-kanamycin, followed by colony screening to select for the correct plasmid. The plasmid truE-3-2 was transformed into BL21-R2D cells and grown in 2xYT medium with antibiotics chloramphenicol (25 µg mL$^{-1}$) and kanamycin (50 µg mL$^{-1}$). Once an $OD_{600}$ of 0.5 was achieved, the cultures were induced with 1 mM IPTG and overexpressed at 37° C. for 3 h, following which they were harvested and the cell pellets stored at −80° C. till used for purification. TruE-3-2 was purified under denaturing conditions. The enzymes used in this study ThcD, PatA and TruG were made as described above.

All assays were carried out in optimized reaction condition with Tris pH 7.5 (50 mM), $MgCl_2$ (5 mM), $CaCl_2$ (10 mM) in assays with PatA, DTT (7.5 mM) in assays with ThcD and TruE-3-2, ATP (1 mM) in assays with ThcD and in assays that were compared to ThcD containing assays, substrate TruE-3-2 (50 µM) unless otherwise specified and enzymes ThcD (2 µM), PatA (2 µM) and TruG (17 µM) at 37° C. at specified time-points. ThcD reactions that were analyzed by SDS-PAGE were quenched with 6× loading dye and frozen until analyzed. All other assays were quenched with MeOH and 30 mM DTT and frozen until analyzed by HPLC-MS.

Addition of sulfide into assays was carried out by making a fresh stock of $Na_2S$ (100 mM) in Tris pH 7.5 (50 mM) and the solution purged with argon in airtight glass vials. From this stock solution, required volume of solution was drawn using a syringe and added to assays to maintain a final concentration of 500 µM in reaction volume. An aliquot for each time-point was separated into tubes immediately at the start of the assay, to prevent loss of sulfide by opening of tubes between time-points. Assays with higher concentrations of sulfide such as 5 mM or 1 mM were inhibitory to all enzymes (data not shown).

Results

Example 2

Figure 2:
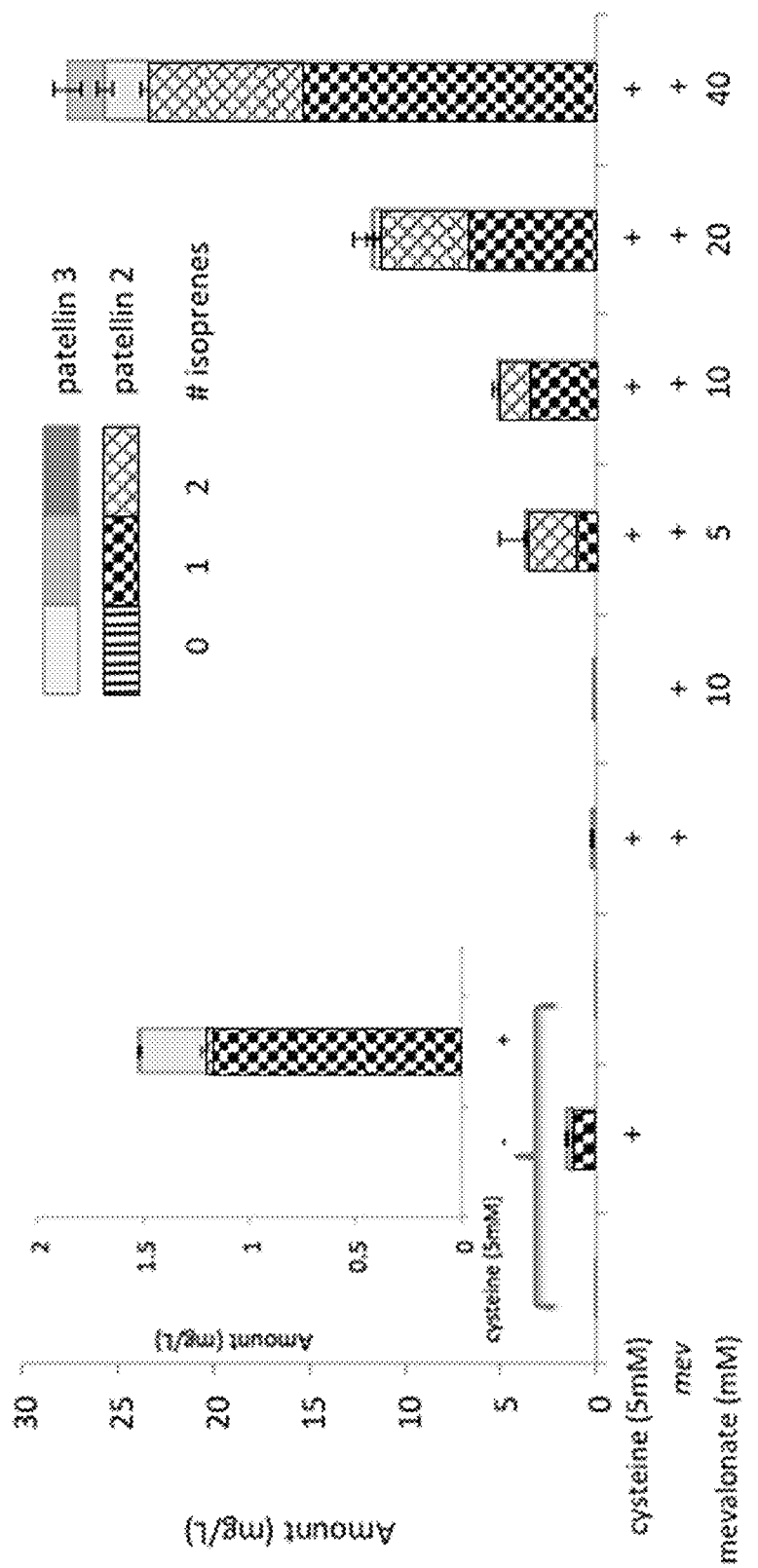
FIG. 2 shows optimization of patellin 2 and 3 production in *E. coli*. Cyanobactin RiPPs patellins 2 and 3 were synthesized in *E. coli* using the vector pTru-SD, with added agents shown on the x-axis. Cultures were harvested on fermentation day 6. Yield was measured by comparison to an internal standard that was used to generate a standard curve (see FIG. 9). Measurements were made from independent replicates performed in triplicate. Different degrees of prenylation are indicated by progressively darker shading for patellin 3. For patellin 2, products with zero isoprene units are indicated by vertical lines, 1 isoprene unit indicated by checkerboard pattern, and 2 isoprene unites indicated by diamond crosshatching. Inset: With and without cysteine only, showing large increase upon addition of cysteine.

Optimization with cysteine and mevalonate. Production of the tru pathway in *E. coli* was optimized using vector pTru-SD by traditional methods, leading to a best yield of <10 µg L-1 over a 5-day fermentation period. These experiments used the entire tru operon encoding the substrate TruE-3-2, where patellin 3 is encoded in the first cassette, and patellin 2 is in the second. A metabolite-directed approach was applied, in which reagents were added to pTru-SD *E. coli* cultures, and production of compounds was monitored by mass spectrometry. Quite unexpectedly, exogenously added cysteine reproducibly increased the yield of patellins. Cysteine concentrations of 5-10 mM were optimal, which along with minor process changes increased cyanobactin production by 150-fold, to ~1.5 mg L-1 (see FIG. 2 and FIG. 9). Under these conditions, a mixture of patellins with 0-2 units of isoprene was produced, and prenylation slowly increased over a series of days. Therefore, production of the isoprene precursor, dimethylallylpyrophosphate (DMAPP), was increased using vector pMBI, which contains genes (mev) that convert mevalonic acid to DMAPP, which in turn is a substrate for prenyltransferase TruF1. In the event, co-expression of pTru-SD and pMBI led to a great increase in prenylation that depended on the dose of added mevalonate (FIG. 2). Surprisingly, addition of mevalonate also greatly increased the total yield of patellins by ~18-fold from cysteine alone, to 27 mg L-1. This increase was dependent upon cysteine, since absent cysteine no increase in yield was observed with added mev/mevalonate. Approximately 250 mg L-1 of precursor peptide TruE-3-2 was synthesized, representing ~25% of the dry weight of the cells. This is a striking effect, which greatly exceeds known yields of RiPPs by precursor weight. The obtained yield greatly improves the ability to scale and produce both discrete compounds and combinatorial libraries of RiPP products.

Example 3

Figure 3A:
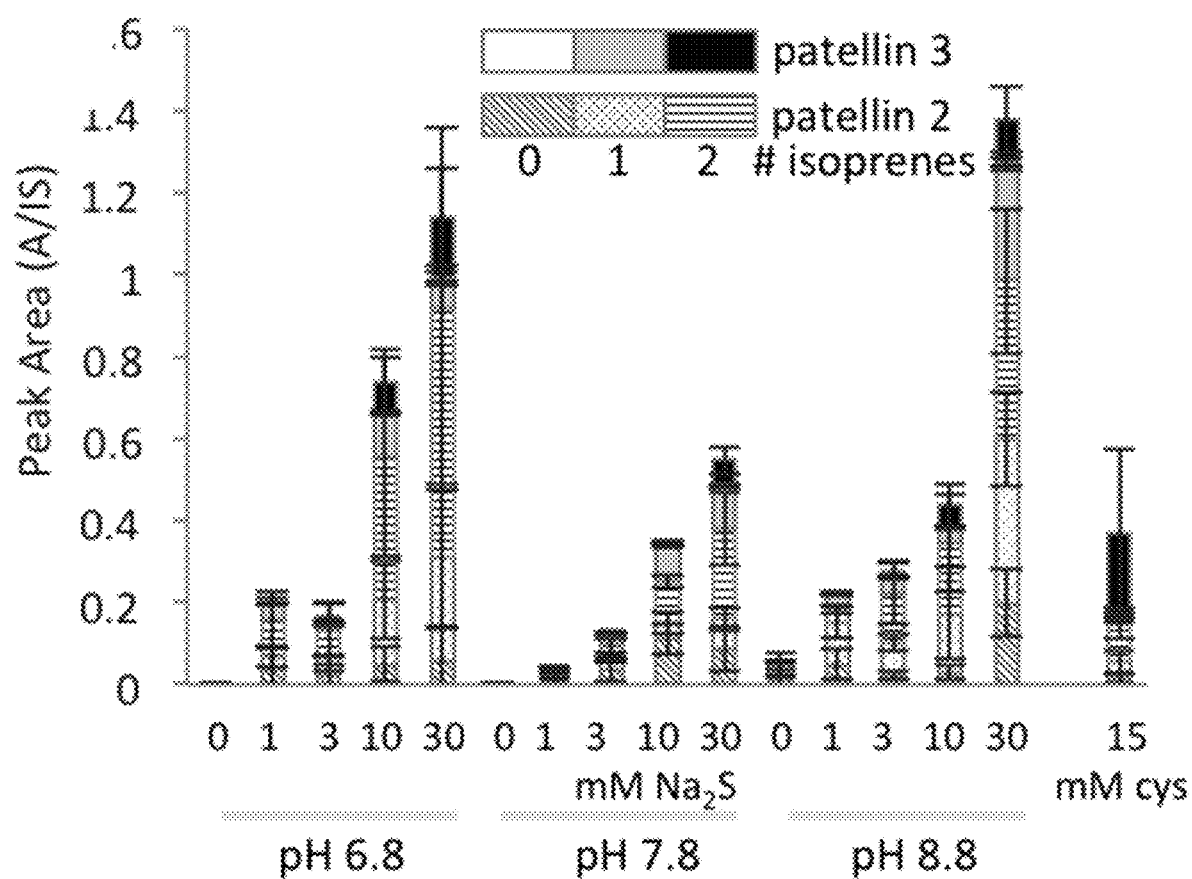
FIG. 3A shows the addition of sulfide leads to cyanobactin RiPP production. Cultures were grown for three days. Each condition was measured from three separate cultures. Note that acetone extracts were dissolved in the same volume of methanol (500 µL) as used for samples in other figures, but these samples were extracted from smaller cell pellets (from 2 mL culture instead of from 6 mL culture).
Figure 11A:
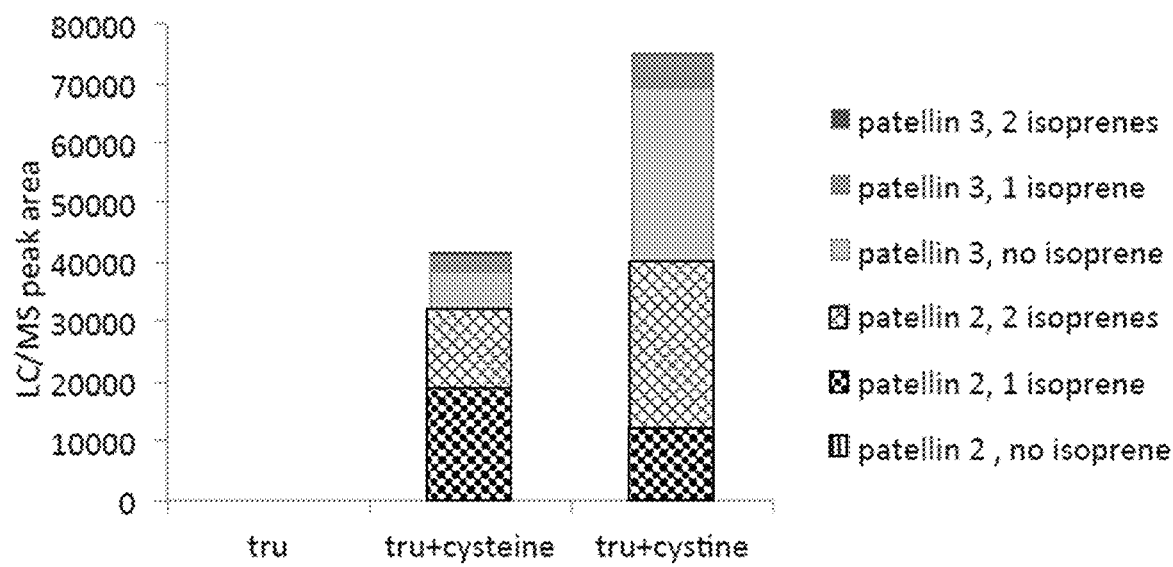
FIG. 11A shows cyanobactin RiPP production in cultures grown with cysteine and cystine. Cultures were grown for six days as described in the Methods with no addition, addition of 5 mM cysteine-HCl or addition of a solution of 2.5 M cystine from a stock solution adjusted to the same pH as the cysteine-HCl stock.
Figure 11B:
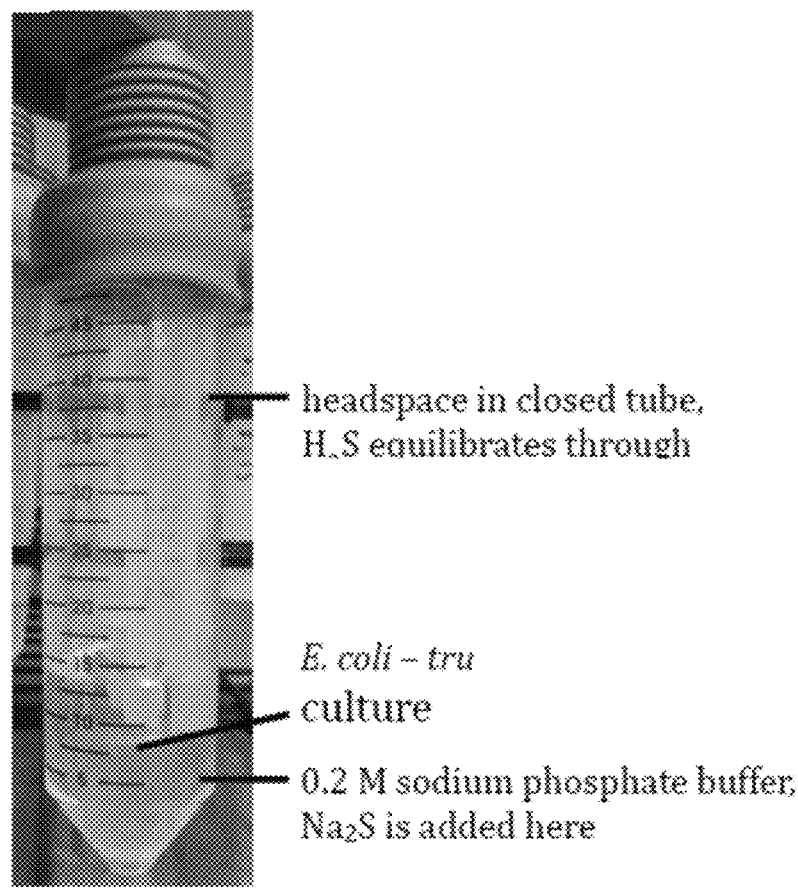
FIG. 11B is a culture setup for analysis of sulfide response.
Figure 20A:
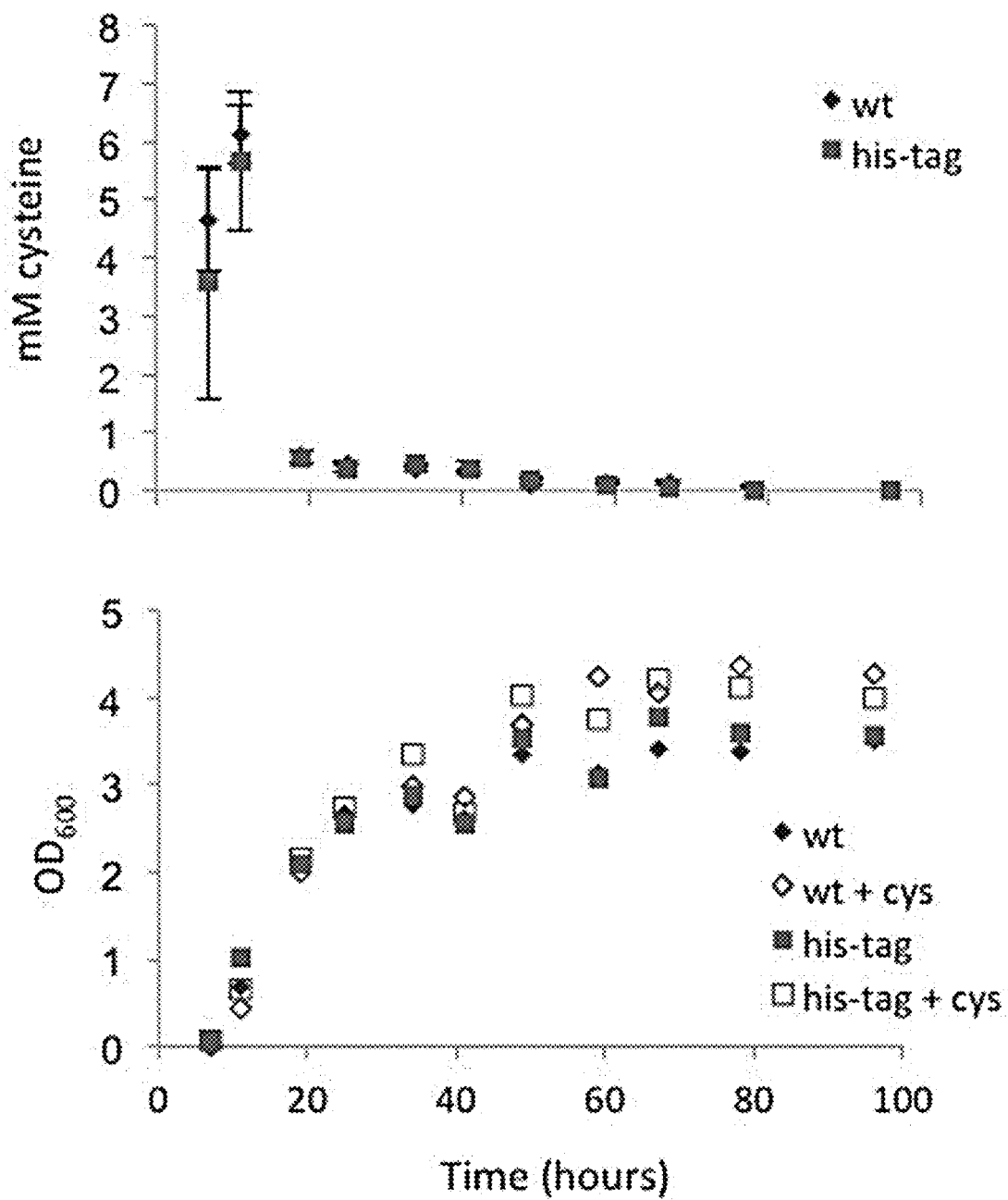
FIG. 20A shows cysteine is consumed at about 18 h, which corresponds to late log phase. The same cultures as in FIGS. 3B and 3C were used. Measurements were performed in triplicate. A standard curve for cysteine concentration is shown in FIG. 13.

Cysteine functions by liberation of hydrogen sulfide. Cysteine was not previously known to improve the yield of any pathway. Cystine could replace cysteine (FIG. 11A), and yield depended upon vessel size and shape. Cysteine was used in an experiment in which the cover of a multiwell plate was not pierced to allow gas exchange. In that event, control wells lacking cysteine exhibited a great increase in patellin production, suggesting that the active reagent was volatile such as hydrogen sulfide. Indeed, in *E. coli* cultures, cysteine and cystine are completely degraded during *E. coli* growth (FIG. 20A). Surprisingly, upon liberating $H_2S$ gas into cultures at varying concentrations (FIG. 11B), hydrogen sulfide alone was sufficient to recapitulate the increased patellin 2 and patellin 3 yields found with cysteine (FIG. 3A). Pyruvate, lactate, and related compounds did not affect patellin production.

Four major possibilities were tested, in which hydrogen sulfide might impact: 1) the abundance of cyanobactin proteins; 2) the availability of metabolites or co-factors; 3) cellular redox; 4) activity of proteins.

Figure 12:
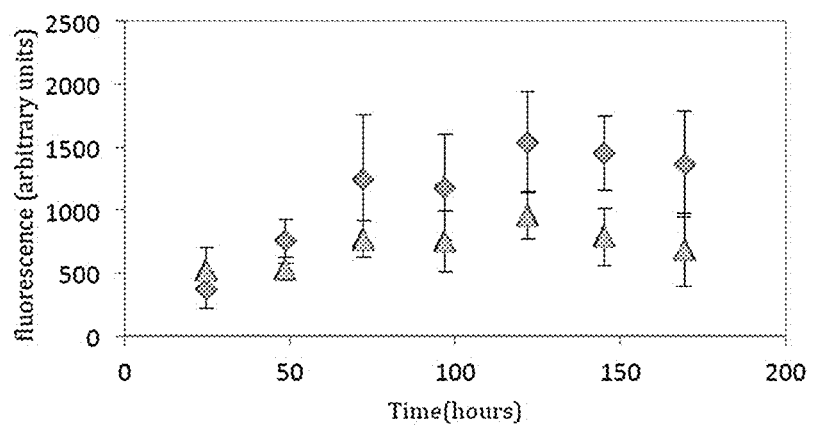
FIG. 12 shows that cysteine does not improve lac transcription. (A) Total fluorescence (after reduction) of cells expressing lac-roGFP2 is shown. For each sample, OD600 was measured and a culture volume equivalent to 2 mL at OD600 =1 was harvested, cells were suspended in 120 µL PBS with 10% (v/v) glycerol, and each sample was divided into two wells in a 96-well plate. All samples (over several days) were collected in one plate. The plate was thawed and 5 mM dithiothreitol was added to one well from each sample. After 30 minutes incubation at room temperature, the plate was read with excitation at 490 nm and emission at 520. DTT addition and incubation were repeated and the plate was read again to make sure gfp was fully reduced. The figure shows OD600 (top) and fluorescence (bottom) of reduced roGFP2 from samples taken over 170 hours' growth. Diamonds: cultures without added cysteine; triangles: cultures supplemented with 10 mM cysteine. Since the samples were normalized for OD600, the relative fluorescence should correlate directly with the amount of roGFP2 in cells.
Figure 12:
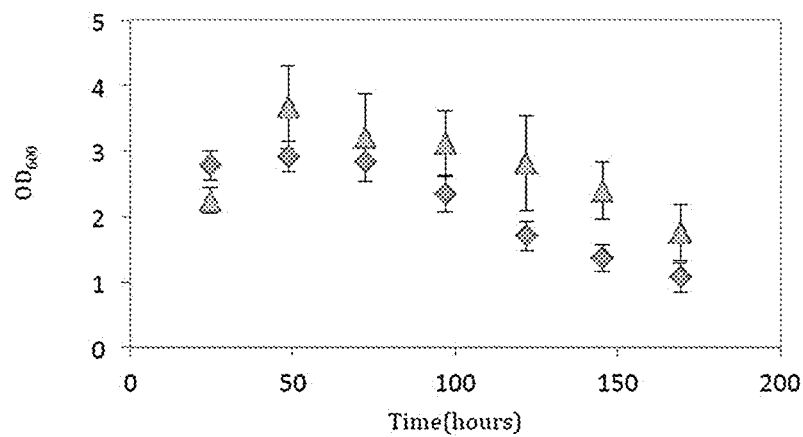
Figure 13:
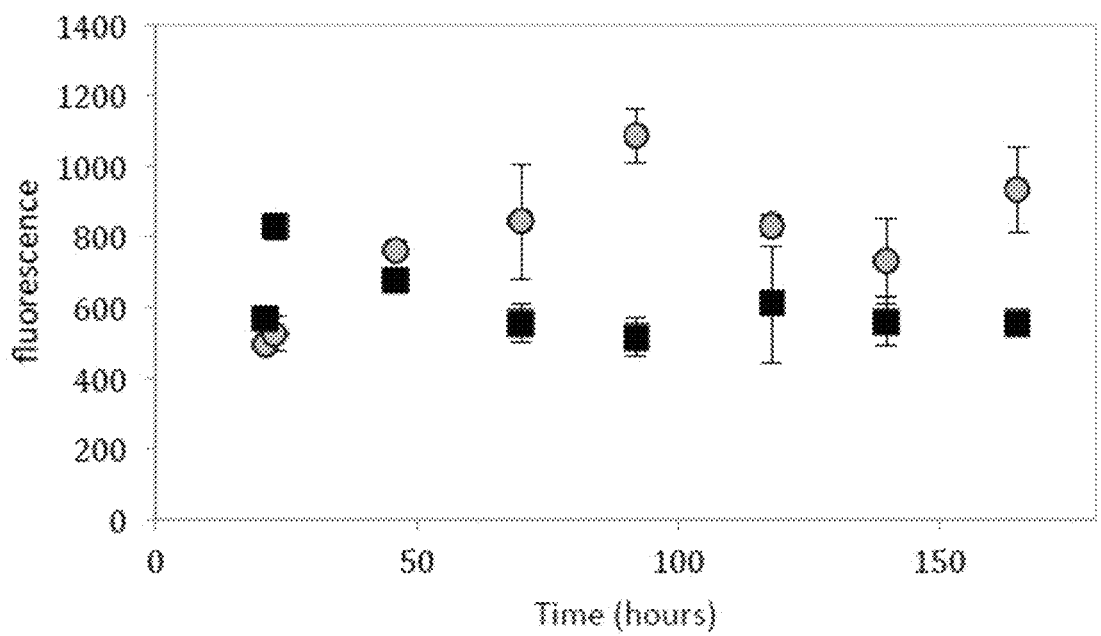
FIG. 13 shows that a lac-tru-gfp vector was expressed, and fluorescence in normalized amounts of cells was measured over 180 h. Growth was modestly increased by cysteine, while GFP fluorescence was modestly decreased (black squares) in comparison to the same cells absent cysteine (gray circles). Measurements were performed in independent cultures in quadruplicate.
Figure 13:
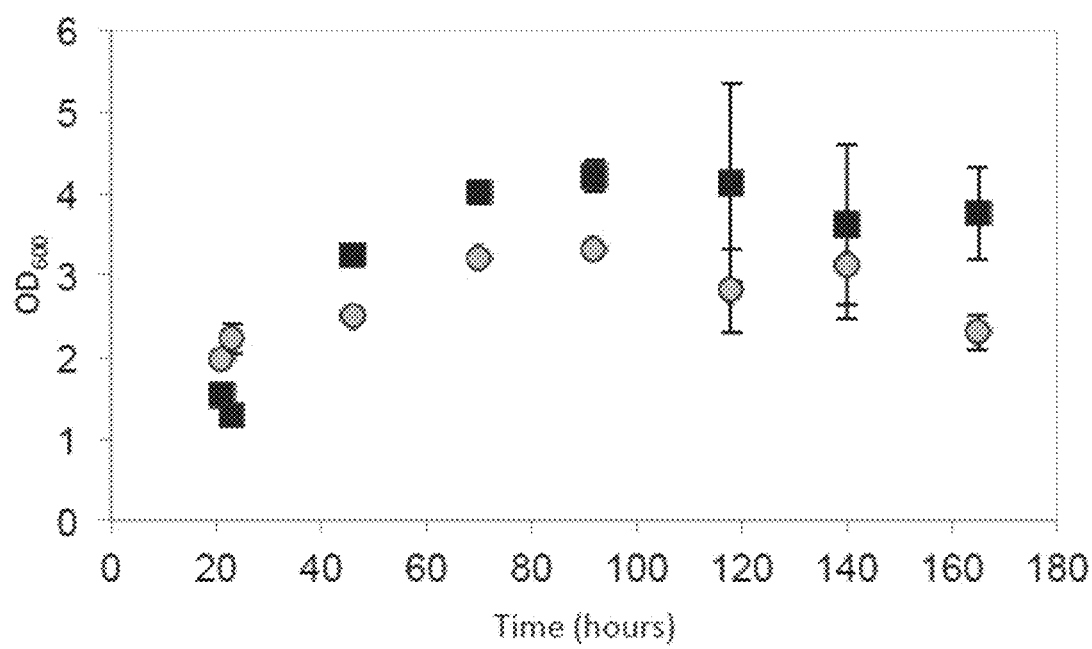

Molecular mechanism 1: protein abundance is not altered. In pTru-derived vectors, the tru operon is under control of the *E. coli* lac promoter. Use of a lac promoter-green fluorescent protein (GFP) fusion showed that GFP is modestly decreased when cysteine is introduced (FIG. 12). Similarly, when gfp was fused directly to the last gene in tru, fluorescence was modestly diminished with cysteine in comparison to cysteine-free controls (FIG. 13). The production and stability of all tru enzymes under control of individual T7-lac promoters showed no significant effect.

Figure 3B:
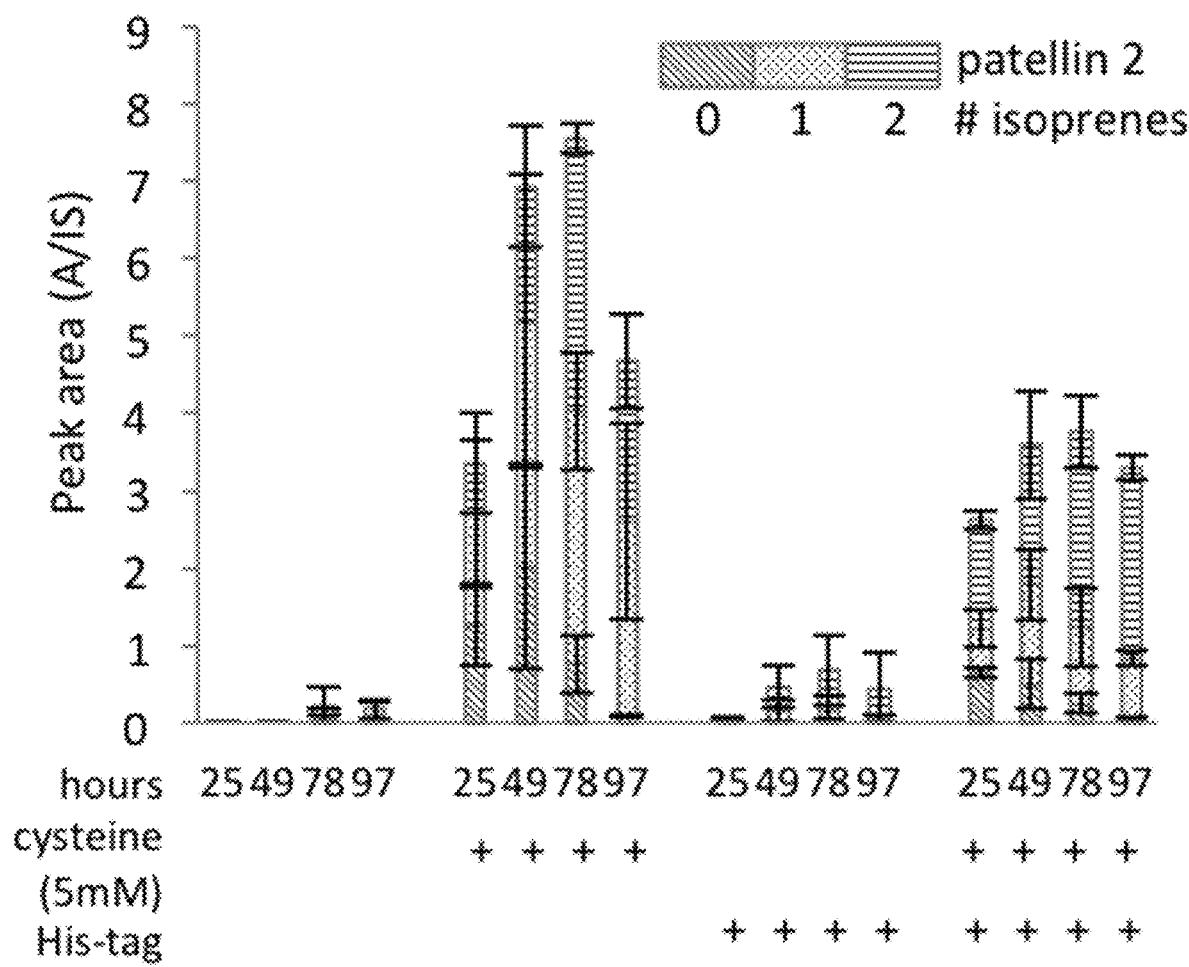
FIG. 3B shows the production of patellin 2 in vectors with and without His-tag showing that production is cysteine responsive and increases even after cysteine is depleted from culture (see FIG. 20A) and days after TruE-2-2 disappears from culture (FIG. 3C). Measurements were performed in triplicate from independent cultures.
Figure 3C:
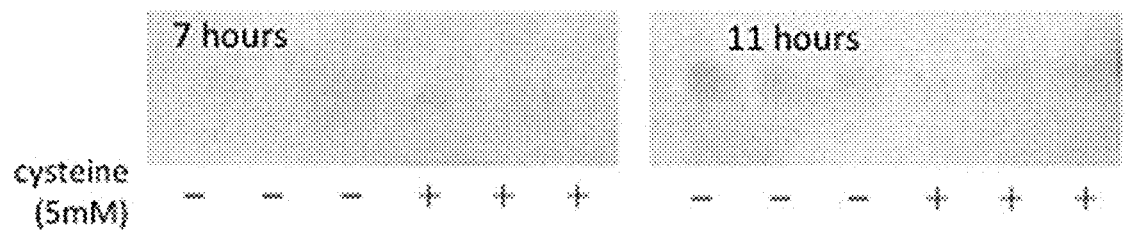
FIG. 3C shows TruE is expressed early in the log phase, and its synthesis or degradation does not differ with or without cysteine. Western blot against His-tagged TruE-2-2 shows that the protein is only visible at 7 and 11 h, while later time points are not visible independent of cysteine addition. Additional points and conditions are shown in FIG. 16.
Figure 3D:
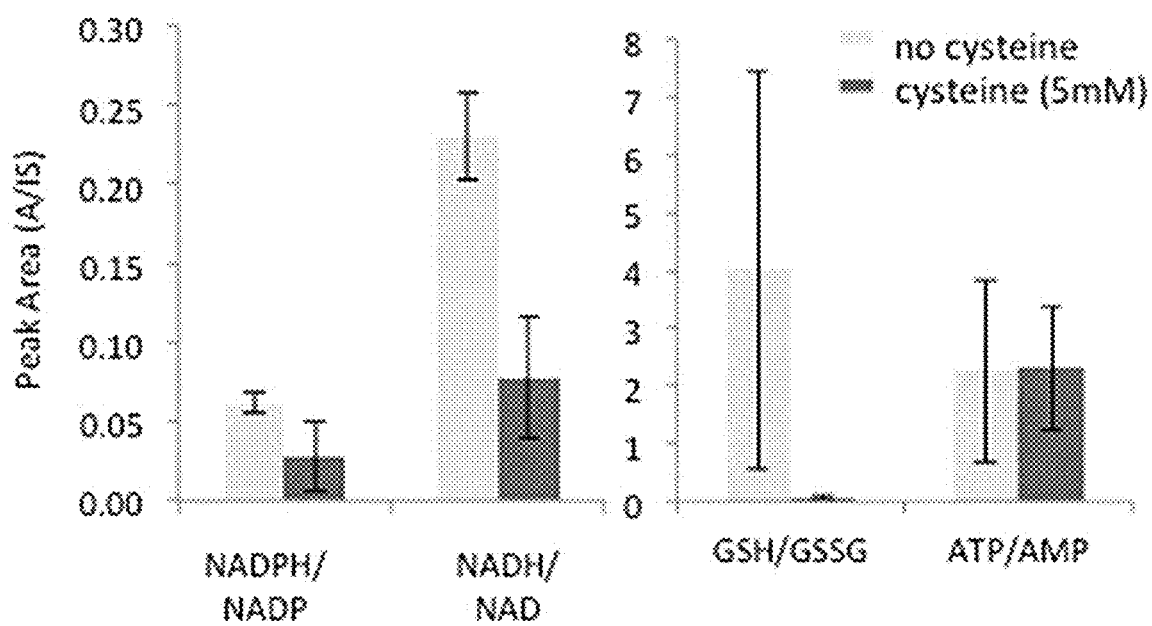
FIG. 3D shows the addition of cysteine (5 mM) leads to oxidation of redox-sensitive metabolites, but has little effect on ATP/AMP ratio in *E. coli*. Measurements were made in four independent cultures using 100 mL scale cultures, harvested after 24 hours.
Figure 3E:
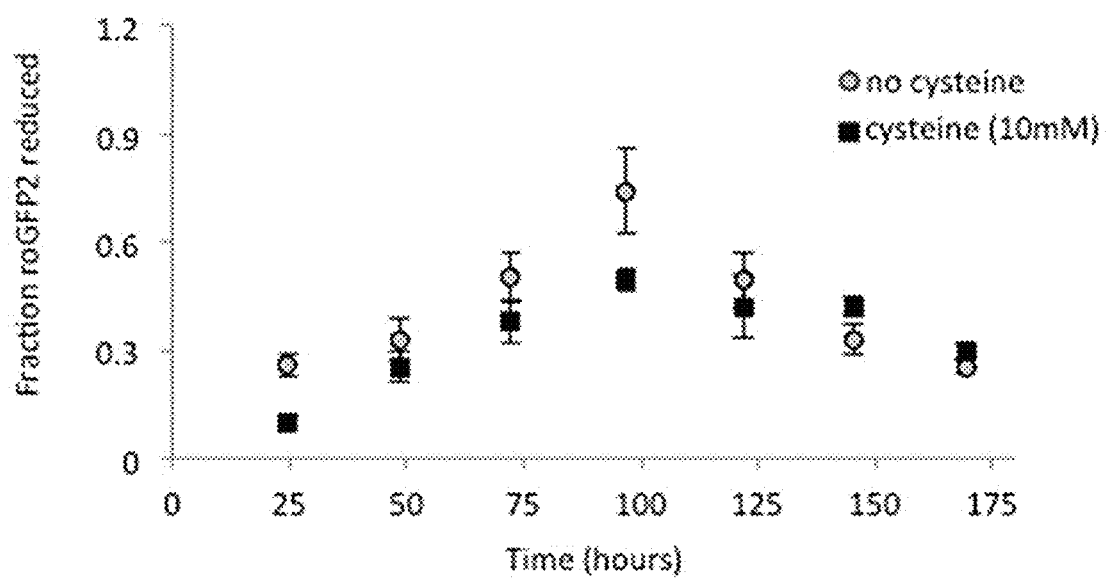
FIG. 3E shows adding 10 mM cysteine has little effect on the growth of *E. coli*, but leads to oxidation of the cytoplasm, as measured by the redox state of redox-responsive roGFP2. Each data point is the average of at least six independent cultures. Spectra of reduced and oxidized roGFP2 in *E. coli* are shown in FIG. 11E.
Figure 16:
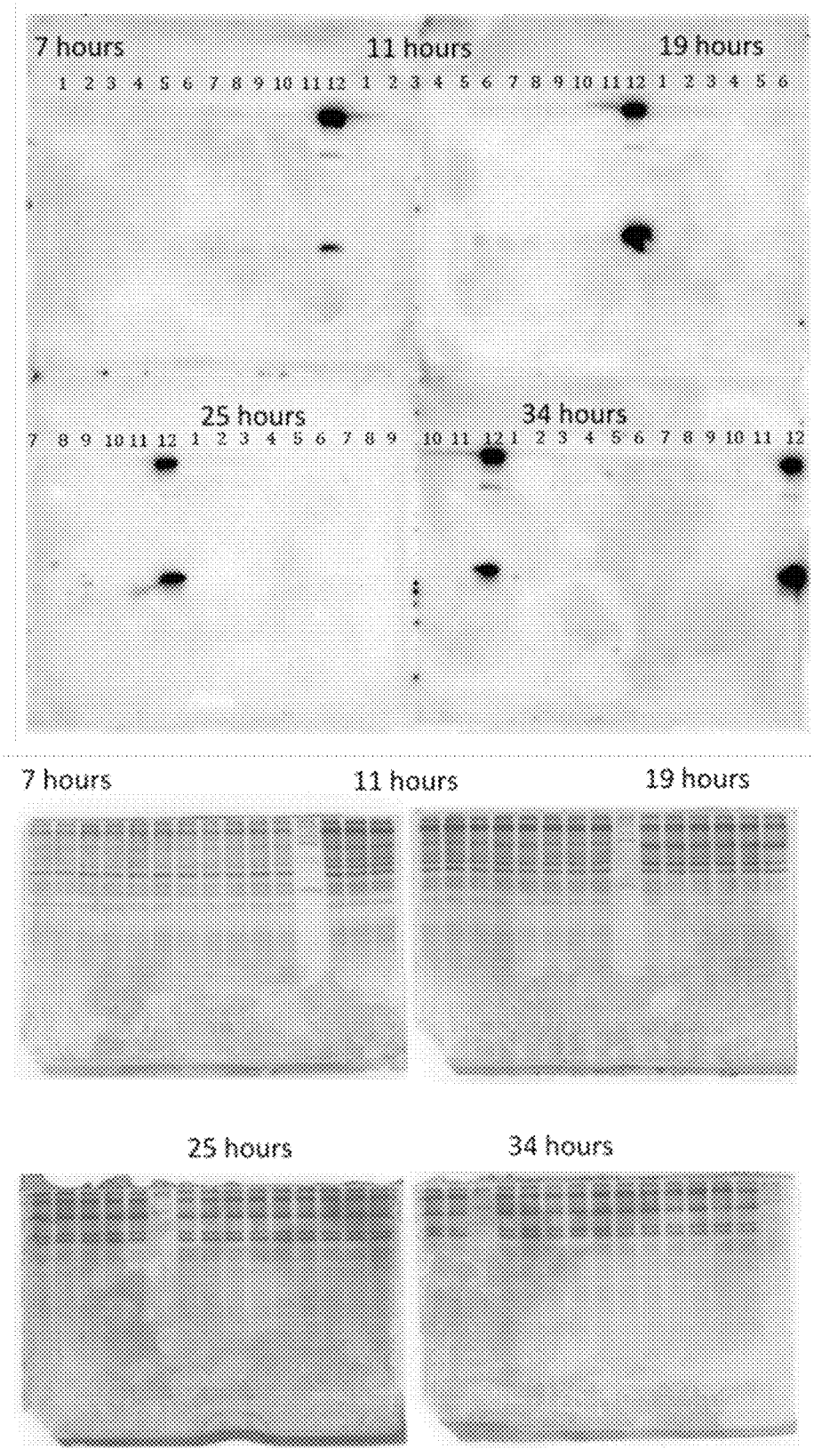
FIG. 16 shows gels and western blots of internally his-tagged TruE expressed from pTru-his-int. Top: western blots. Bottom: gels from the same experiment, stained with coomassie after transfer to membranes for western blots. The loading volume was normalized to approximate loading protein from 80 µL of cells from an OD600=1 culture. Samples are in groups of eleven, with positive controls for the western blot between sets of samples. The positive control was prepared from a pET-TruE2 expression (gel 1, sample 14 from the pTARA expression shown in the previous figure), with his-tagged prenyltransferase (~35 kDa) added to provide an additional band. Loading for each set of samples (from left to right)

The truE-2-2 (encoding patellin 2 in both cassettes) gene was modified by inserting a 6×His tag into the leader sequence (FIG. 3B-FIG. 3C). In western blots, TruE-2-2 was observed after 7 h of fermentation (early log phase) and optimal around 11 h (mid-log), but was no longer detectable by late-log phase (17 h and later). No difference was observed in the presence or absence of cysteine (FIG. 16). By contrast, detection of cyclic products was greatly increased when cysteine was added to the media. Thus, the effects of cysteine are not explained by an increase in TruE production or stability.

Figure 17A:
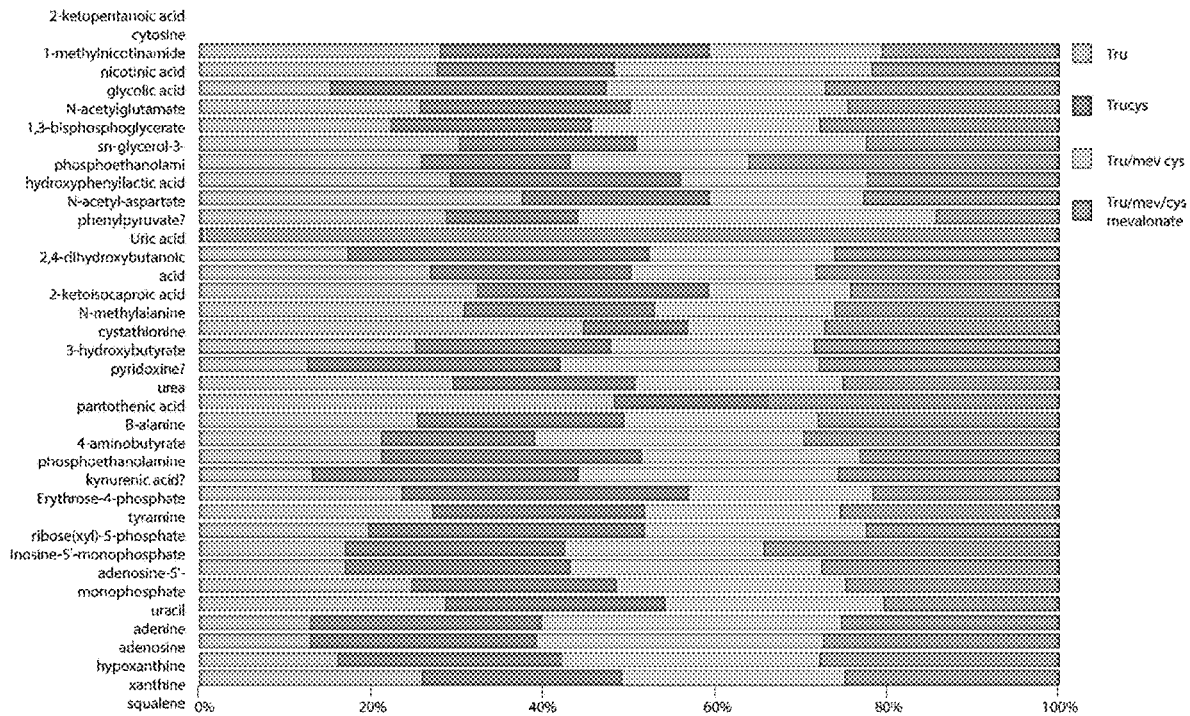
FIG. 17A shows GCMS metabolomic analysis showing a minimal change in known primary metabolites under different conditions at day 5.
Figure 17B:
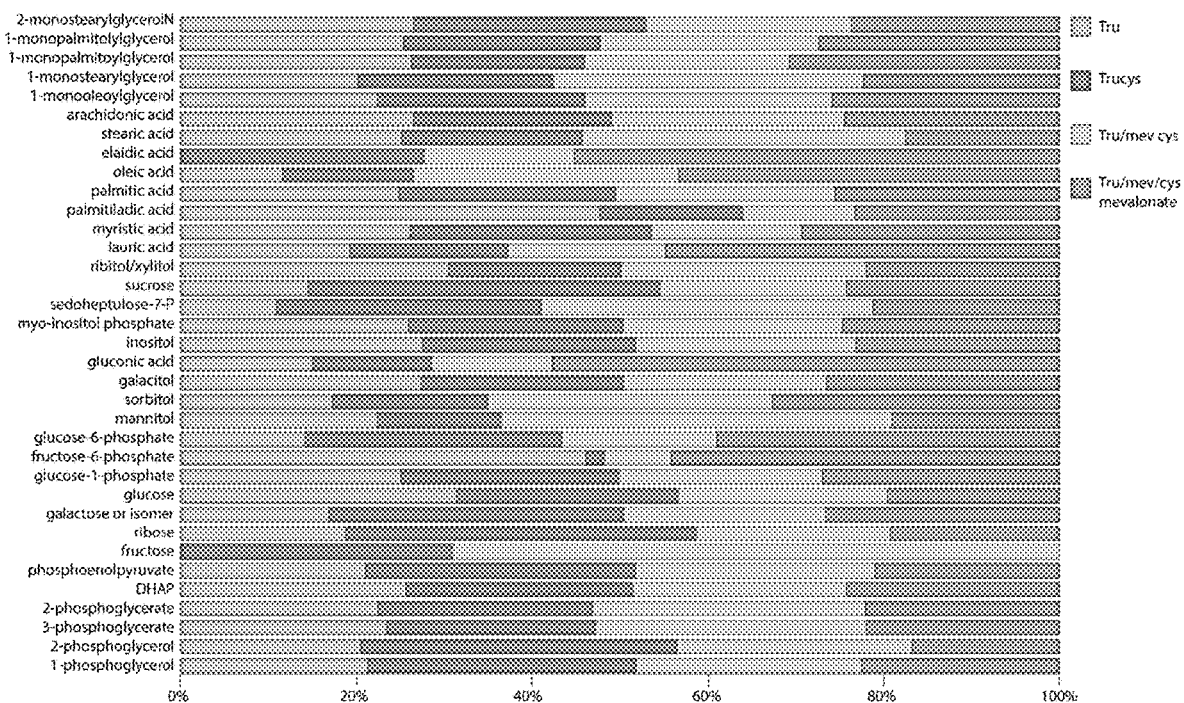
FIG. 17B shows GCMS metabolomic analysis showing a minimal change in known primary metabolites under different conditions at day 5.
Figure 17C:
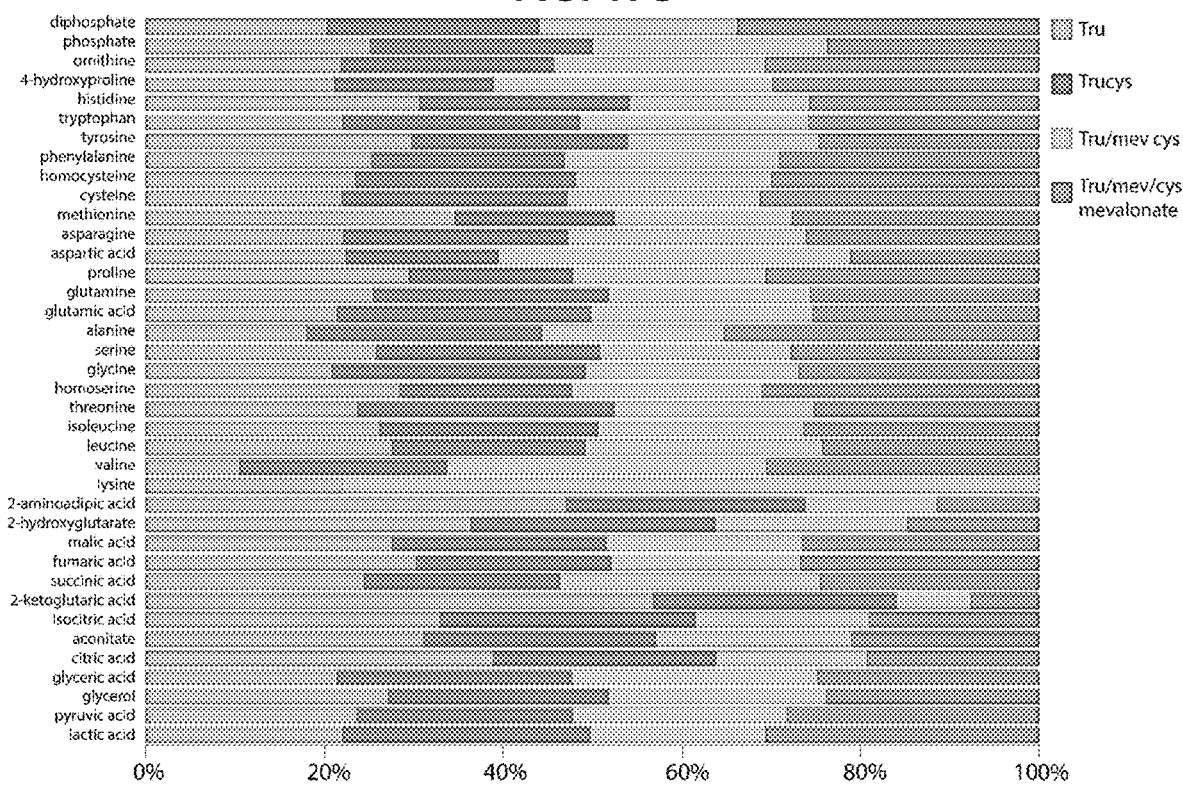
FIG. 17C shows GCMS metabolomic analysis showing a minimal change in known primary metabolites under different conditions at day 5.
Figure 17D:
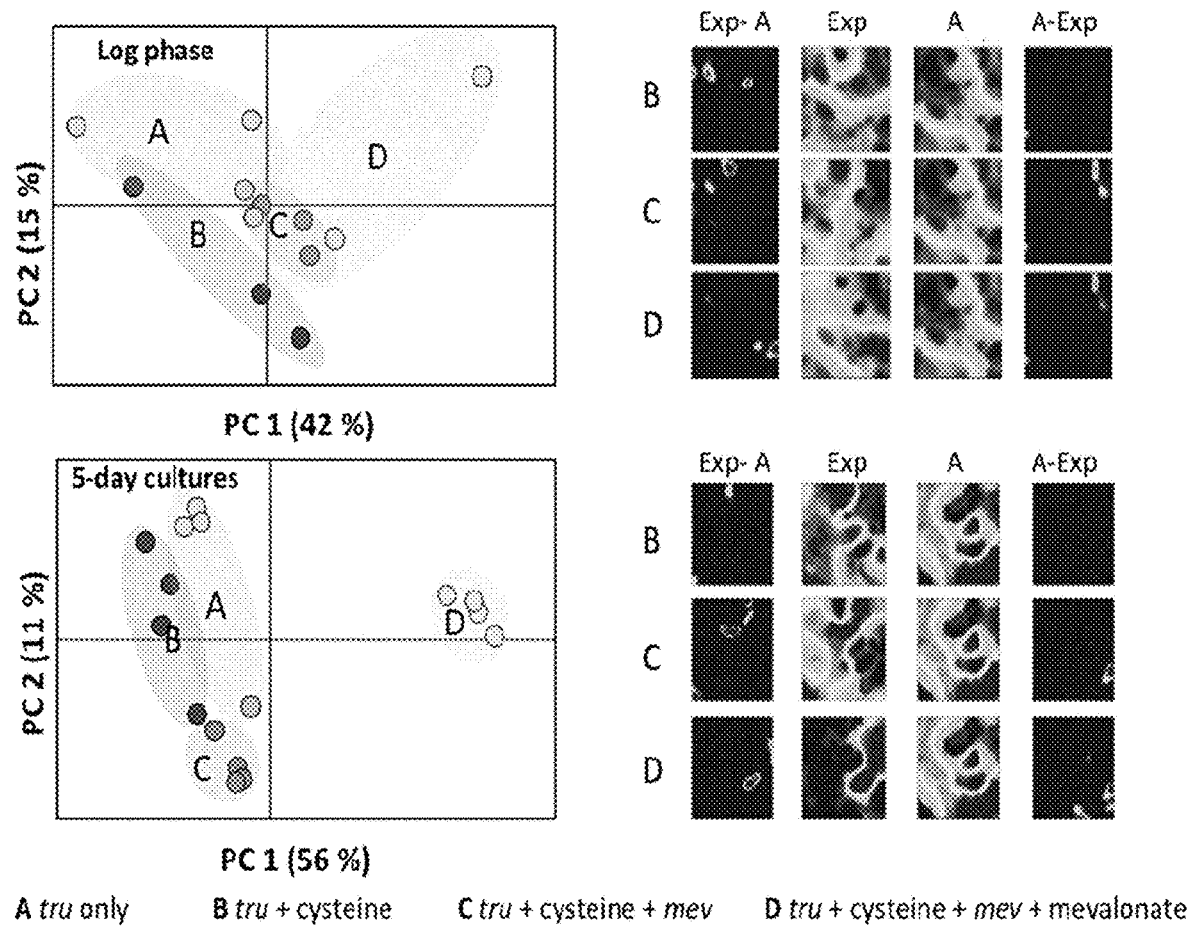
FIG. 17D shows the (left panel) principal components analysis of cultures harvested (followed by OD) at mid-log phase and after five days showing that the presence of cysteine does not cause significant changes in the E. coli metabolome both in time points while the biggest differences are observed when mev and mevalonate is added. Individual independent runs are indicated by small circles. (Right panel) MEDI self-organizing maps of the LCMS metabolomes showing features that change in different conditions versus tru only expression.
Figure 18A:
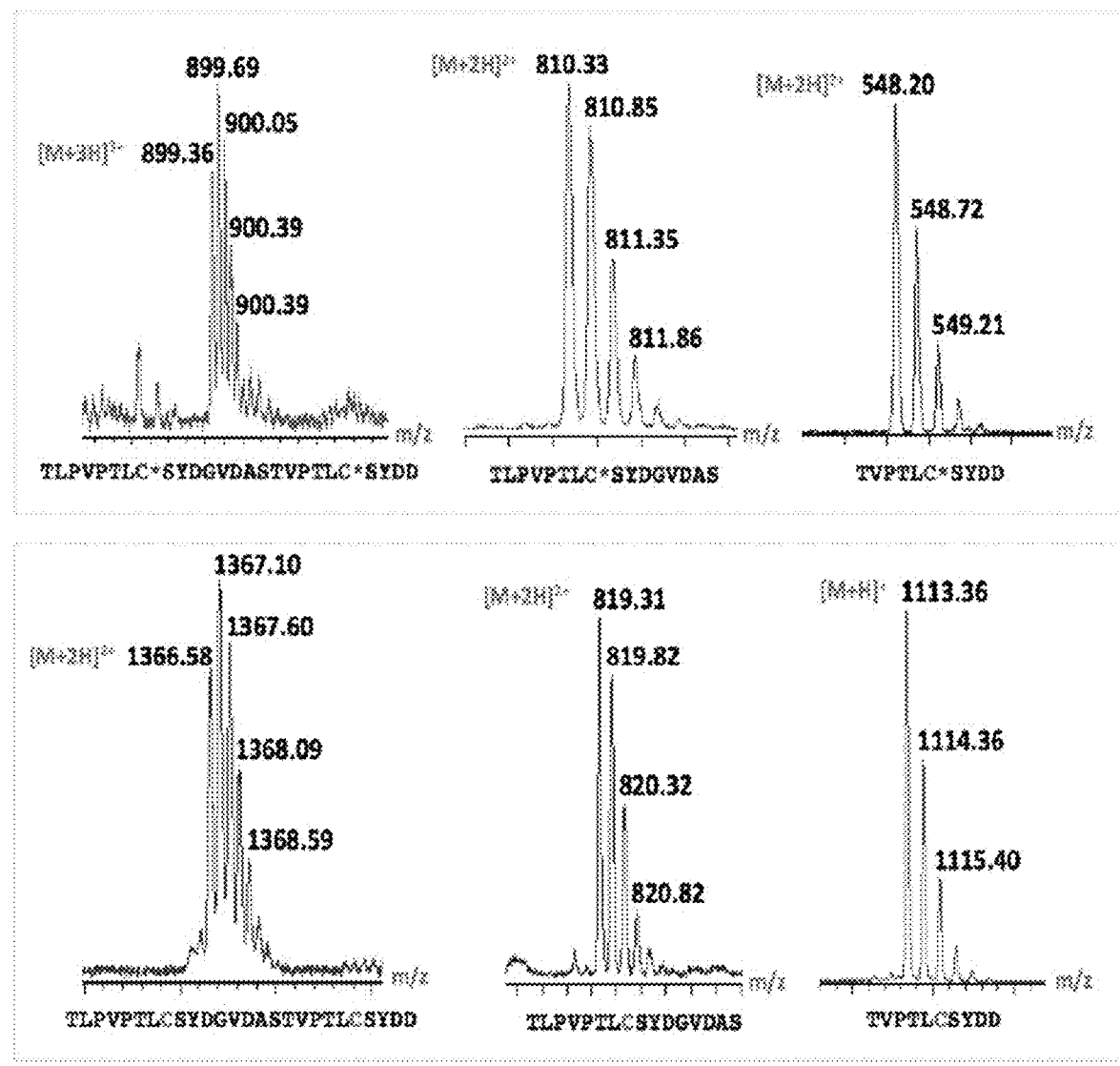
FIG. 18A is the mass spectra of possible PatA intermediates. Correct PatA intermediates carry the thiazoline heterocycle (represented by C*) and are subsequent substrates for PatG, whereas the erroneous intermediates are non-heterocyclized (the unmodified Cys is shown in grey) and cannot be processed by PatG.
Figure 18B:
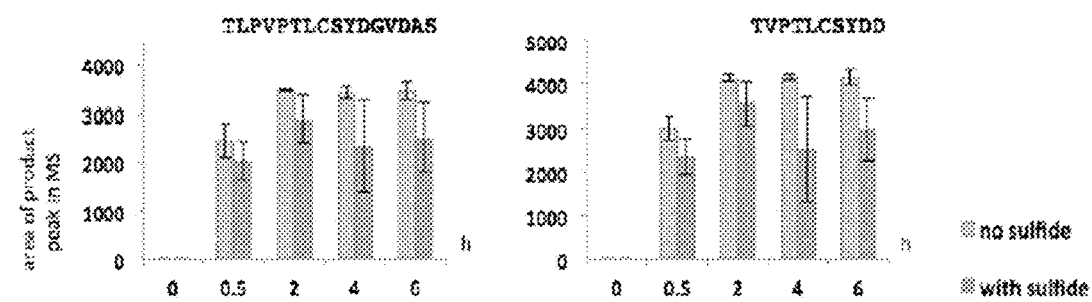
FIG. 18B is PatA proteolysis on unmodified TruE-3-2.
Figure 18C:
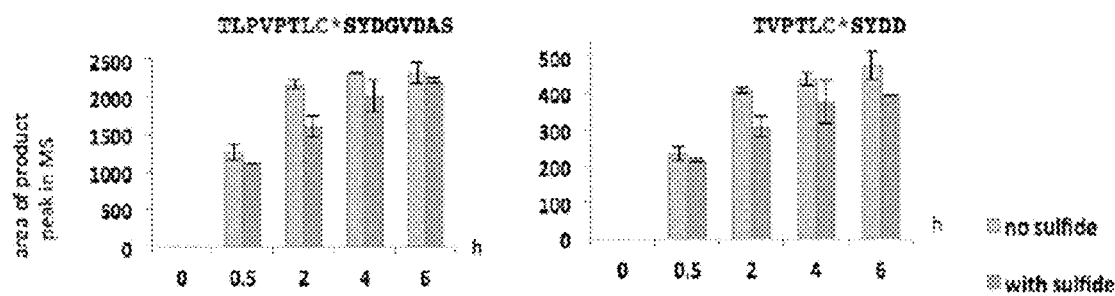
FIG. 18C is PatA proteolysis on heterocyclic TruE-3-2.
Figure 18D:
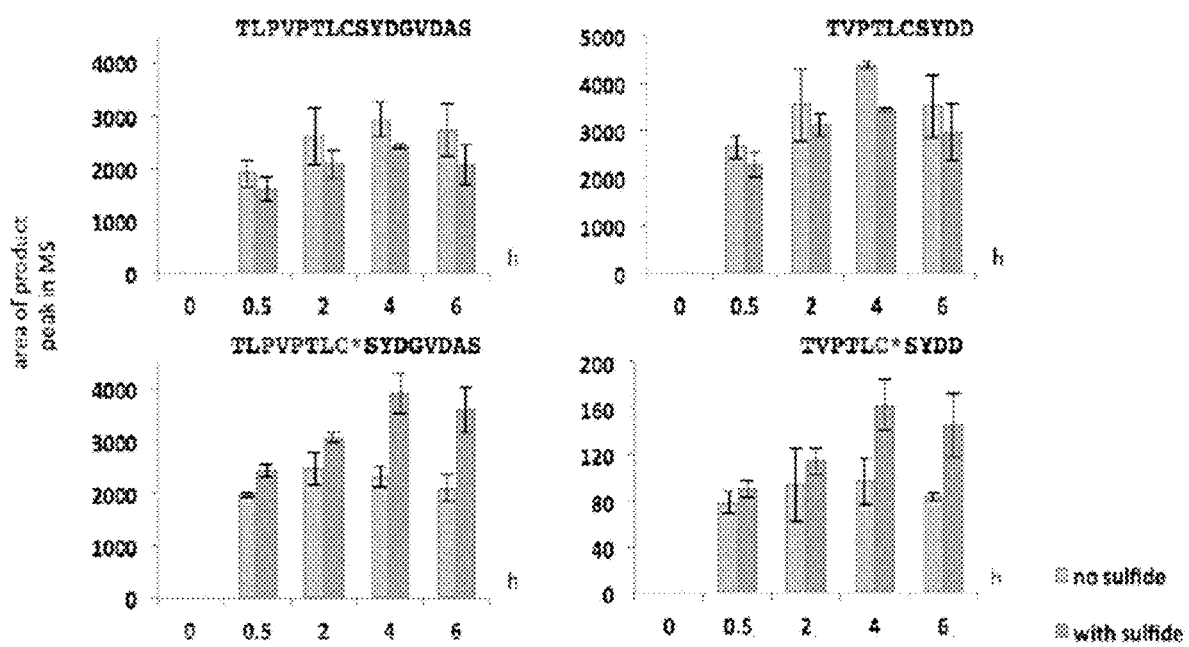
FIG. 18D is PatA proteolysis on unmodified TruE-3-2 in presence of ThcD. As observed, the correct PatA intermediates were produced more in presence of sulfide than without (see FIG. 9).
Figure 18E:
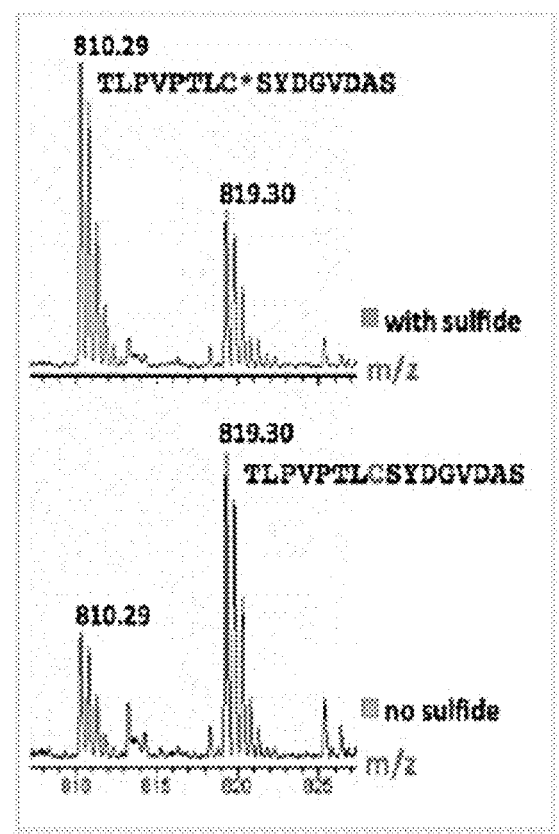
FIG. 18E is the corresponding mass spectrum at a longer 24 h time-point showing the correct vs. incorrect intermediate.
Figure 18F:
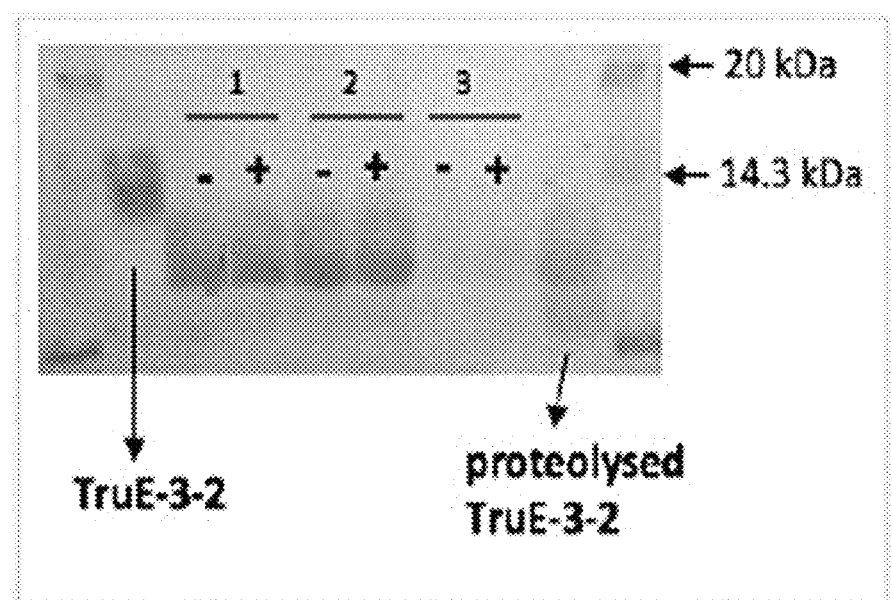
FIG. 18F shows further confirmation of the proteolysis by SDS-PAGE analysis of the 30 m time-point of PatA reactions from each of the above set, namely PatA on TruE-3-2 (1), TruE-3-2+ThcD (2) and heterocyclized TruE-3-2 (3). At the 30 m time point cleavage at the first cassette has occurred as judged from appearance of the species TLPVPTLC*SYDGVDASTVPTLC*SYDD (where C*=thiazoline) (SEQ ID NO: 4) or TLPVPTLCSYDGVDASTVPTLCSYDD (SEQ ID NO: 5) on the corresponding mass spectrum, which gradually disappears as it is further cleaved at the second cassette. Shown at the extreme left and right are protein markers. Each data-point at every time-point is an average of duplicates and error bars represent standard deviation. Effect of sulfide on C-terminal proteolysis/macrocyclization.
Figure 18G:
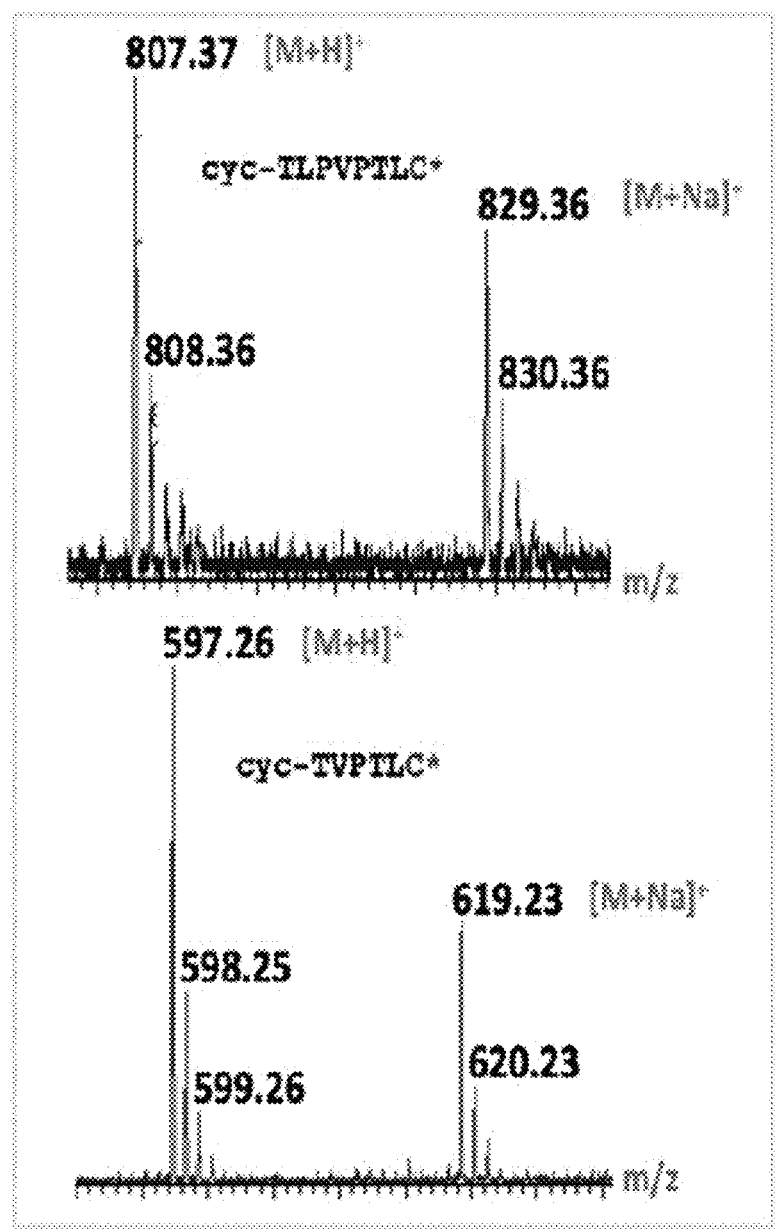
FIG. 18G and FIG. 18H show that to generate sufficient substrate for TruG reaction, a 1.0 mL scale of ThcD reaction with TruE-3-2 was set up. This was purified by HPLC and used with PatA reaction to generate cleaved products. Further purification by C18 resin yielded the pure TLPVPTLC*SYDGVDAS (SEQ ID NO.
Figure 18H:
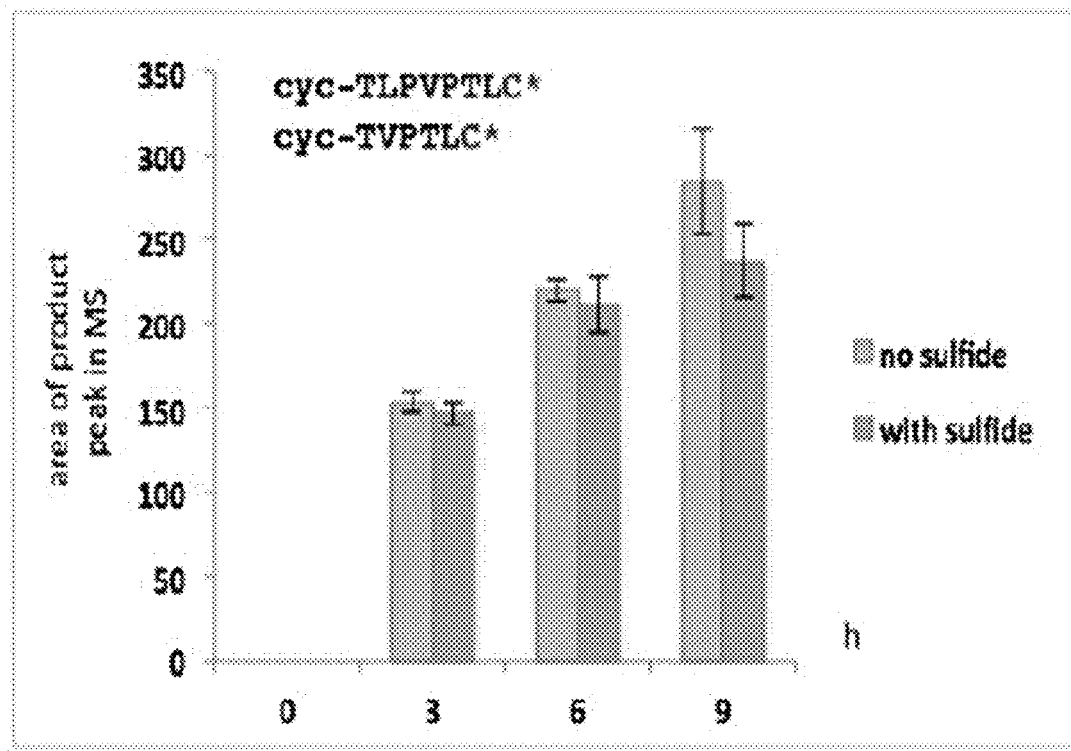

Molecular mechanism 2: metabolism is not altered significantly by cysteine. ATP is used in heterocyclization, so that its concentration might affect the pathway. Other metabolites might affect the pathway indirectly. Two types of metabolomics experiments were used. The first examined a panel of key primary metabolites using authentic standards, such as ATP and NADH (FIG. 3D and FIG. 17A-FIG. 17C). No significant differences were observed except with redox-responsive metabolites, which were greatly altered. Second, untargeted LC-MS was performed and interrogated by principal component analysis (PCA) and using self-organizing maps (FIG. 17D). Using these latter methods, only minor differences were observed.

Figure 11C:
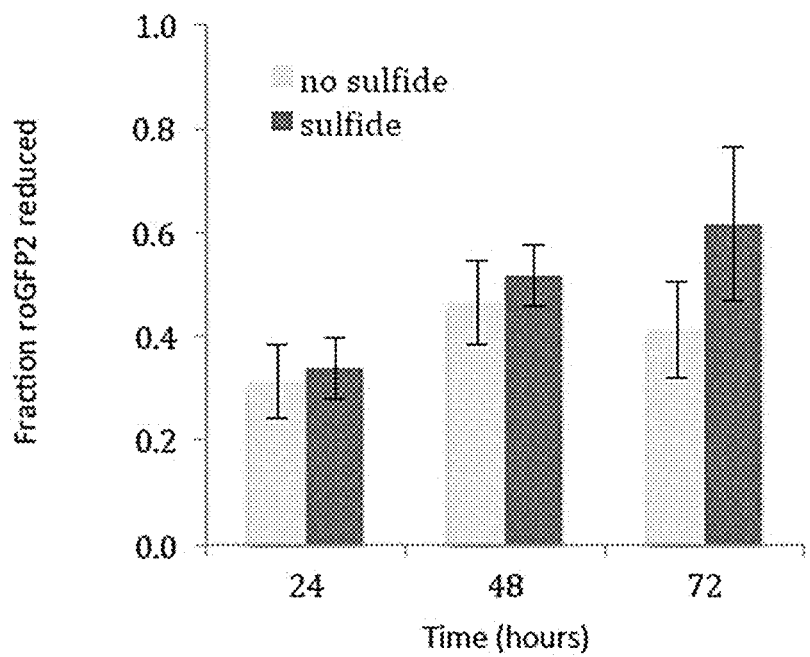
FIG. 11C shows that the addition of sulfide (phosphate buffer pH 8, 10 mM $Na_2S$) leads to modest reduction of roGFP2.
Figure 11D:
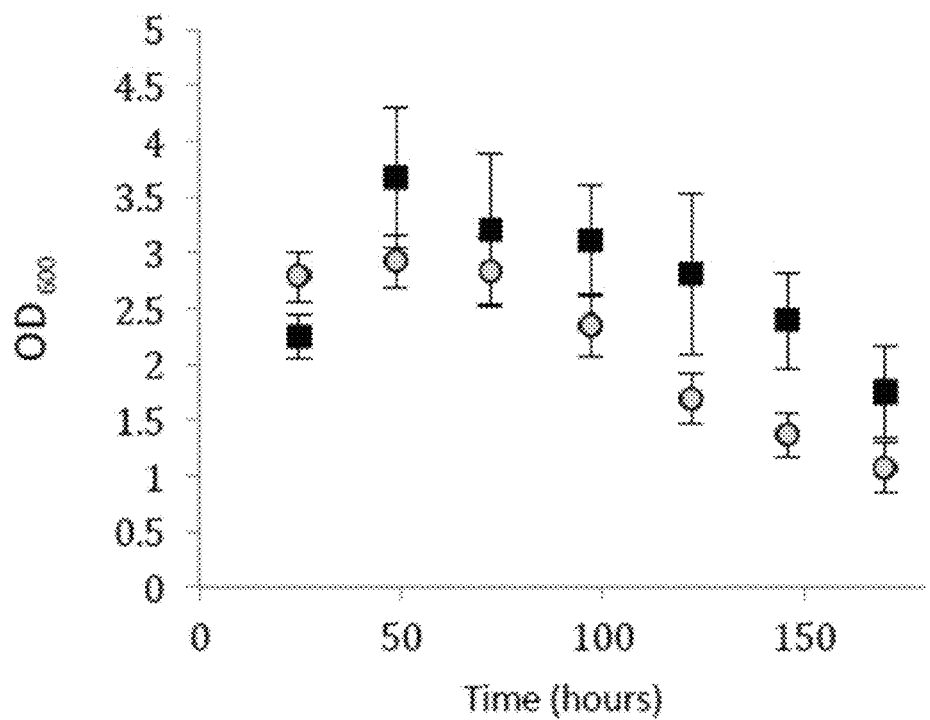
FIG. 11D shows the OD600 measurement of cultures shown in FIG. 3B.
Figure 11E:
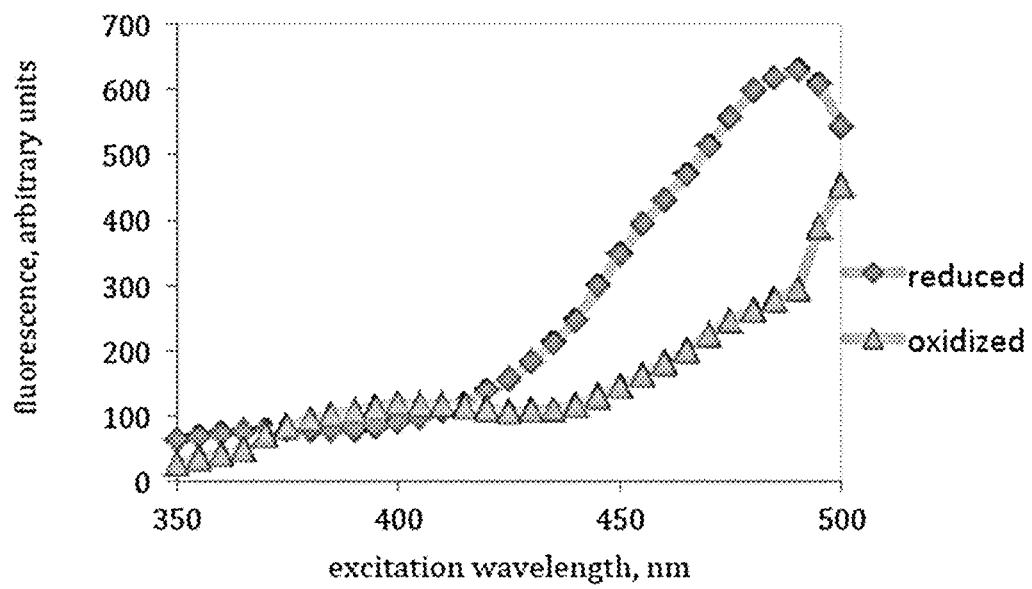
FIG. 11E is the fluorescence spectra of reduced and oxidized roGFP2 expressed from pRSFlac-roGFP2 in *E. coli*. Excitation spectra were measured from single wells in the experiment shown in FIG. 3B. Emission wavelength was 520 nm.

Molecular mechanism 3: cellular redox is not responsible for the effect. Because of the great change of cellular redox, where cysteine led to greatly increased glutathione disulfide, it was possible that a change in redox increased the yield of products. Cysteine oxidizes *E. coli* both by metabolomics and by following redox sensitive GFP, showing that cysteine greatly increases cytoplasmic oxidation (FIG. 3E and FIG. 17A-FIG. 17C). However, $H_2S$ was equally effective in producing patellins, yet instead of oxidizing cells it mildly reduced the cytoplasm (FIG. 11C). Moreover, $H_2S$ and cysteine were both equally effective at producing patellins in aerobic and anaerobic fermentation. Therefore, a change in cellular redox did not cause increased patellin production.

Molecular mechanism 4: modulation of protein activity underlies the cysteine effect. Although gross cellular redox does not correlate with increased patellin production, the redox state of individual thiols in proteins changes with increased intracellular $H_2S$. It was observed that the higher the yield of patellin 2 in a culture, the more cysteine-dependent that yield became. One out of the many examples can be seen in FIG. 3B, where introduction of a His-tag to TruE-2-2 decreases the yield of patellin 2 in comparison to the unmodified vector; more patellin 2 is produced without cysteine with this His-tagged vector. Therefore, a pTru plasmid-encoded protein may act as a negative regulator of compound synthesis that is relieved by addition of sulfide.

Figure 4A:
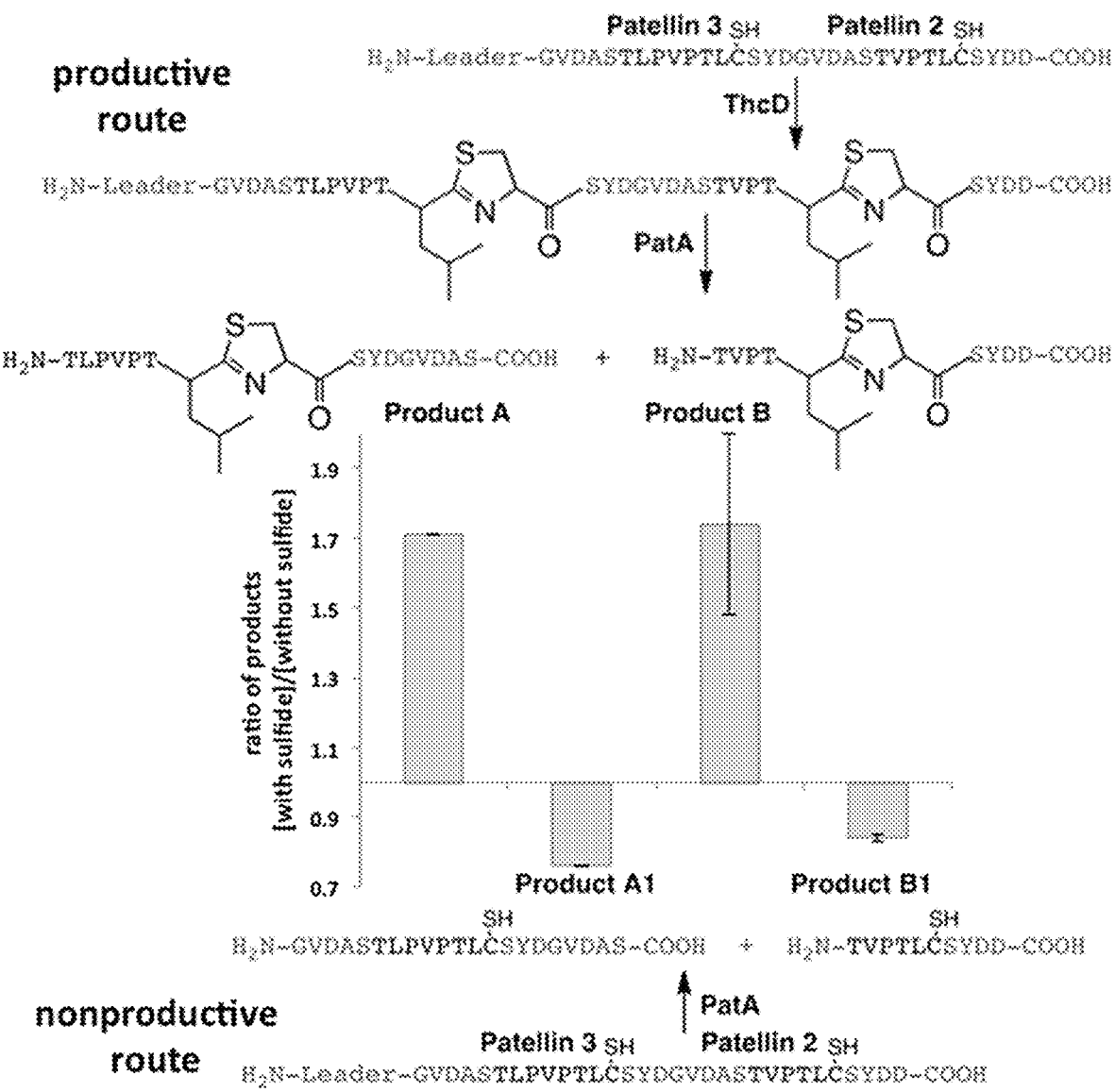
FIG. 4A shows a ratio, wherein more of the correct products A and B are obtained when sulfide is added to the enzyme reaction mixture. By contrast, a lower amount of products A1 and A2 are obtained with sulfide; these products are not substrates for macrocyclization.
Figure 4B:
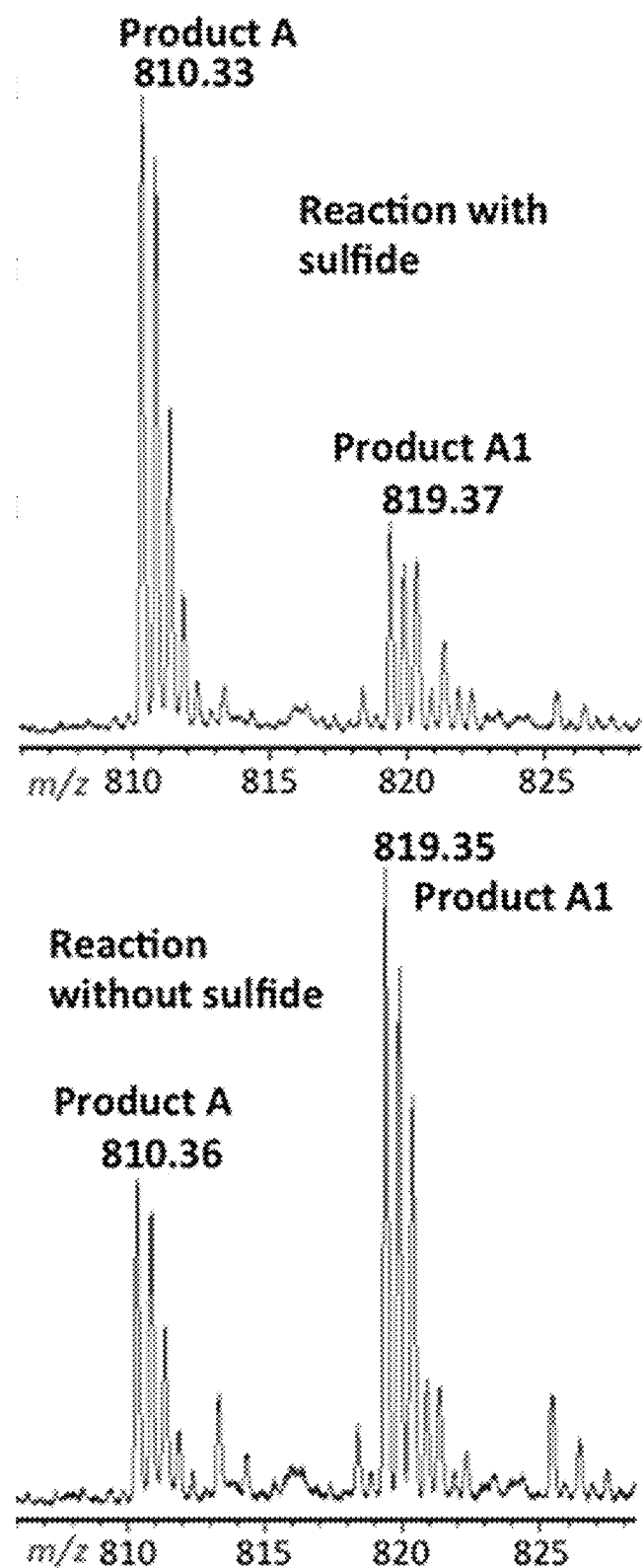
FIG. 4B shows mass spectra for Product A and Product A1 with and without the addition of sulfide to the media.

One possible negative regulator is the enzyme TruA, which is redox sensitive and which is the only enzyme in the pathway that is capable of derailing the biosynthesis by making nonproductive intermediates. This hypothesis was tested by combining the relevant proteins in vitro and determining the effect of sulfide on product formation. TruE-3-2 was treated with the TruD homolog ThcD and PatA (98% identical to TruA) in the presence or absence of 500 µM sulfide. The relative enzyme rates were not significantly affected in the presence or absence of sulfide. However, absent sulfide mainly the incorrect products that are made when PatA acts prior to action of ThcD were observed (FIG. 4, FIG. 18). With sulfide, by contrast, mostly correct products were made when ThcD acted before PatA. When PatA or ThcD were used singly with their authentic substrates, they performed without significant differences with or without the addition of 500 µM sulfide, indicating that this effect was not due to gross inhibition of enzymes or a change in the fundamental properties of enzymes or substrates. Sulfide may specifically modulate the substrate preference of mature enzymes in the cyanobactin pathway, enabling posttranslational control of product formation in vivo.

Figure 19:
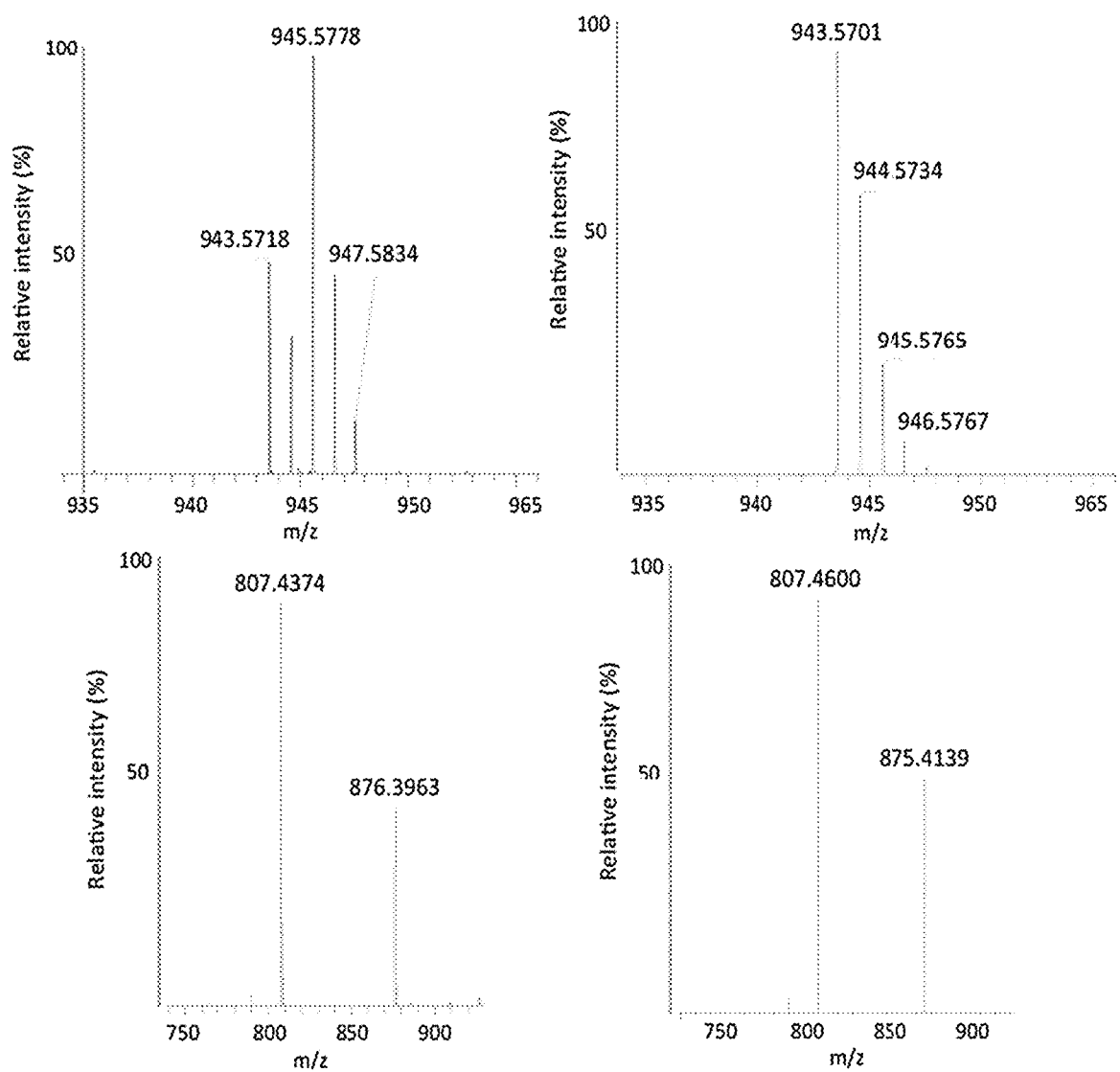
FIG. 19 shows incorporation of 1-$^{13}$C-DMAPP into cyanobactins. Left panel shows the 2 Dalton shift in the mass of patellin 3 upon addition of labeled DMAPP (top) and the MS/MS fragmentation (bottom). Right panel shows the spectrum of unlabeled patellin 3 and the MS/MS fragmentation.

DMAPP from mev pathway is incorporated into patellins. The inventors also examined the role of mevalonate in increasing compound synthesis. $E.$ $coli$ normally contains only the deoxyxylulose pathway to isoprenoids, and therefore cannot use mevalonate in the synthesis of DMAPP.14 When $1$-$^{13}C$ labeled mevalonate was added to the culture, MS analysis showed that the major ion of the doubly prenylated peak was +2 Da in comparison to unlabeled material. In MS/MS experiments, isoprene fragments led to a loss of 69 Da rather than the usual 68 Da, indicating that the increased mass observed was solely due to isoprene and not to incorporation into the peptide backbone and that mevalonate-derived DMAPP was incorporated into patellins (FIG. 19).

Example 4

Figure 5A:
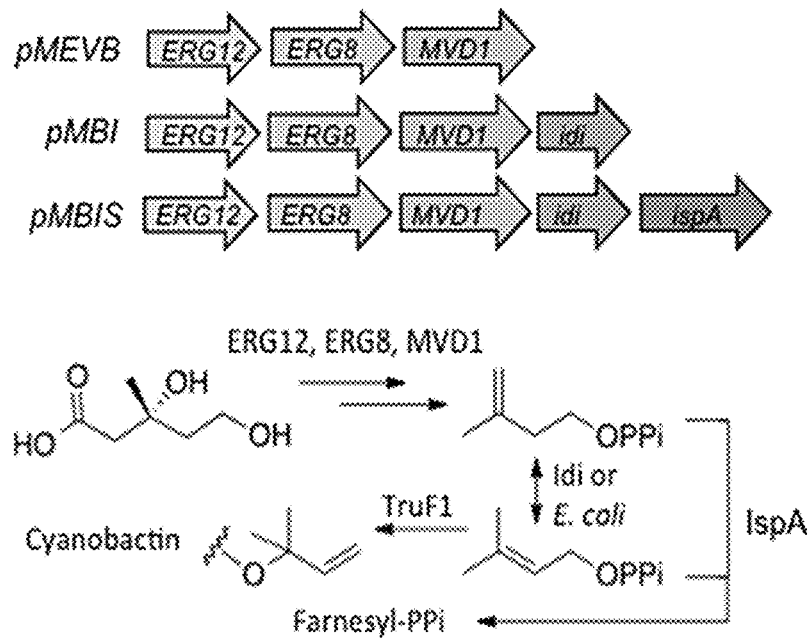
FIG. 5A shows pathways for conversion of mevalonate to DMAPP, the precursor for prenylation of cyanobactin RiPPs. The top diagram shows which genes are present in plasmids containing the mevalonate pathway, while the middle shows the biochemical process catalyzed by the enzymes that convert mevalonate to DMAPP and other products. Bottom: cyanobactin RiPP production is greatest in the presence of mevalonate. This effect requires cysteine. Cultures were grown as described and were harvested after 5 days. Each set represents triplicate independent replicates. Expression conditions: A, tru; B, tru/pBBR; C, tru/mevb; D, tru/mbi; E tru/mbis.
Figure 5A:
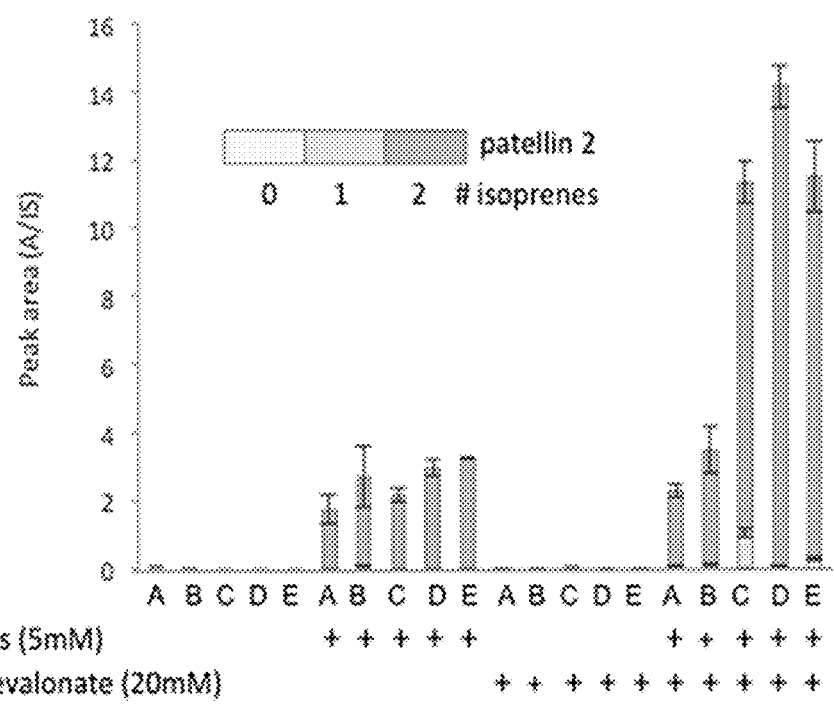
Figure 5B:
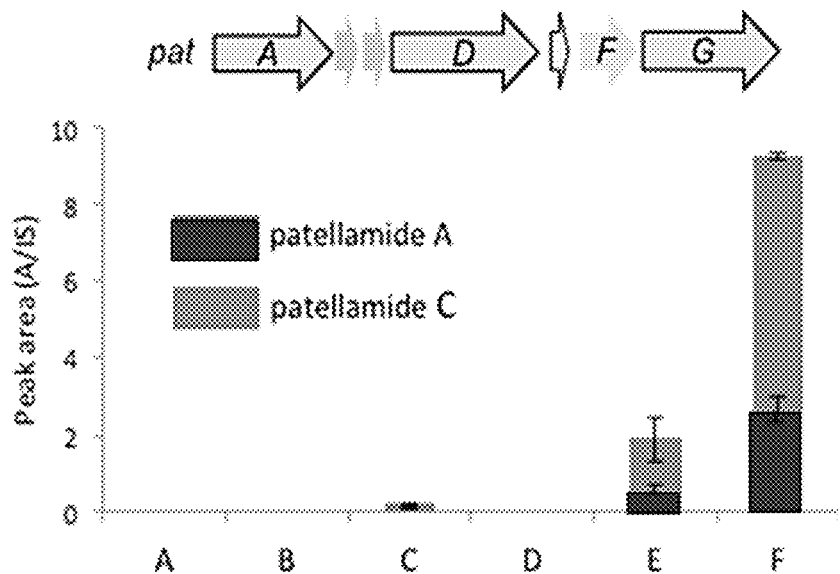
FIG. 5B is expression from the pat pathway is increased with pMBI and mevalonate, even though patellamides A and C are not prenylated. Expression conditions: A, pat; B, pat+5 mM cysteine; C, pat/mbi+5 mM cysteine; D, pat/mbi+10 mM mevalonate; E, pat/mbi+5 mM cysteine+5 mM mevalonate; F, pat/mbi+5 mM cysteine+10 mM mevalonate.

Effect of mevalonate is surprisingly independent of prenylation. The reaction rates of purified RiPP pathway enzymes either alone or in combination are not affected by increased DMAPP concentration. Using a series of vectors leading to different isoprene products demonstrated that the increased yield could be observed no matter whether DMAPP, isopentenyl pyrophosphate, or farnesyl pyrophosphate was the primary product of the pathway (FIG. 5A). The pat pathway, which is closely related to tru except that it lacks a functional prenyltransferase, was also expressed. Nonetheless, pat was still strongly responsive to both cysteine and mevalonate/mev, and in fact required both in order to be detected at reasonable levels (FIG. 5B). This represents the first robust expression of the pat pathway to patellamides.

Figure 5C:
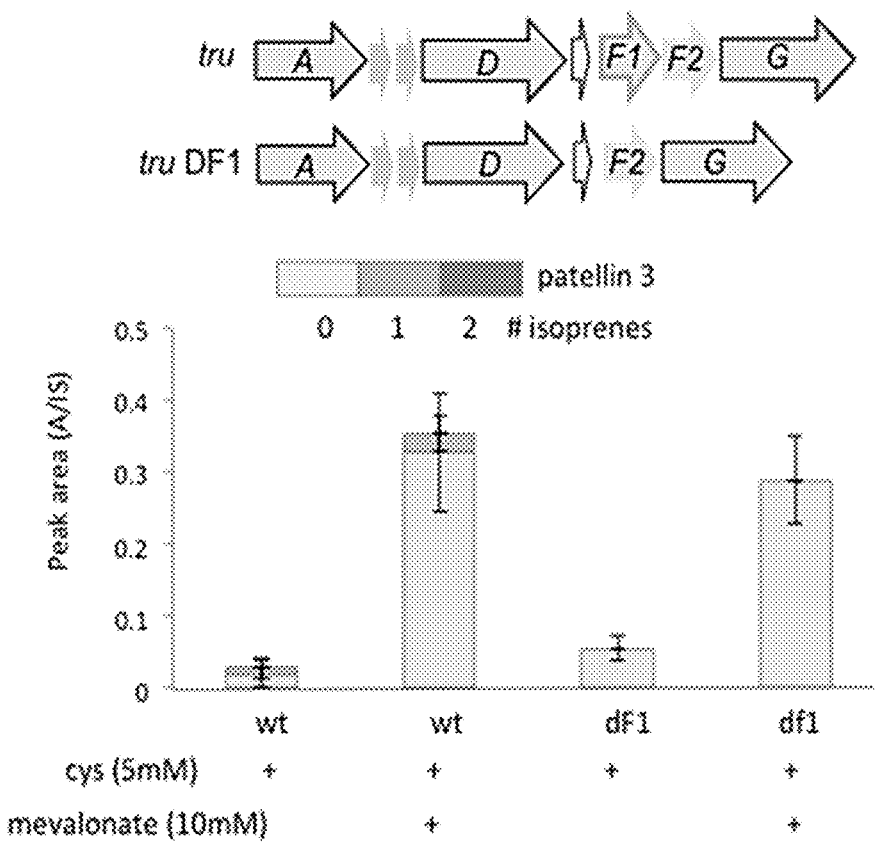
FIG. 5C is expression from the tru pathway is increased with pMBI and mevalonate, even in the absence of prenylation. pTru-b and pTru-DF1 were expressed as described. Cultures were harvested after 5 days and were analyzed for patellin production. wt: wild type; df1: TruF1 knockout. TruF2 and TruF1-TruF2 were also deleted, providing a similar effect. Note the absence of prenylated products when truF1 is removed from the tru pathway.

In addition, the tru prenyltransferase gene truF1 and its non-prenylating homolog truF2 were knocked out individually or in tandem from the tru pathway (FIG. 5C). In all cases, production was still responsive to both cysteine and mevalonate. A caveat was that this production was challenging to observe for the truF1-truF2 double knockout, which yielded a low amount of patellins. Of note, TruF2 is not a prenyltransferase in vivo, and TruF1 is solely responsible for prenylation in the pathway. In sum, in vivo and in vitro experiments demonstrated that increased prenylation within the tru (or pat) pathway was not responsible for the yield increase.

Example 5

Figure 6A:
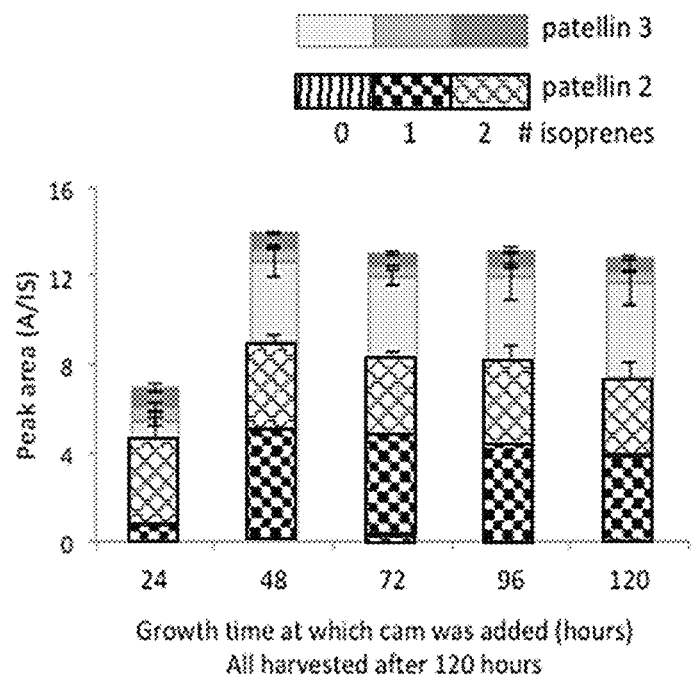
FIG. 6A shows chloramphenicol (cam) was added every 24 hr to cultures containing cysteine, and cells were harvested from all wells at 120 h. Triplicate independent measurements are shown. The resulting production of patellins after 120 h is shown.
Figure 6B:
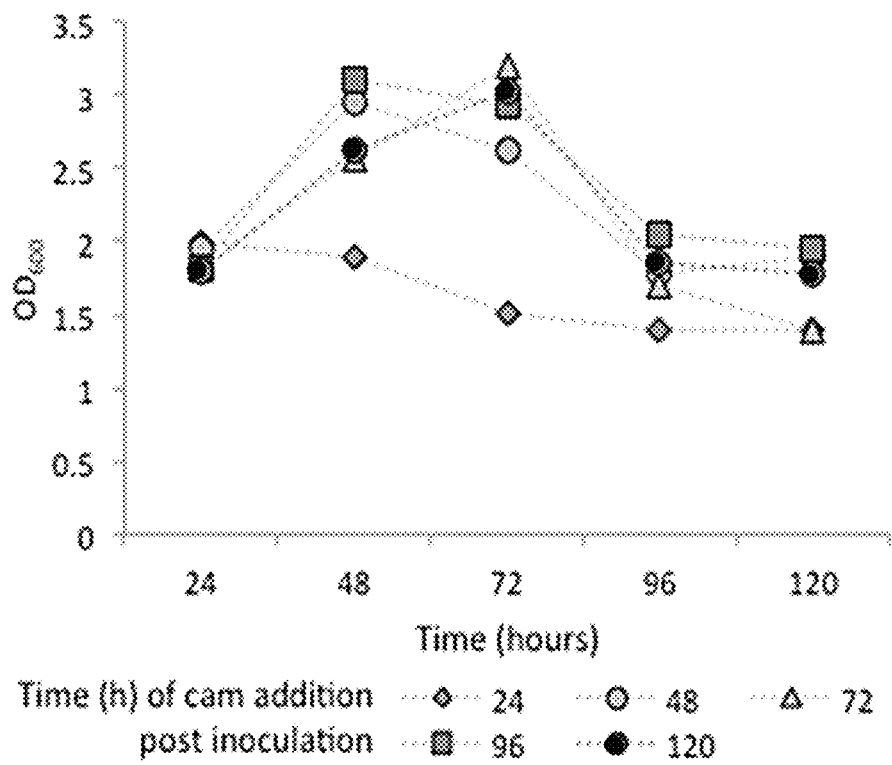
FIG. 6B shows growth curves in which OD600 was measured every 24 h. Growth ceases upon addition of chloramphenicol.

Each ensuing metabolic step is increasingly slower in vivo. The first step in the synthesis of patellins is translation of the substrate (TruE) and required enzymes. The translation inhibitor chloramphenicol was added to $E.$ $coli$ cultures every 24 h beginning at the 24 h time point (FIG. 6A-B). Cultures with and without cysteine and/or mev/mevalonate were used. Upon addition of chloramphenicol, $E.$ $coli$ growth ceased, demonstrating that translation was inhibited effectively. Addition of chloramphenicol had no effect on compound production, after correcting for chloramphenicol-caused growth defects. This indicated that transcription and translation of tru proteins is completed during cell growth. This conclusion is also supported by experiments with GFP described above, in which maximum fluorescence is achieved during log phase. By contrast, accumulation of cyclic and prenylated products continues for days after growth ceases.

Figure 14:
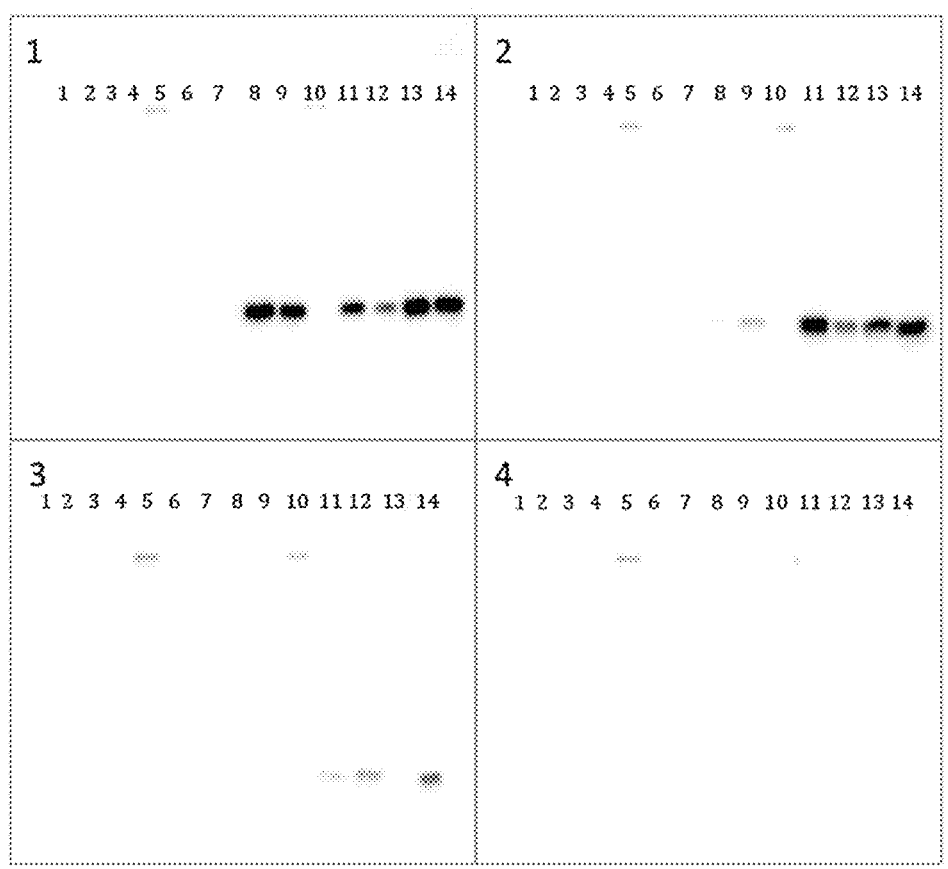
FIG. 14 shows gels and western blots of N-terminally his-tagged TruE2 expressed from pETTruE2 with pTARA. Top: western blots. Bottom: gels from the same experiment, stained with coomassie after transfer to membranes for western blots. The loading volume was normalized to approximate loading protein from 80 µl of cells from an OD600 =1 culture. Each blot/gel has a complete set of samples taken at one time point. Blot/gel 1: 6 hours, blot/gel 2: 18 hours, blot/gel 3: 31 hours, blot/gel 4: 42 hours. Gel loading (from left to right)
Figure 14:
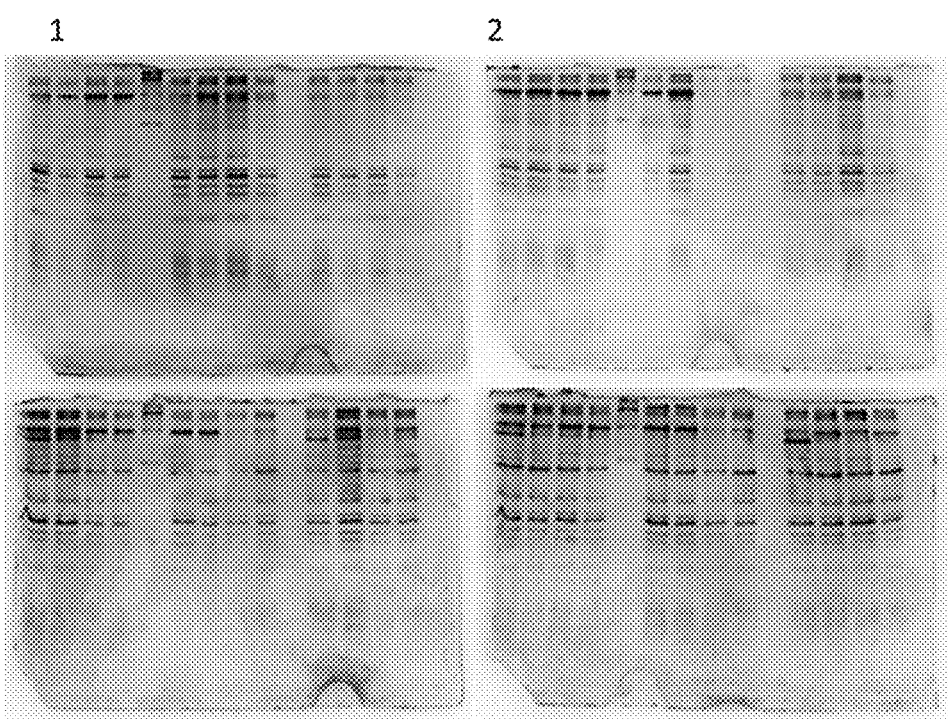
Figure 15A:
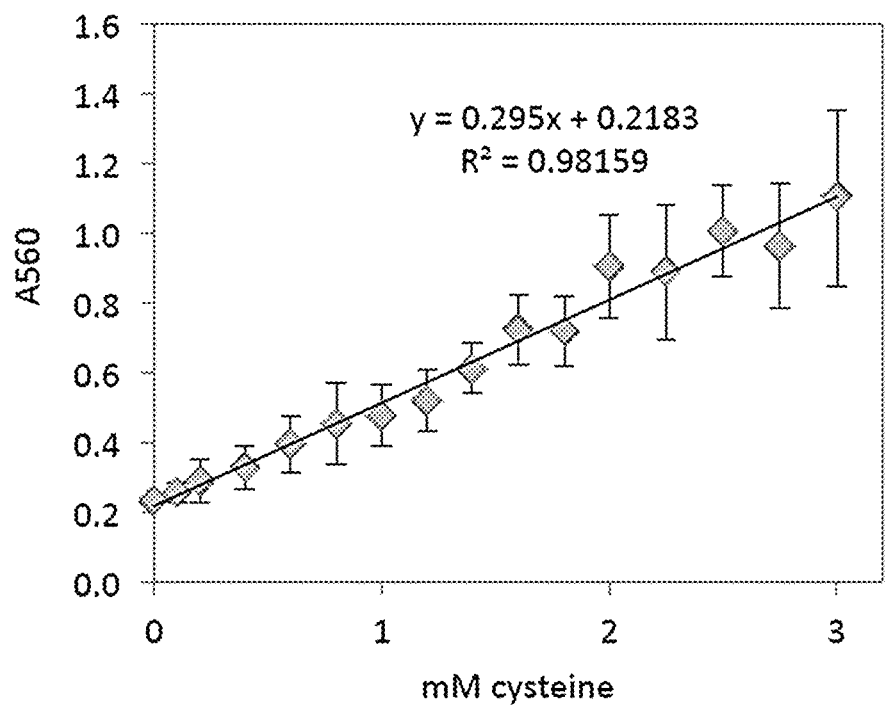
FIG. 15A shows standard curve from cysteine concentration experiments. Standards were made by adding cysteine from a 0.1 M stock solution to fresh 2xYT medium. Each point is the average of four separate standards. Error bars show standard deviations of the four measurements. The data were fit by linear regression.
Figure 15B:
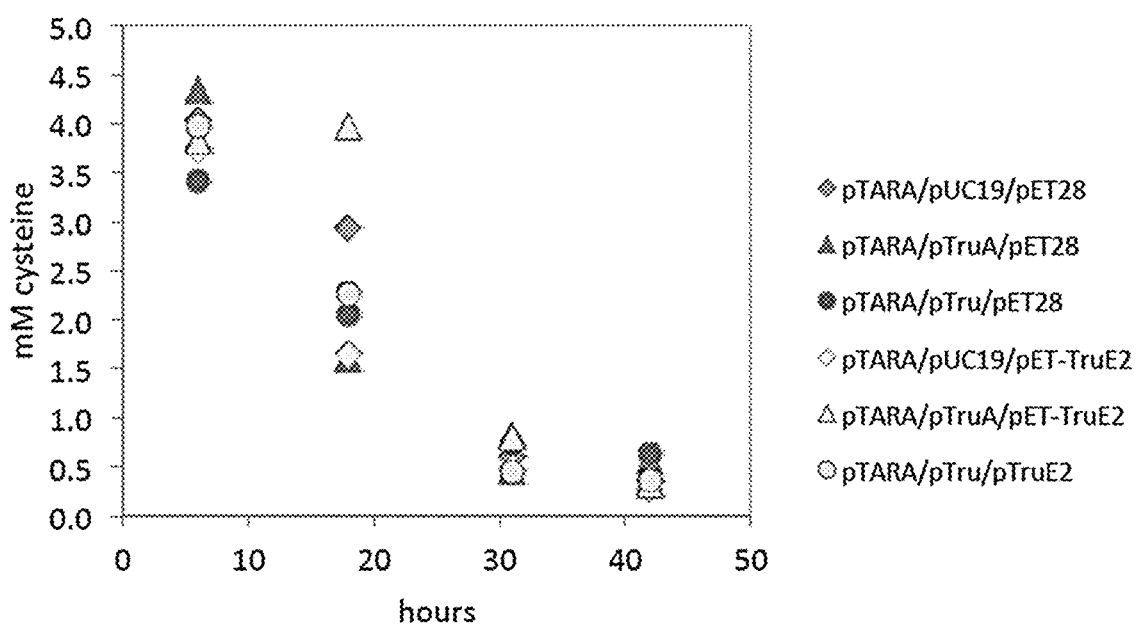
FIG. 15B shows cysteine concentrations in pET-TruE2 cultures when samples were taken for western blotting. Cysteine was measured in spent medium, as described in Methods. Each data point is the measurement from a single culture.

Following translation, TruE is heterocyclized by TruD. In western blots following TruE, TruE-2-2 was barely visible at any time point (FIG. 3C and FIG. 16), despite the fact that His-tagged TruE derivatives under control of the much stronger T7 promoter were readily visualized when T7 RNA polymerase expression was co-induced (FIG. 14). Since heterocyclization must precede the degradation of TruE, this indicated that TruE-2-2 was being consumed over the course of its synthesis, demonstrating that the first enzymatic step (heterocyclization) is fast in vivo.

Figure 6C:
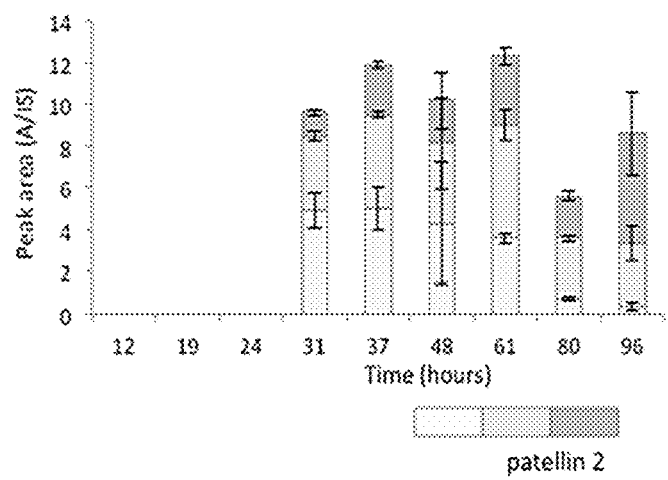
FIG. 6C shows expressions using TruE-2-2 showing the onset of macrocyclization corresponding with the depletion of cysteine as shown in FIG. 6D.
Figure 6D:
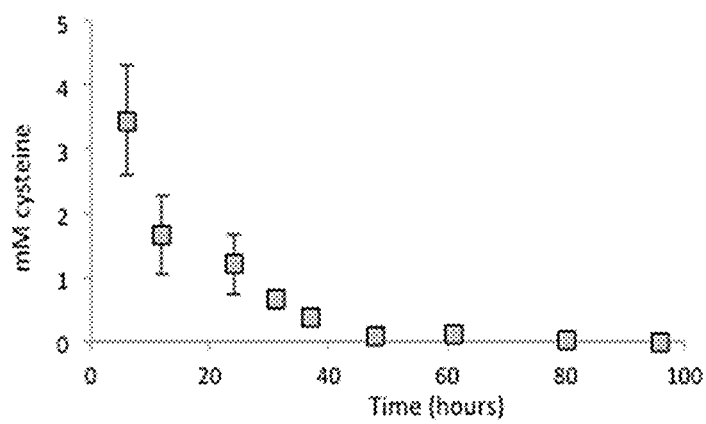
FIG. 6 shows enzymatic activity continues for days after translation stops.
FIG. 6E shows when yields are normalized, it is clear that prenylation by TruF1 continues for days and is very slow. Expressions using TruE-T-T are shown in FIG. 20B.
Figure 20B:
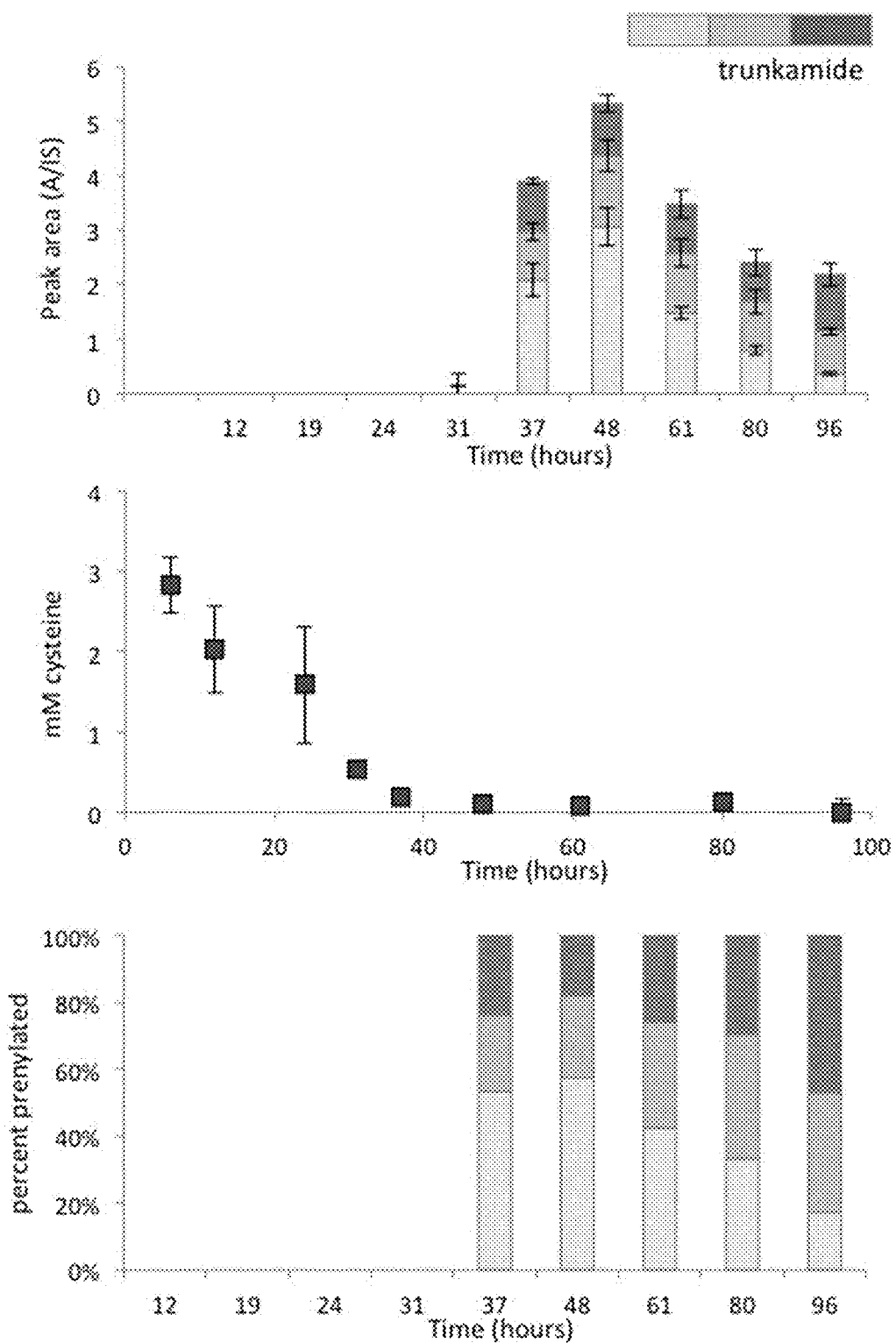
FIG. 20B shows cyclic peptide production using the TruE-T-T vector similar to results shown in FIG. 6B.

By contrast, macrocyclization was much slower. With the His-tagged TruE vector, cyclic peptide was observed at 24 h, with increasing production for a further 2 days (FIG. 3B and FIG. 20). Timing of production from the vectors containing TruE-2-2 and TruE-T-T (containing the trunkamide sequence in both cassettes) was examined (FIG. 6C-FIG. 6D, FIG. 20B). Notably, onset of cyclic peptide was observed in tandem with the timing of cysteine depletion and onset of stationary phase. Cyclic peptides continued to accumulate over approximately an additional <24 h after cysteine depletion in these conditions. Similar time courses were observed without cysteine, although much less macrocycle was produced absent cysteine. Under other conditions, such as with mev/mevalonate or with TruE-3-2, cyclic peptides continued to accumulate for up to 72 h after stationary phase. Thus, macrocyclization is slower in vivo than the preceding steps in $E.$ $coli$.

Figure 6E:
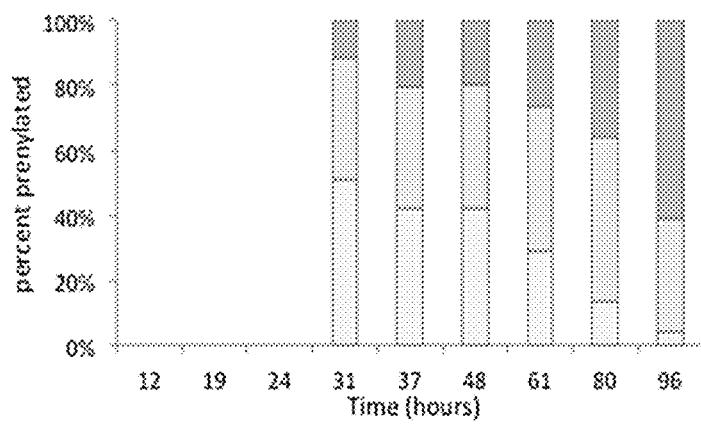

Under all conditions, prenylation continued even after the termination of the macrocyclization reaction. For example, with TruE-T-T and TruE-2-2, macrocyclization was complete by 24 h after cysteine depletion, while prenylation continued to increase until the end of the fermentation, 72 h after cysteine depletion (FIG. 6E). This effect is also seen in wild-type cyanobacteria, where prenylation can continue to occur over a period of months. Notably, this decreasing order of reaction velocity is the reverse of what one would expect for narrow-substrate pathways, where the rate-limiting step is early.

Figure 7:
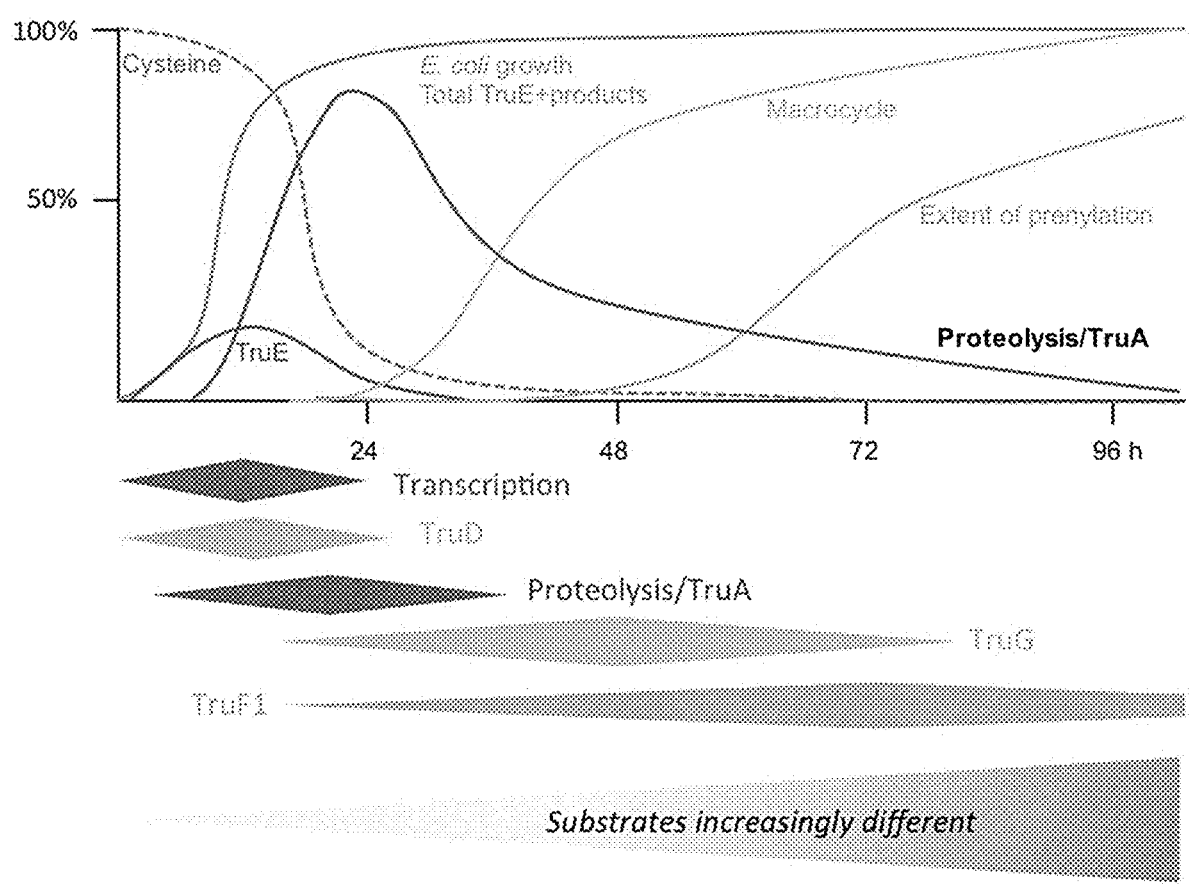
FIG. 7 shows a metabolic model for tru production. While not wanting to be bound by theory, the following model is proposed. During log phase, cyanobactin RiPP pathway proteins are expressed as cysteine is consumed. TruD must act during this time to produce heterocyclized substrate for further modification into cyanobactins. Precursor protein is degraded by *E. coli* proteases or processed by TruA during log phase as cysteine is consumed, but macrocyclized products are not detectable until cysteine is gone from the cultures. These products are slowly prenylated by TruF1. The line labeled "Proteolysis/TruA" indicates heterogeneous products that were not directly detected; all other lines indicate measured values. The diamonds at bottom show the time period in which each enzyme must be functional, indicating that each enzymatic step is progressively slower in vivo. These enzymes are also progressively slower when used in vitro, although this activity does not reflect directly the in vivo process.

The diversity-generating tru pathway exhibits a surprising property, in which each metabolic step in the pathway is progressively slower as biosynthesis proceeds in living cells. All metabolic steps except for precise timing of TruA cleavage were observed by quantifying pathway intermediates and products, leading to a metabolic flux model (FIG. 7). 1) TruE precursor peptide accumulates in early log phase. 2) TruD acts on TruE essentially immediately, prior to any proteolysis of TruE. 3) TruE is rapidly proteolyzed, completely disappearing as cysteine is depleted and log phase ends. Timing of this disappearance is identical with and without cysteine. 4) As log phase ends and cysteine is depleted, cyclic peptides accumulate slowly, requiring 24-48 h for completion. 5) Prenylated intermediates are made even more slowly, continuing to accumulate for >72 h and not being complete even at that time. Thus, each metabolic step requires a substantially longer period of time than the preceding one in vivo. This parallels the increasing differentiation of chemical substrates at each ensuing biochemical step. The mechanism is fundamentally different than what is expected for narrow-substrate pathways, where the rate-limiting step should be early to mitigate the effects of toxic intermediates or byproducts.

Example 6

Green fluorescent protein (GFP) was used as a reporter to determine how mevalonate affects tru pathway transcription. The inventors found that using the pMBI vector in tandem with added mevalonate unexpectedly led to increased production of patellins, the products of the tru pathway. Vectors encoding GFP fused either to the terminus of the tru operon under control of the lac promoter (Topo-E1-S316-GFP-F4, hereafter referred to as "pTru_gfp"; Donia et al., ChemBioChem, 12(8):1230-1236 (2011)) or encoding a redox-sensitive version of GFP (roGFP2; Hanson, et al., J. Biol. Chem. 279:13044-53 (2004)) under control of the lac promoter (pRSFlac-roGFP2; Tianero, et al., Proceedings of the National Academy of Sciences USA 113(7):1772-77, S1-S33 (2016)) were used to test whether mevalonate derivatives somehow cause the observed effect on patellin production by turning up the native regulation of the lac promoter. The pTru_gfp and pRSFlac-roGFP2 vectors were transformed into E. coli DH10B cells (Life Technologies) either with or without vector pMBI, which enables cells to convert mevalonate into isopentenyl pyrophosphate and DMAPP. If mevalonate derivatives simply upregulate the lac promoter, increased fluorescence in both the pTru_gfp and pRSFlac-roGFP2 samples when both mevalonate and pMBI were present would be expected.

Replicate colonies for each transformation (pTru-SD alone, pTru-SD with pMBI, pTru_gfp alone, pTru_gfp with pMBI, pRSFlac-roGFP2 alone, and pRSFlac-roGFP2 with pMBI) were inoculated into 2xYT broth (6 mL) in 24-well deep-well plates with antibiotics (pTru_gfp, ampicillin: 50 µg/mL; pMBI, tetracycline: 5 µg/mL; pRSFlac-roGFP2, kanamycin: 50 µg/mL) at 30° C. overnight. To the combined seed cultures was added an equal volume of 60% (v/v) glycerol, and stocks were stored at −80° C. For expression, seed cultures (0.2% v/v) from each of the glycerol stocks were inoculated to fresh 2xYT medium (5 mL) with antibiotics.

Mevalonolactone (2 M) was hydrolyzed to mevalonate with 1:1 (v/v) KOH (2 M) based on a published method. Martin, V. J. J., Pitera, D. J., Withers, S. T., Newman, J. D., and Keasling, J. D. (2003) Engineering a mevalonate pathway in Escherichia coli for production of terpenoids, Nature Biotechnology, 21, 796-802. Mevalonate (0, 1,5, 10, 20, or 30 mM) was added to triplicate replicates of E. coli cultures in 2xYT broth supplemented with cysteine (10 mM). The cultures (pTru-SD alone, pTru-SD with pMBI, pTru_gfp alone, pTru_gfp with pMBI, pRSFlac-roGFP2 alone, and pRSFlac-roGFP2 with pMBI) were incubated at 30° C. for 5 days with shaking at 150 rpm. Both GFP fluorescence and OD600 were measured every 12 h or 24 h. Harvested cells were washed and suspended with phophate-buffered saline solution (100 µL; 137 mM NaCl, 2.7 mM KCl, 10 mM $Na_2HPO_4$, 2 mM $KH_2PO_4$).

Fluorescence was read on a microplate reader (Molecular Devices). For cells containing pTru_gfp, fluorescence was read on with excitation wavelength of 395 nm and emission wavelength of 509 nm. For cells with pRSFlac-roGFP2, excitation wavelengths were 400nm and 490 nm and emission wavelength was 520 nm. Fluorescence intensity was normalized to the OD600 of the culture.

Figure 21A:
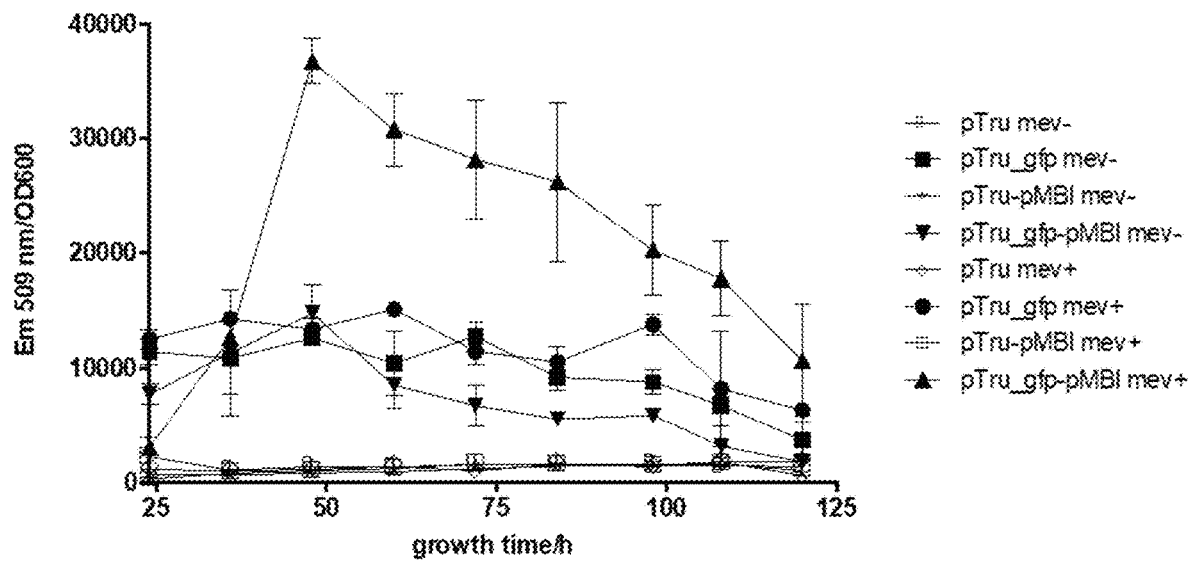
FIG. 21A shows relative fluorescence intensity with and without 20 mM mevalonate.
Figure 21B:
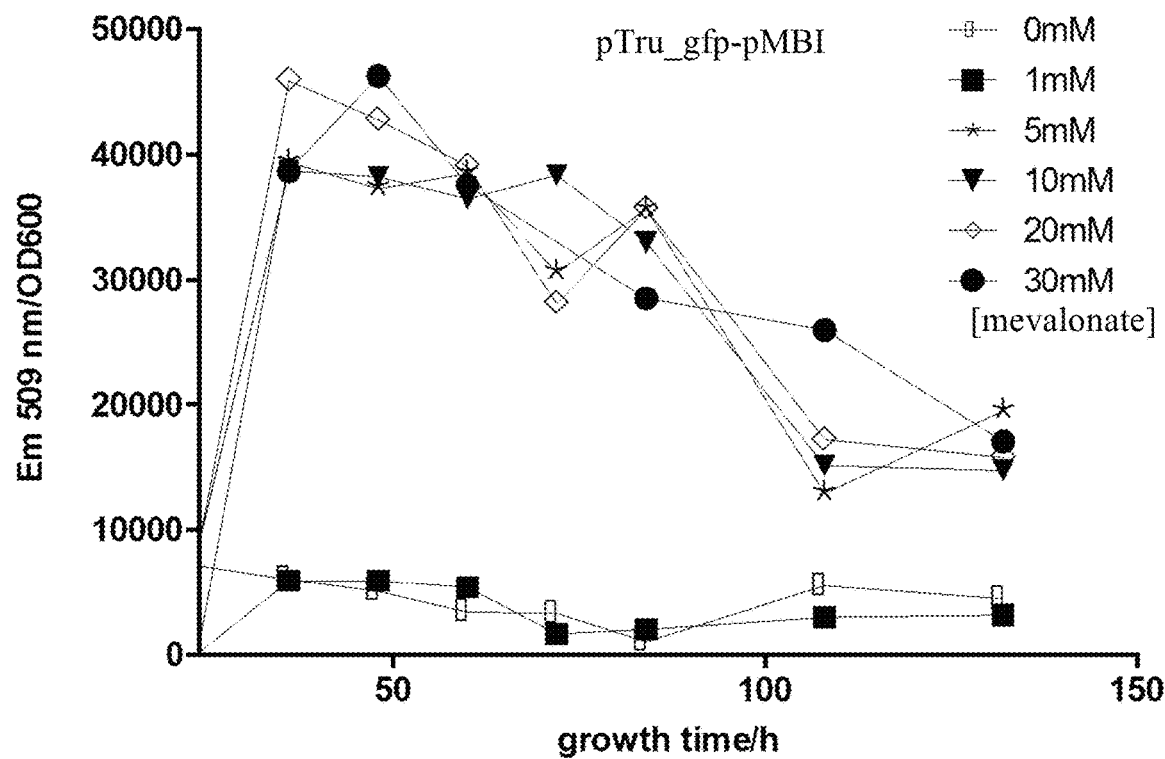
FIG. 21B shows the relative fluorescence intensity of pTru_gfp-pMBI with 0, 1, 5, 10, 20, 30 mM mevalonate.
Figure 21C:
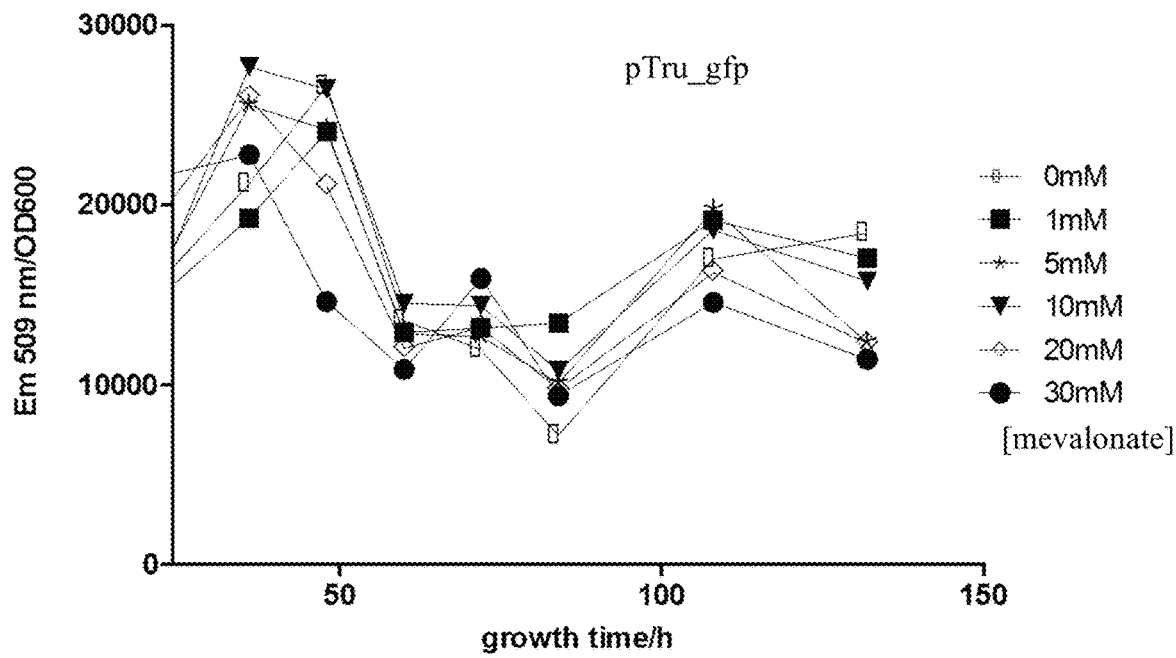
FIG. 21C shows relative fluorescence intensity of pTru_gfp with 0, 1, 5, 10, 20, 30 mM mevalonate.
Figure 21D:
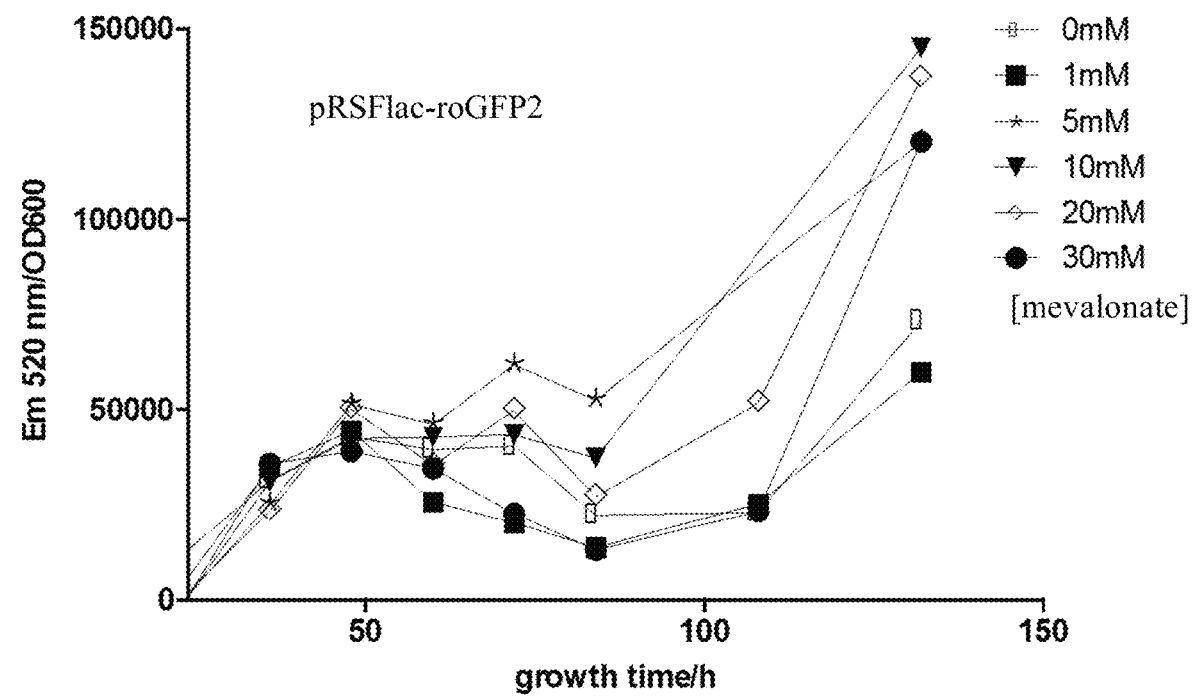
FIG. 21D shows relative fluorescence intensity of pRSFlac-roGFP2 with 0, 1, 5, 10, 20, 30 mM mevalonate.

The results show that expression of pTru_gfp was affected by mevalonate only in the presence of mevalonate pathway proteins (supplied here by pMBI) (FIG. 21A-FIG. 21C), and that the effect of mevalonate was not observed for all lac-driven constructs but instead specific to constructs expressing tru (compare FIG. 21B with FIG. 21D).

Figure 22A:
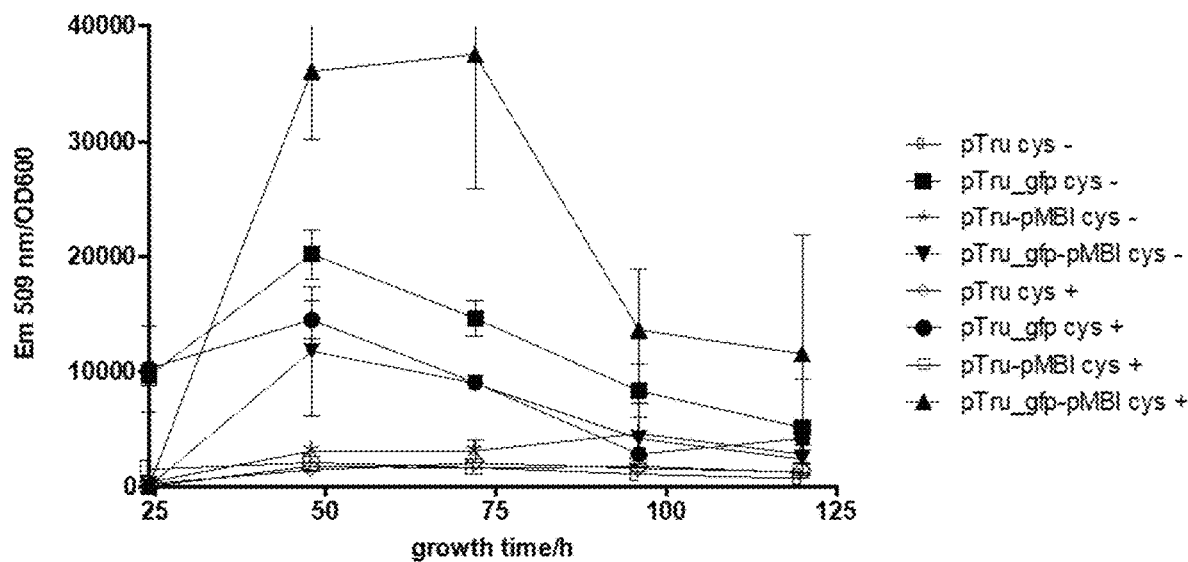
FIG. 22A shows relative fluorescence intensity with and without cysteine (10 mM).
Figure 22B:
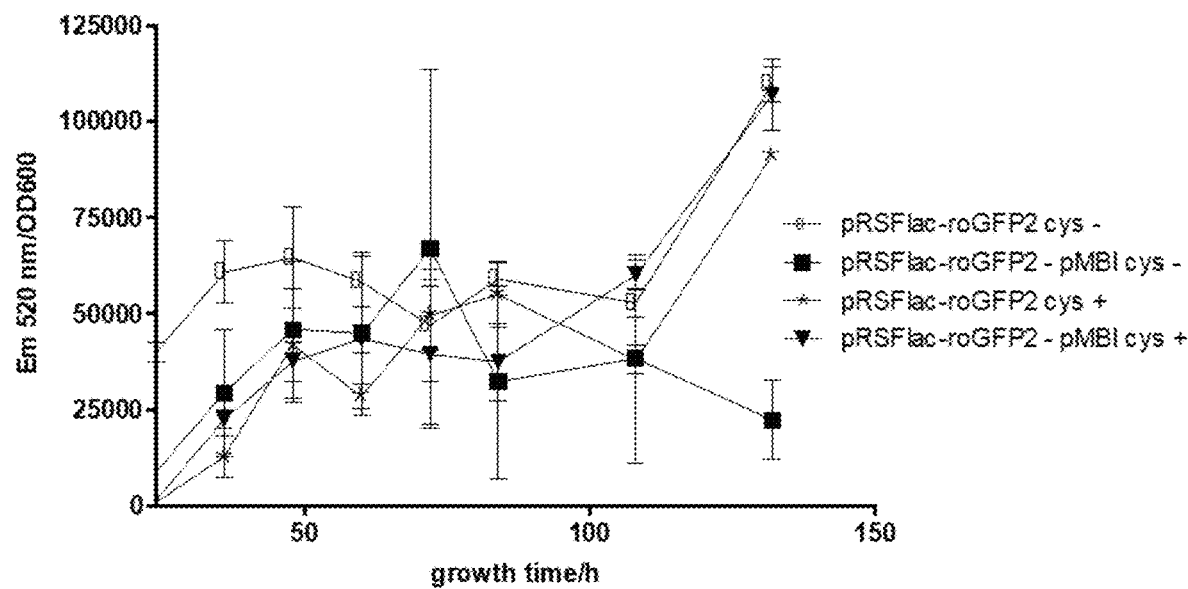
FIG. 22B shows relative fluorescence intensity of pRSFlac-roGFP2 with and without cysteine (10 mM).

Additional experiments tested whether the effect of mevalonate relies on the addition of a sulfide source, such as cysteine. Cultures were grown as described above except that mevalonate (20 mM) was added to all samples, and samples were prepared both with and without cysteine (10 mM). Samples were then measured as described above. The results demonstrated that the activating effect of mevalonate and mevalonate pathway proteins on tru expression depends on the presence of a sulfide source (FIG. 22).

The results confirm that the amounts of tru pathway proteins increase in the presence of mevalonate and mevalonate pathway proteins in a dose-dependent manner, but only when cysteine is present. By contrast, expression from an analogous construct lacking tru, pRSFlac-roGFP2, is not increased by cysteine, mevalonate, or pMBI, or any combination thereof. Surprisingly, the observed effects on tru expression obtained by providing mevalonate and mevalonate pathway proteins do not work through a general effect on lac transcription but rather directly affect transcription, translation, and/or stability of cyanobactin pathway proteins such as tru proteins. It is surprising and unexpected that activity of the mev pathway would have such a pronounced effect increasing production of proteins in an unrelated pathway such as tru.

6. CLAUSES

Clause 1. A method for producing a ribosomally synthesized and posttranslationally modified peptide (RiPP), comprising culturing a recombinant cell in the presence of an exogenous sulfide source, wherein the recombinant cell comprises a nucleic acid encoding a tru protein or a pat protein.

Clause 2. The method of clause 1, wherein the exogenous sulfide source comprises cysteine.

Clause 3. The method of clause 2, wherein cysteine is provided at a concentration of 0.5-40 mM.

Clause 4. The method of clause 2, wherein cysteine is provided at a concentration of 5-10 mM.

Clause 5. The method of clause 1, wherein the exogenous sulfide source comprises cystine.

Clause 6. The method of clause 1, wherein the exogenous sulfide source comprises hydrogen sulfide.

Clause 7. The method of clause 1, wherein the exogenous sulfide source comprises sodium hydrosulfide.

Clause 8. The method of clause 1, wherein the recombinant cell comprises a nucleic acid encoding a tru protein.

Clause 9. The method of clause 8, wherein the recombinant cell expresses TruA, TruB, TruC, TruD, TruF1, TruF2, and TruG.

Clause 10. The method of clause 1, wherein the recombinant cell comprises a nucleic acid encoding a pat protein.

Clause 11. The method of clause 10, wherein the recombinant cell expresses PatA, PatB, PatC, PatD, PatF, and PatG.

Clause 12. The method of clause 1, wherein the recombinant cell comprises a nucleic acid encoding at least one tru protein and at least one pat protein.

Clause 13. The method of clause 1, wherein the recombinant cell is *Escherichia coli*.

Clause 14. The method of clause 1, wherein the recombinant cell expresses a TruE variant.

Clause 15. The method of clause 1, wherein the recombinant cell expresses a PatE variant.

Clause 16. The method of clause 1, wherein the recombinant cell further comprises a nucleic acid encoding a mev protein.

Clause 17. The method of clause 16, wherein the recombinant cell is cultured in the presence of exogenous mevalonate.

Clause 18. A method for producing a ribosomally synthesized and posttranslationally modified peptide (RiPP), comprising culturing a recombinant cell in the presence of exogenous mevalonate, wherein the recombinant cell comprises a nucleic acid encoding a tru protein or a pat protein, and wherein the recombinant cell comprises a nucleic acid encoding a mev protein.

Clause 19. The method of clause 18, wherein the recombinant cell expresses ERG12, ERG8, and MVD1.

Clause 20. The method of clause 18, further comprising culturing the recombinant cell in the presence of an exogenous sulfide source.

Clause 21. The method of clause 20, wherein the exogenous sulfide source comprises cysteine.

Clause 22. The method of clause 21, wherein cysteine is provided at a concentration of 0.5-40 mM.

Clause 23. The method of clause 21, wherein cysteine is provided at a concentration of 5-10 mM.

Clause 24. The method of clause 20, wherein the exogenous sulfide source comprises cystine.

Clause 25. The method of clause 20, wherein the exogenous sulfide source comprises hydrogen sulfide.

Clause 26. The method of clause 20, wherein the exogenous sulfide source comprises sodium hydrosulfide.

Clause 27. The method of clause 18, wherein the recombinant cell expresses a TruE variant.

Clause 28. The method of clause 18, wherein the recombinant cell expresses a PatE variant.

Clause 29. The method of clause 18, wherein the exogenous mevalonate is provided at a concentration of 5-40 mM.

Clause 30. The method of clause 18, wherein the recombinant cell is *Escherichia coli*.

Clause 31. A method for producing a ribosomally synthesized and posttranslationally modified peptide (RiPP), comprising combining at least one RiPP heterocyclase, at least one RiPP leader protease, at least one RiPP macrocyclase, at least one RiPP heterocyclase substrate, and a sulfide source to form a mixture, under conditions sufficient to convert the RiPP heterocyclase substrate into a ribosomally synthesized and posttranslationally modified peptide.

Clause 32. The method of clause 31, wherein the RiPP heterocyclase substrate is a TruE variant.

Clause 33. The method of clause 31, wherein the RiPP heterocyclase substrate is a PatE variant.

Clause 34. The method of clause 31, wherein the mixture further comprises a RiPP prenyl transferase.

Clause 35. A recombinant cell comprising a nucleic acid encoding a tru or pat protein and a nucleic acid encoding a mev protein, wherein the recombinant cell produces a ribosomally synthesized and posttranslationally modified peptide (RiPP).

Clause 36. The recombinant cell of clause 35, wherein the recombinant cell is *Escherichia coli*.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method for producing a ribosomally synthesized and posttranslationally modified peptide (RiPP), comprising culturing a recombinant cell in the presence of exogenous mevalonate, wherein the recombinant cell comprises a nucleic acid encoding a tru protein or a pat protein, and wherein the recombinant cell comprises a nucleic acid encoding a mev protein.

2. The method of claim 1, wherein the recombinant cell expresses ERG12, ERG8, and MVD1.

3. The method of claim 1, further comprising culturing the recombinant cell in the presence of an exogenous sulfide source.

4. The method of claim 3, wherein the exogenous sulfide source comprises cysteine.

5. The method of claim 4, wherein cysteine is provided at a concentration of 0.5-40 mM.

6. The method of claim 4, wherein cysteine is provided at a concentration of 5-10 mM.

7. The method of claim 3, wherein the exogenous sulfide source comprises cystine.

8. The method of claim 3, wherein the exogenous sulfide source comprises hydrogen sulfide.

9. The method of claim 3, wherein the exogenous sulfide source comprises sodium hydrosulfide.

10. The method of claim 1, wherein the recombinant cell expresses a TruE variant.

11. The method of claim 1, wherein the recombinant cell expresses a PatE variant.

12. The method of claim 1, wherein the exogenous mevalonate is provided at a concentration of 5-40 mM.

13. The method of claim 1, wherein the recombinant cell is *Escherichia coli*.

* * * * *

UNITED STATES PATENT AND TRADEMARK OFFICE
CERTIFICATE OF CORRECTION

| | |
|---|---|
| PATENT NO. | : 11,104,929 B2 |
| APPLICATION NO. | : 16/915927 |
| DATED | : August 31, 2021 |
| INVENTOR(S) | : Schmidt |

It is certified that error appears in the above-identified patent and that said Letters Patent is hereby corrected as shown below:

In the Specification

Column 1 Line 21 delete:
"This invention was made with government support under GM102602 awarded by the National Institutes of Health. The government has certain rights in the invention."

And replace it with:
--"This invention was made with government support under GM102602 and R01 GM071425 awarded by the National Institutes of Health and grant no. 0412226 awarded by the National Science Foundation, The government has certain rights in the invention."--

Signed and Sealed this
Third Day of September, 2024

Katherine Kelly Vidal
*Director of the United States Patent and Trademark Office*

SEQUENCE LISTING

```
<160> NUMBER OF SEQ ID NOS: 11

<210> SEQ ID NO 1
<211> LENGTH: 5
<212> TYPE: PRT
<213> ORGANISM: Artificial sequence
<220> FEATURE:
<223> OTHER INFORMATION: Synthetic

<400> SEQUENCE: 1

Gly Val Asp Ala Ser
1               5

<210> SEQ ID NO 2
<211> LENGTH: 3
<212> TYPE: PRT
<213> ORGANISM: Artificial sequence
<220> FEATURE:
```

```
<223> OTHER INFORMATION: Synthetic

<400> SEQUENCE: 2

Ser Tyr Asp
1

<210> SEQ ID NO 3
<211> LENGTH: 4
<212> TYPE: PRT
<213> ORGANISM: Artificial sequence
<220> FEATURE:
<223> OTHER INFORMATION: Synthetic

<400> SEQUENCE: 3

Ser Tyr Asp Asp
1

<210> SEQ ID NO 4
<211> LENGTH: 26
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is Thiazoline
<220> FEATURE:
<221> NAME/KEY: MISC_FEATURE
<222> LOCATION: (22)..(22)
<223> OTHER INFORMATION: Xaa is Thiazoline

<400> SEQUENCE: 4

Thr Leu Pro Val Pro Thr Leu Xaa Ser Tyr Asp Gly Val Asp Ala Ser
1               5                   10                  15

Thr Val Pro Thr Leu Xaa Ser Tyr Asp Asp
            20                  25

<210> SEQ ID NO 5
<211> LENGTH: 26
<212> TYPE: PRT
<213> ORGANISM: Artificial sequence
<220> FEATURE:
<223> OTHER INFORMATION: Synthetic

<400> SEQUENCE: 5

Thr Leu Pro Val Pro Thr Leu Cys Ser Tyr Asp Gly Val Asp Ala Ser
1               5                   10                  15

Thr Val Pro Thr Leu Cys Ser Tyr Asp Asp
            20                  25

<210> SEQ ID NO 6
<211> LENGTH: 16
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is Thiazoline

<400> SEQUENCE: 6

Thr Leu Pro Val Pro Thr Leu Xaa Ser Tyr Asp Gly Val Asp Ala Ser
1               5                   10                  15

<210> SEQ ID NO 7
```

```
<211> LENGTH: 10
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa is Thiazoline

<400> SEQUENCE: 7

Thr Val Pro Thr Leu Xaa Ser Tyr Asp Asp
1               5                   10

<210> SEQ ID NO 8
<211> LENGTH: 79
<212> TYPE: DNA
<213> ORGANISM: Artificial sequence
<220> FEATURE:
<223> OTHER INFORMATION: Synthetic

<400> SEQUENCE: 8
agtgtacagg gccccccctc gagggtatcg ataagcttga tatcgaattc ctgcagtagg      60
aggaattaac ccatatgtc                                                  79

<210> SEQ ID NO 9
<211> LENGTH: 78
<212> TYPE: DNA
<213> ORGANISM: Artificial sequence
<220> FEATURE:
<223> OTHER INFORMATION: Synthetic

<400> SEQUENCE: 9
gatgagctcc accgcggtgg cggccgctct agaactagtg atcccccgg gtaccatgga       60 catatgggtt aattcctc                                                   78

<210> SEQ ID NO 10
<211> LENGTH: 75
<212> TYPE: PRT
<213> ORGANISM: Artificial sequence
<220> FEATURE:
<223> OTHER INFORMATION: Synthetic

<400> SEQUENCE: 10

Met Asn Lys Lys Asn Ile Leu Pro Gln Leu Gly Gln Pro Val Ile Arg
1               5                   10                  15

Leu Thr Gly Gly Ser His His His His His His Ser Gly Ala Gly Gln
            20                  25                  30

Leu Ser Ser Gln Leu Ala Glu Leu Ser Glu Glu Ala Leu Gly Gly Val
        35                  40                  45

Asp Ala Ser Thr Val Pro Thr Leu Cys Ser Tyr Asp Gly Val Asp Ala
    50                  55                  60

Ser Thr Val Pro Thr Leu Cys Ser Tyr Asp Asp
65                  70                  75

<210> SEQ ID NO 11
<211> LENGTH: 77
<212> TYPE: PRT
<213> ORGANISM: Artificial sequence
<220> FEATURE:
<223> OTHER INFORMATION: Synthetic

<400> SEQUENCE: 11

Met Gly Ser Ser His His His His His His Ser Gly Gly Met Asn Lys
```

-continued

```
1               5                   10                  15

Lys Asn Ile Leu Pro Gln Leu Gly Gln Pro Val Ile Arg Leu Thr Ala
            20                  25                  30

Gly Gln Leu Ser Ser Gln Leu Ala Glu Leu Ser Glu Glu Ala Leu Gly
        35                  40                  45

Gly Val Asp Ala Ser Thr Val Pro Thr Leu Cys Ser Tyr Asp Gly Val
    50                  55                  60

Asp Ala Ser Thr Val Pro Thr Leu Cys Ser Tyr Asp Asp
65                  70                  75
```